(12) United States Patent
Castillo et al.

(10) Patent No.: US 9,133,176 B2
(45) Date of Patent: *Sep. 15, 2015

(54) ISOLATION, PURIFICATION AND SYNTHESIS OF PROCYANIDIN B2 AND USES THEREOF

(75) Inventors: Gerardo Castillo, Bothell, WA (US); Beth Nguyen, Gurnee, IL (US); Paula Choi, Seattle, WA (US); Lesley Larsen, Dunedin (NZ); Stephen Lorimer, Dunedin (NZ); Alan Snow, Lynnwood, WA (US)

(73) Assignee: PROTEOTECH INC., Kirkland, WA (US)

( * ) Notice: Subject to any disclaimer, the term of this patent is extended or adjusted under 35 U.S.C. 154(b) by 1395 days.

This patent is subject to a terminal disclaimer.

(21) Appl. No.: 12/119,212

(22) Filed: May 12, 2008

(65) Prior Publication Data
US 2008/0306142 A1 Dec. 11, 2008

Related U.S. Application Data

(63) Continuation of application No. 10/684,178, filed on Oct. 10, 2003, now abandoned, and a continuation-in-part of application No. 12/470,374, filed on May 21, 2009, which is a continuation of (Continued)

(51) Int. Cl.
*C07D 323/00* (2006.01)
*C07D 321/00* (2006.01)
*C07D 311/00* (2006.01)

(Continued)

(52) U.S. Cl.
CPC .......... *C07D 407/04* (2013.01); *C07D 311/62* (2013.01); *C07D 321/10* (2013.01); *C07D 323/00* (2013.01)

(58) Field of Classification Search
CPC ... C07D 323/00; C07D 321/10; C07D 311/62
USPC ................................. 549/349, 350, 354, 399
See application file for complete search history.

(56) References Cited

U.S. PATENT DOCUMENTS

5,681,569 A * 10/1997 Kuznicki et al. .............. 424/439

FOREIGN PATENT DOCUMENTS

JP 10245342 A * 9/1998
WO WO/00/12102 3/2000

OTHER PUBLICATIONS

Hashimoto et al, Tannins and related Compounds, Chem. Pharm. Bull. vol. 37 No. 12 pp. 3255-3263 (1989).*

(Continued)

*Primary Examiner* — Andrew D Kosar
*Assistant Examiner* — Raymond Covington
(74) *Attorney, Agent, or Firm* — Rebecca Eagen

(57) ABSTRACT

Methods for the synthesis, isolation, and purification of procyanidin B2 are disclosed. The synthetic methods utilize epicatechin as a starting material and produce procyanidin B2 in high yields. The isolation methods extract procyanidin B2 from a sample of bark powder from plant matter of the genus *Uncaria*. The isolated and/or synthesized procyanidin B2 is used to treat amyloid disease, such as Alzheimer's disease and Parkinson's disease as well as improve cognitive performance and increase learning and memory in Alzheimer's patients. Pharmaceutical compositions containing the synthesized and/or isolated procyanidin B2 are also disclosed.

9 Claims, 27 Drawing Sheets

Related U.S. Application Data application No. 10/077,596, filed on Feb. 15, 2002, now abandoned.

(60) Provisional application No. 60/418,093, filed on Oct. 11, 2002, provisional application No. 60/423,089, filed on Nov. 1, 2002.

(51) Int. Cl.
    *C07D 407/04*    (2006.01)
    *C07D 321/10*    (2006.01)
    *C07D 311/62*    (2006.01)

(56) References Cited

OTHER PUBLICATIONS

U.S. Appl. No. 10/077,596, filed Jan. 23, 2003, Snow et al.
Arai et al., "Argyrophilic glial inclusions in the midbrain of patients with Parkinson's disease and diffuse Lewy body disease are . . . ", Neurosc. Lett. 259:83-86 (1999).
Arnaudinaud et al., "Total synthesis of isotopically labelled flavonoids. Part 5:Gram-scale production of 13C-labelled . . . ", Tetrahedron Letters 42:5669-5671 (2001).
Askanas et al., "β-Amyloid Precursor Epitopes in Muscle Fibers of Inclusion Body Myositis", Ann. Neurol. 34: 551-560 (1993).
Bell E.T., "Hyalinization of the islets of langerhans in nondiabetic individuals", Am. J. Pathol. 35:801-805 (1959).
Benson et al., "Serum Amyloid a Protein in Amyloidosis, Rheumatic, and Neoplastic Diseases", Arthritis and Rheumatism 22(1): 36-42 (1979).
Clark et al., "Localisation of islet and amyloid peptide in lipofuscin bodies and secretory granules of human B-cells and in islets . . . ", Cell Tissue Res. 257:179-185 (1989).
Clark et al., "Islet Amyloid, Increased A-Cells, Reduced B-Cells and Exocrine Fibrosis: Quantitative Changes in the Pancreas . . . ", Diabetes Res. 9:151-159 (1988).
Conway et al., "Accelerated in vitro fibril formation by a mutant α-synuclein linked to early-onset Parkinson disease", Nature Med. 4:1318-1320 (1998).
Czochanska et al., "Direct Proof of a Homogenous Polyflavan-3-ol Structure for Polymeric Proanthocyanidis", J. C. S. Chem. Comm. pp. 375-377 (1979).
Davidson et al., "The Effect of Aging on Carbohydrate Metabolism: A Review of the English Literature and Practical Approach to . . . ", Metabolism 28(6):688-705 (1979).
Fletcher et al., "Plant Proanthocyanidins. Part 3. Conformational and Configurational Studies of Natural Procyanidins", JCS Perkin 1:1628-1637 (1977).
Flood et al., "Amnestic effects in mice of four synthetic peptides homologous to amyloid β protein from patients . . . ", Proc. Natl. Acad. Sci. USA 88:3363-3366 (1991).
Flood et al., "An amyloid β-protein fragment, Aβ[12-28], equipotently impairs post-training memory processing when injected . . . ", Brain Research 663:271-276 (1994).
Games et al., "Alzheimer-type neuopathology in transgenic mice overexpressing V717F β-amyloid precursor protein", Nature 373: 523-527 (1995).
Gejyo et al., "A New Form of Protein Associated with Chronic Hemodialysis was Identified as β2 -Microglobulin ", Biochem. Biophys. Res. Com. 129(3): 701-706 (1985).
Gejyo et al., "β2-microglobulin: A new form of protein associated with chronic hemodialysis", Kidney International 30:385-390 (1986).
Glenner, G. and Wong, C., "Alzheimer's Disease: Initial Report of the Purification and Characterization of a Novel . . . ", Biochem. Biophys. Res. Com. 120(3): 885-890 (1984).
Grundke-Iqbal et al., "Abnormal phosphorylation of the microtubule-associated protein τ (tau) in Alzheimer cytoskeletal . . . ", Proc. Natl. Acad. Sci. USA 83:4913-4917 (1986).

Gujer et al., "Glucosylated Flavonoids and Other Phenolic Compounds From Sorghum", Photochemistry 25:1431-1436 (1986).
Haass et al., "The Swedish mutation causes early-onset Alzheimer's disease by β-secretase cleavage within the secretory pathway", Nature Medicine 1(12):1291-1296 (1995).
Harada et al., "Human Amyloid Protein: Chemical Variability and Homogeneity", Journal of Histochemistry and Cytochemistry 19(1): 1-15 (1971).
Hardy J., "Framing β-amyloid", Nature Genet. 1:233-234 (1992).
Harrigan et al., "Beta Amyloid is Neurotoxic in Hippocampal Slice Cultures", The Neurobiology of Aging 16(5): 779-789 (1995).
Hashimoto et al., "Human recombinant NACP/α-synuclein is aggregated and fibrillated in vitro: Relevance for Lewy body disease", Brain Res. 799:301-306 (1998).
Hemingway et al., "Linkage Isomerism in Trimeric and Polymeric 2,3-cis-Procyanidins", J. Chem. Soc. Perkins Trans. 1:1209-1216 (1982).
Hsiao et al., "Correlative Memory Deficits, Aβ Elevation, and Amyloid Plaques in Transgenic Mice", Science 274:99-102 (1996).
Ishimaru et al., "Flavan-2-ol and Procyanidin Glycosides from Quercus Miyagii", Phytochemistry 26:1167-1170 (1987).
Janson et al., "Human Islet Amyloid Polypeptide (hIAPP) Cytotoxicity is caused by Membrane Damage", Diabetes 47:A250 (1998).
Johnson et al., "Islet Amyloid Polypeptide: Mechanisms of Amyloidogenesis in the Pancreatic Islet s and Potential Roles . . . ", Laboratory Investigation 66(5): 522-534 (1992).
Johnson et al., "Islet Amyloid, Islet-Amyloid Polypeptide, and Diabetes Mellitus", The New England Journal of Medicine 321(8): 513-518 (1989).
Jones et al., "The Condensed Tannins of Pasture Legume Species", Photochemistry 15:1407-1409 (1976).
Kahn et al., "Evidence of Cosecretion of Islet Amyloid Polypeptide and Insulin by β-Cells", Diabetes 39:634-638 (1990).
Kamei et al., "Amyloidosis Associated with Juvenile Rheumatoid Arthritis", Acta Pathol. Jpn. 32(1):123-133 (1982).
Kawamoto et al., "O-Benzylation of Phloroglucinol via Phloroglucinol Triacetate", Synthetic Communications 26(3):531-534 (1996).
Kitaguchi et al., "Novel precursor of Alzheimer's disease amyloid protein shows protease inhibitory activity", Nature 331:530-532 (1988).
Kosik et al., "Microtubule-associated protein tau (τ) is a major antigenic component of paired helical filaments . . . ", Procl. Natl. Acad. Sci. USA 83:4044-4048 (1986).
Kruger et al., "Ala30Pro mutation in the gene encoding α-synuclein in Parkinson's disease", Nature Genet. 18:106-108 (1998).
Lee et al., "A68: A Major Subunit of Paired Helical Filaments and Derivatized Forms of Normal Tau", Science 251: 675-678 (1991).
LeVine III H., "Thioflavine T interaction with synthetic Alzheimer's disease β-amyloid peptides: Detection of amyloid aggregation in solution", Protein Sci. 2:404-410 (1993).
LeVine III H., "Thioflavine T interacton with amyloid β-sheet structures", Amyloid: Int. J. Exp. Clin. Invest. 2:1-6 (1995).
Lewy et al., "Die angeborenen Defekte und Entwickelungsstorungen des Gehirns", in Handbuch der Neurologie, Berlin:Springer-Verlag pp. 920-933 (1912) [in German].
Lorenzo et al., "Pancreatic islet cell toxicity of amylin associated with type-2 diabetes mellitus", Nature 368:756-760 (1994).
Mandybur et al., "Cerebral Amyloid Angiopathy: The Vascular Pathology and Complications", Journal of Neuropathology and Experimental Neurology 45(1): 79-90 (1986).
Masters et al., "Amyloid plaque core protein in Alzheimer disease and Down syndrome", Proc. Natl. Acad. Sci. USA 82:4245-4249 (1985).
Matthews et al., "Method for estimation of Proanthocyanidins based on their acid depolymerization in the presence of nucleophiles", J. Agric. Food Chem. 45:1195-1201 (1997).
Mattice et al., "Molecular weight averages and 13C NMR intensities provide evidence for branching in proanthocyanidin polymers", Phytochem. 23(6):1309-1311 (1984).
McAdam et al. , "Association of Amyloidosis with Erythema Nodosum Leprosum Reactions and Recurrent Neutrophil Leucocytosis . . . ", The Lancet pp. 572-575, Sep. 27, 1975.

(56) References Cited

OTHER PUBLICATIONS

Metaxas et al., "Familial Mediterranean fever and amyloidosis", Kidney International 20:676-685 (1981).
Murrell et al., "A mutation in the Amyloid Precursor Protein Associated with Hereditary Alzheimer's Disease", Science 254: 97-99 (1991).
Nahri et al., "Both Familial Parkinson's Disease Mutations Accelerate α-Synuclein Aggregation", J. Biol. Chem. 274:9843-9846 (1999).
Naiki, H. and Nakakuki, K., "Kinetic Analysis of Amyloid Fibril Polymerization In vitro", Laboratory Investigation 65(1):104-110(1991).
Nay et al., "Gram-Scale Production and Applications of Optically Pure 13C-Labelled (+)-Catechin and (−)-Epicatechin", Eur. J. Org. Chem. pp. 2379-2384 (2001).
Nonaka et al., "Tannins and Related Compound. XV.1) A New Class of Dimeric Flavan-3-ol Gallates, Theasinensins A and B, and . . . ", Chem. Pharxn. Bull. 31:3906-3914 (1983).
Pardridge et al., "Amyloid Angiopathy of Alzheimer's Disease: Amino Acid Composition and Partial Sequence of a 4,200-Dalton . . . ", J. of Neurochemisty 49(5): 1394-1401 (1987).
Piao et al., "Co-localization of a-synuclein and phosphorylated tau in neuronal and glial cytoplasmic inclusions in a patient with . . . ", Acta Neuropathol. 101:285-¬ 1293 (2001).
Pike et al., "In vitro aging of β-amyloid protein cause peptide aggregation and neurotoxicity", Brain Research 563:311-314 (1991).
Pike et al., "Structure-Activity Analyses of β-Amyloid Peptides: Contributions of the β25-35 Region to Aggregation and . . . ", Journal of Neurochemistry 64(1): 253-265 (1995).
Pollanen et al., "Pathology and Biology of the Lewy Body", Journal of Neuropathology and Experimental Neurology 52(3):183-191 (1993).
Polymeropoulos et al., "Mutation in the α-Synuclein Gene Identified in Families with Parkinson's Disease", Science, 276:2045-2047 (1997).
Ponte et al. ,"A new A4 amyloid mRNA contains a domain homologous to serine proteinase inhibitors", Nature 311:525-527 (1988).
Porter et al., "Isolation of three naturally occuring O-J-glucopyranodsides of procyanidin polymers", Phytochemistry 24:567-569 (1985).
Porter L.J, "Flavans and proanthocyanidins", Chapter 2 in Flavans and proanthocyanidins—Advances in Research since 1986, London: Chapman and Hall pp. 23-55 (1994).
Porter L.J, "Flavans and proanthocyanidins," Chapter 2 in the Flavanoids—Advances in Research since 1980, J B Harborne (Ed.), London: Chapman and Hall, pp. 21-62 (1988).
Prieur et al., "Oligomeric and polymeric procyanidins from grape seeds", Phyochem. 36:781-784 (1994).
Puchtler et al., "On the Binding of Congo Red by Amyloid", J. Histochem. Cytochem. 10:355-364 (1962).
Santos-Buelga, C. and Scalbert, A., "Proanthocyanidins and tannin-like compounds—nature, occurrence, dietary intake . . . ", J. Sci.. Food Agri. 80: 1094-1117 (2000).
Saraiva et al., "Amyloid Fibril Protein in Familial Amyloidotic Polyneurotherapy, Portuguese Type", J. Clin. Invest. 74:104-119 (1984).
Saraiva et al., "Studies on plasma transthyretin (prealbumin) in familial amyloidotic polyneropathy, Portuguese type", J. Lab. Clin. Med. 102(4): 590-603 (1983).
Skinner et al., "The Prealbumin Nature of the Amyloid Protein in Familial Amyloid Polyneuropathy (FAP)—Swedish Variety", Biochem Bipophy. Res. Com. 99(4):1326-1332 (1981).
Spillantini et al., "α-Synuclein in filamentous inclusions of Lewy bodies from Parkinson's disease and dementia with Lewy . . . ", Proc. Natl. Acad. Sci. USA. 95:6469-6473 (1998).
Steynberg et al., "Oligomeric flavanoids. Part 27. Interflavanyl bond formation in procyanidins under neutral conditions", Tetrahedron 54:8153-8158 (1998).
Tanzi et al., "Protease inhibitor domain encoded by an amyloid protein precursor mRNA associated with Alzheimer's disease", Nature 331:528-532 (1988).
Tawara et al., "Amyloid fibril protein in type 1 familial amyloidotic polyneurotherapy in Japanese", J. Lab. Clin. Med. 98(6): 811-822 (1981).
Thompson et al., "Plant Proanthocyanidins. Part 1. Introduction; the Isolation, Structure, and Distribution in Nature . . . ", J. Chem. Soc. Perkins Trans. 1: 1387-1399 (1972).
Tuckmantel "Studies in Polyphenol Chemistry and Bioactivity. 1. Preparation of Building Blocks from (+)-Catechin. Procyanidin . . . ", J. Am. Chem. Soc. 121:12073-12081 (1999).
Ueda et al., "Molecular cloning of cDNA encoding an unrecognized component of amyloid in Alzheimer disease", Proc. Natl. Acad. Sci. USA 90:11282-11286 (1993).
Van Broeckhoven et al., "Amyloid β Protein Precursor Gene and Hereditary Cerebral Hemorrhage with Amyloidosis (Dutch)", Science 248:1120-1122 (1990).
Verchere et al., "Islet amyloid formation associated with hyperglycemia in transgenic mice with pancreatic beta cell . . . ", Proc. Natl. Acad. Sci. U.S.A. 93: 3492-3496 (1996).
Wakabayashi et al., "Accumulation of α-Synuclein/NACP is a cytopathological feature common to Lewy body disease and multiple . . . ", Acta Neuropath. 96: 445-452 (1998).
Westermark et al., "Amyloid and polypeptide hormones: what is their interrelationship?", Amyloid: Int. J. Exp. Clin. Invest. 1:47-60 (1994).
Westermark et al., "Quantitative Studies of Amyloid in the Islets of Langerhans", Upsala J. Med. Sci. 77:91-94 (1972).
Westermark et al., "The Influence of Amyloid Deposits on the Islet Volume in Maturity Onset Diabetes Mellitus", Diabetologica 15:417-421 (1978).
Wood et al., "α-Synuclein Fibrillogenesis Is Nucleation-dependent", J. Biol. Chem. 274:19509-19512 (1999).
Zhang et al., "Potentillanin, A Biflavanoid and a procyanidin glycoside from potentilla viscosa", Phytochemistry 27:3277-3280 (1988).

* cited by examiner

Fractions: each one eluted until silica dries
1. 250 ml 10% methanol/chloroform
2. 250 ml 10% methanol/chloroform
3. 250 ml 20% methanol/chloroform
4. 250 ml 20% methanol/chloroform
5. 250 ml 40% methanol/chloroform
6. 250 ml 40% methanol/chloroform
7. 250 ml 60% methanol/chloroform
8. 250 ml 60% methanol/chloroform

US 9,133,176 B2

ISOLATION, PURIFICATION AND SYNTHESIS OF PROCYANIDIN B2 AND USES THEREOF

CROSS-REFERENCE TO RELATED APPLICATIONS

This application is a continuation of U.S. application Ser. No. 10/684,178 filed Oct. 10, 2003 now abandoned which claimed priority under 35 USC 119(e) of U.S. Provisional Application No. 60/418,093, filed Oct. 11, 2002, and U.S. Provisional Application No. 60/423,089, filed Nov. 1, 2002. This application is a continuation-in-part of, and also claims priority under 35 USC 120 to, the copending nonprovisional application U.S. Ser. No. 12/470,374 filed May 21, 2009 which is a continuation of U.S. application Ser. No. 10/077,596 filed Feb. 15, 2002, now abandoned.

GOVERNMENT INTERESTS

Work described herein was made with government support under 2 R44 AG16551-02 awarded by the National Institute on Aging. The U.S. Government may have certain rights in subject matter provided herein.

TECHNICAL FIELD

Provided herein are new methods of isolation and synthesis of procyanidin B2 (also referred to as epicatechin-4β→8-epicatechin or procyanidin B2 dimer or epicatechin-epicatechin dimer) and uses therefore. In the isolation methods, procyanidin B2 is isolated from *Uncaria tomentosa* (also known as cat's claw) and related plants. In the syntheses, procyanidin B2 is prepared via a synthetic route that is shorter and results in a 5-fold higher yield synthesis of procyanidin B2 than has been previously reported. The use of procyanidin B2 and related procyanidins relates to methods and compositions for treatment and prevention of amyloid and α-synuclein diseases, such as Alzheimer's disease and Parkinson's disease, more particularly it relates to procyanidin B2 and related compounds for treatment and prevention of amyloid and α-synuclein diseases.

BACKGROUND

Alzheimer's disease is characterized by the accumulation of a 39-43 amino acid peptide termed the beta-amyloid protein or Aβ, in a fibrillar form, existing as extracellular amyloid plaques and as amyloid within the walls of cerebral blood vessels. Fibrillar Aβ amyloid deposition in Alzheimer's disease is believed to be detrimental to the patient and eventually leads to toxicity and neuronal cell death, characteristic hallmarks of Alzheimer's disease. Accumulating evidence implicates amyloid, and more specifically, the formation, deposition, accumulation and/or persistence of Aβ fibrils, as a major causative factor of Alzheimer's disease pathogenesis. In addition, besides Alzheimer's disease, a number of other amyloid diseases involve accumulation of Aβ fibrils, including Down's syndrome, disorders involving congophilic angiopathy, hereditary cerebral hemorrhage of the Dutch type, and inclusion body myositosis.

Parkinson's disease is another human disorder characterized by the formation, deposition, accumulation and/or persistence of abnormal fibrillar protein deposits that demonstrate many of the characteristics of amyloid. In Parkinson's disease, an accumulation of cytoplasmic Lewy bodies consisting of filaments of α-synuclein/NAC (i.e., non-amyloid component) are believed important in the pathogenesis and as therapeutic targets. New agents or compounds able to inhibit α-synuclein/NAC formation, deposition, accumulation and/or persistence, or disrupt pre-formed α-synuclein/NAC fibrils (or portions thereof) are regarded as potential therapeutics for the treatment of Parkinson's disease.

A variety of other human diseases also demonstrate amyloid deposition and usually involve systemic organs (i.e., organs or tissues lying outside the central nervous system), with the amyloid accumulation leading to organ dysfunction or failure. These amyloid diseases (discussed below) leading to marked amyloid accumulation in a number of different organs and tissues are known as systemic amyloidoses. In other amyloid diseases, single organs may be affected, such as the pancreas in 90% of patients with type 2 diabetes. In this type of amyloidosis, the beta-cells in the islets of Langerhans in pancreas are believed to be destroyed by the accumulation of fibrillar amyloid deposits consisting primarily of a protein known as islet amyloid polypeptide (IAPP). Inhibiting or reducing such amyloid accumulation is believed to lead to new effective treatments for type 2 diabetes. In Alzheimer's disease, Parkinson's and "systemic" amyloid diseases, there is currently no cure or effective treatment, and the patient usually dies within 3 to 10 years from disease onset.

SUMMARY

In one of its aspects, the present disclosure relates to methods for synthesizing procyanidin B2 wherein an epicatechin is esterified to form a 5,7,3',4',3"-penta-O-acyl-epicatechin. The 5,7,3',4',3"-penta-O-acyl-epicatechin is protected to form a 5,7,3',4'-tetra-O-protected epicatechin. An adduct precursor is then coupled with a first portion of the 5,7,3',4'-tetra-O-protected epicatechin to form a 4"-substituted, 5,7,3',4'-tetra-O-protected epicatechin. A second portion of the 5,7,3',4'-tetra-O-protected epicatechin is dimerized with the 4"-substituted, 5,7,3',4'-tetra-O-protected epicatechin to form a 5,7,3',4'-tetra-O-protected epicatechin-4β→8-5,7,3',4'-tetra-O-protected epicatechin. The 5,7,3',4'-tetra-O-protected epicatechin-4β→8-5,7,3',4'-tetra-O-protected epicatechin is deprotected to form procyanidin B2. In one embodiment, the epicatechin is esterified by acetylation form a 5,7,3',4',3"-penta-O-acetyl-epicatechin. In another embodiment, the 5,7,3',4',3"-penta-O-acyl-epicatechin is protected by benzylation to form a 5,7,3',4'-tetra-O-benzylepicatechin. In another embodiment, the 5,7,3',4',4"-penta-O-acyl-epicatechin is protected by reaction of the 5,7,3',4',4"-penta-O-acyl-epicatechin with benzylchloride in the presence of water. In another embodiment, the 5,7,3',4',4"-penta-O-acyl-epicatechin is reacted with between about 4.0 and about 4.2 equivalents of benzylchloride for between about 24 hours and about 72 hours to form a reaction mixture comprising the 5,7,3',4'-tetra-O-benzylepicatechin. In yet another embodiment, the reaction mixture is combined with an acid, such as hydrochloric acid (e.g., between about 0.01 M and about 3 M hydrochloric acid). In another embodiment, the acid is chilled (e.g., to between about −10° C. and about +10° C. In a further embodiment, an ethylene glycol is coupled with the first portion of the 5,7,3',4'-tetra-O-protected epicatechin to form a 5,7,3',4'-tetra-O-protected 4-(2-hydroxyethoxy)epicatechin. In still a further embodiment, the 5,7,3',4'-tetra-O-protected epicatechin-4B 8-5,7,3',4'-tetra-O-protected epicatechin dimer is purified by crystallization and isolation using column chromatography.

In another of its aspects, the present disclosure relates to methods for synthesizing a 5,7,3',4'-tetra-O-protected epicatechin wherein an epicatechin is esterified to form a 5,7,3',4', 3"-penta-O-acyl-epicatechin. The 5,7,3',4',4"-penta-O-acyl-epicatechin is then protected to form a 5,7,3',4'-tetra-O-protected epicatechin.

In yet another of its aspects, the present disclosure relates to methods for isolating procyanidin B2 wherein a sample of bark powder from plant matter of the genus *Uncaria* is extracted with an alcohol to form an extract. The extract is fractionated using flash vacuum fractionation to form a plurality of flash vacuum fractions of extract. The flash vacuum fractions are analyzed to determine which flash vacuum fractions contain procyanidin B2. One or more of the flash vacuum fractions identified as containing procyanidin B2 is then fractionated using silica gel column chromatography to form a plurality of silica gel fractions. The silica gel fractions are analyzed to determine which silica gel fractions contain procyanidin B2. One or more of the silica gel fractions identified as containing procyanidin B2 is then fractionated using Sephadex LH20 column chromatography to form a plurality of Sephadex LH20 fractions. In one embodiment, the extraction is accomplished by stirring a mixture of the sample of bark powder and methanol, and filtering the mixture to obtain a filtrate. In a particular embodiment, the stirred mixture is allowed to settle prior to filtration. In an alternate embodiment, the stirred mixture is centrifuged prior to filtration. In another embodiment, the flash vacuum fractions, the silica gel fractions, and/or the Sephadex LH20 fractions are analyzed by thin layer chromatography (TLC) and/or high pressure liquid chromatography (HPLC).

In still another of its aspects, the present disclosure relates to methods for treating the formation, deposition, accumulation, or persistence of amyloid fibrils wherein the fibrils are treated with an effective amount of a procyanidin B2 synthesized in accordance with the methods disclosed herein. In one embodiment, the amyloid fibrils are Aβ amyloid fibrils. In an alternate embodiment, the amyloid fibrils are IAPP amyloid fibrils.

In addition, the present disclosure relates to methods for treating the formation, deposition, accumulation, or persistence of synuclein fibrils wherein the synuclein fibrils are treated with an effective amount of a procyanidin B2 synthesized in accordance with the present disclosure. In one embodiment, the synuclein fibrils are α-synuclein/NAC fibrils.

In still a further of its aspects, the present disclosure relates to methods for treating an amyloid disease or a synucleinopathy in a mammal (e.g., a human) wherein a therapeutically effective amount of a procyanidin B2 synthesized in accordance with the methods disclosed herein is administered to the mammal. In one embodiment, the amyloid disease is a disease associated with the formation, deposition, accumulation, or persistence of an Aβ amyloid, AA amyloid, AL amyloid, IAPP amyloid, $\alpha_2$-microglobulin amyloid, transthyretin, prealbumin, and/or procalcitonin. In a particular embodiment, the amyloid disease is selected from the group of diseases consisting of Alzheimer's disease, Down's syndrome, dementia pugilistica, multiple system atrophy, inclusion body myositosis, hereditary cerebral hemorrhage with amyloidosis of the Dutch type, Nieman-Pick disease type C, cerebral β-amyloid angiopathy, dementia associated with cortical basal degeneration, the amyloidosis of type 2 diabetes, the 30 amyloidosis of chronic inflammation, the amyloidosis of malignancy and Familial Mediterranean Fever, the amyloidosis of multiple myeloma and B-cell dyscrasias, the amyloidosis of the prion diseases, Creutzfeldt-Jakob disease, Gerstmann-Straussler syndrome, kuru, scrapie, the amyloidosis associated with carpal tunnel syndrome, senile cardiac amyloidosis, familial amyloidotic polyneuropathy, and the amyloidosis associated with endocrine tumors. In an alternate embodiment, the synucleinopathy is a disease associated with the formation, deposition, accumulation, or persistence of synuclein fibrils such as, for example, α-synuclein fibrils. In a particular embodiment, the synucleinopathy is selected from the group of diseases consisting of Parkinson's disease, familial Parkinson's disease, Lewy body disease, the Lewy body variant of Alzheimer's disease, dementia with Lewy bodies, multiple system atrophy, and the Parkinsonism-dementia complex of Guam. In still another embodiment, the amount of procyanidin B2 administered is between about 0.1 mg/kg of body weight per day and about 1000 mg/kg of body weight per day; between about 1 mg/kg of body weight per day and about 100 mg/kg of body weight per day; or between about 10 mg/kg of body weight per day and about 100 mg/kg of body weight per day.

Also, the present disclosure relates to methods for treating the formation, deposition, accumulation, or persistence of amyloid fibrils wherein the fibrils are treated with an effective amount of a procyanidin B2 isolated in accordance with the methods disclosed herein. In one embodiment, the amyloid fibrils are Aβ amyloid fibrils. In an alternate embodiment, the amyloid fibrils are IAPP amyloid fibrils.

In a further of its aspects, the present disclosure relates to methods for treating the formation, deposition, accumulation, or persistence of synuclein fibrils wherein the synuclein fibrils are treated with an effective amount of a procyanidin B2 isolated in accordance with the present disclosure. In one embodiment, the synuclein fibrils are α-synuclein fibrils.

Additionally, the present disclosure relates to methods for treating an amyloid disease or a synucleinopathy in a mammal (e.g., a human) wherein a therapeutically effective amount of a procyanidin B2 isolated in accordance with the methods disclosed herein is administered to the mammal. In one embodiment, the amyloid disease is a disease associated with the formation, deposition, accumulation, or persistence of an Aβ amyloid, AA amyloid, AL amyloid, IAPP amyloid, $\alpha_2$-microglobulin amyloid, transthyretin, prealbumin, and/or procalcitonin. In a particular embodiment, the amyloid disease is selected from the group of diseases consisting of Alzheimer's disease, Down's syndrome, dementia pugilistica, multiple system atrophy, inclusion body myositosis, hereditary cerebral hemorrhage with amyloidosis of the Dutch type, Nieman-Pick disease type C, cerebral β-amyloid angiopathy, dementia associated with cortical basal degeneration, the amyloidosis of type 2 diabetes, the amyloidosis of chronic inflammation, the amyloidosis of malignancy and Familial Mediterranean Fever, the amyloidosis of multiple myeloma and B-cell dyscrasias, the amyloidosis of the prion diseases, Creutzfeldt-Jakob disease, Gerstmann-Straussler syndrome, kuru, scrapie, the amyloidosis associated with carpal tunnel syndrome, senile cardiac amyloidosis, familial amyloidotic polyneuropathy, and the amyloidosis associated with endocrine tumors. In an alternate embodiment, the synucleinopathy is a disease associated with the formation, deposition, accumulation, or persistence of synuclein fibrils such as, for example, α-synuclein fibrils. In a particular embodiment, the synucleinopathy is selected from the group of diseases consisting of Parkinson's disease, familial Parkinson's disease, Lewy body disease, the Lewy body variant of Alzheimer's disease, dementia with Lewy bodies, multiple system atrophy, and the Parkinsonism-dementia complex of Guam. In still another embodiment, the amount of procyanidin B2 administered is between about 0.1 mg/kg of body weight per day and about 1000 mg/kg of body weight per day; between about 1 mg/kg of body weight per day and about 100 mg/kg of body weight per day; or between about 10 mg/kg of body weight per day and about 100 mg/kg of body weight per day.

The present disclosure relates to pharmaceutical compositions containing a procyanidin B2, synthesized and/or isolated in accordance with the methods disclosed herein, and a suitable excipient.

The present disclosure also relates to use of a procyanidin B2 synthesized in accordance with methods disclosed herein in the manufacture of a medicament for treating the formation, deposition, accumulation, or persistence of amyloid fibrils (e.g., Aβ amyloid fibrils and/or IAPP amyloid fibrils) and/or synuclein fibrils (e.g., α-synuclein fibrils).

In addition, the present disclosure relates to use of procyanidin B2 synthesized in accordance with the methods disclosed herein in the manufacture of a medicament for treating an amyloid disease or a synucleinopathy in a mammal. In one embodiment, the amyloid disease is a disease associated with the formation, deposition, accumulation, or persistence of Aβ amyloid, AA amyloid, AL amyloid, IAPP amyloid, $\alpha_2$-microglobulin amyloid, transthyretin, prealbumin, and/or procalcitonin. In a particular embodiment, the amyloid disease is Alzheimer's disease, Down's syndrome, dementia pugilistica, multiple system atrophy, inclusion body myositosis, hereditary cerebral hemorrhage with amyloidosis of the Dutch type, Nieman-Pick disease type C, cerebral β-amyloid angiopathy, dementia associated with cortical basal degeneration, amyloidosis of type 2 diabetes, amyloidosis of chronic inflammation, amyloidosis of malignancy and Familial Mediterranean Fever, amyloidosis of multiple myeloma and B-cell dyscrasias, amyloidosis of the prion diseases, Creutzfeldt-Jakob disease, Gerstmann-Straussler syndrome, kuru, scrapie, amyloidosis associated with carpal tunnel syndrome, senile cardiac amyloidosis, familial amyloidotic polyneuropathy, and/or amyloidosis associated with endocrine tumors. In another embodiment, the synucleinopathy is a disease associated with the formation, deposition, accumulation, or persistence of synuclein fibrils (e.g., α-synuclein fibrils). In a particular embodiment, the synucleinopathy is Parkinson's disease, familial Parkinson's disease, Lewy body disease, the Lewy body variant of Alzheimer's disease, dementia with Lewy bodies, multiple system atrophy, and/or the Parkinsonism-dementia complex of Guam.

The present disclosure also relates to use of a procyanidin B2 isolated in accordance with methods disclosed herein in the manufacture of a medicament for treating the formation, deposition, accumulation, or persistence of amyloid fibrils (e.g., Aβ amyloid fibrils and/or IAPP amyloid fibrils) and/or synuclein fibrils (e.g., α-synuclein fibrils).

Further, the present disclosure relates to use of procyanidin B2 isolated in accordance with the methods disclosed herein in the manufacture of a medicament for treating an amyloid disease or a synucleinopathy in a mammal. In one embodiment, the amyloid disease is a disease associated with the formation, deposition, accumulation, or persistence of Aβ amyloid, AA amyloid, AL amyloid, IAPP amyloid, $\alpha_2$-microglobulin amyloid, transthyretin, prealbumin, and/or procalcitonin. In a particular embodiment, the amyloid disease is Alzheimer's disease, Down's syndrome, dementia pugilistica, multiple system atrophy, inclusion body myositosis, hereditary cerebral hemorrhage with amyloidosis of the Dutch type, Nieman-Pick disease type C, cerebral β-amyloid angiopathy, dementia associated with cortical basal degeneration, amyloidosis of type 2 diabetes, amyloidosis of chronic inflammation, amyloidosis of malignancy and Familial Mediterranean Fever, amyloidosis of multiple myeloma and B-cell dyscrasias, amyloidosis of the prion diseases, Creutzfeldt-Jakob disease, Gerstmann-Straussler syndrome, kuru, scrapie, amyloidosis associated with carpal tunnel syndrome, senile cardiac amyloidosis, familial amyloidotic polyneuropathy, and/or amyloidosis associated with endocrine tumors. In another embodiment, the synucleinopathy is a disease associated with the formation, deposition, accumulation, or persistence of synuclein fibrils (e.g., α-synuclein fibrils). In a particular embodiment, the synucleinopathy is Parkinson's disease, familial Parkinson's disease, Lewy body disease, the Lewy body variant of Alzheimer's disease, dementia with Lewy bodies, multiple system atrophy, and/or the Parkinsonism-dementia complex of Guam.

In another of its aspects, the present disclosure relates to methods for treating pain, inflammation, viral infections, arthritis, rheumatism, bursitis, gout, opportunistic infections, skin tumors and cysts, cancer, AIDs, Crohn's disease, respiratory infections, allergies, herpes, prostrate problems, lupus, Epstein Barr virus, chronic fatigue syndrome, and stomach and bowel disorders in a mammal, wherein a therapeutically effective amount of a procyanidin B2 is administered to the mammal.

The present disclosure also relates to use of a procyanidin B2 in the manufacture of a medicament for treating pain, inflammation, viral infections, arthritis, rheumatism, bursitis, gout, opportunistic infections, skin tumors and cysts, cancer, AIDs, Crohn's disease, respiratory infections, allergies, herpes, prostrate problems, lupus, Epstein Barr virus, chronic fatigue syndrome, and stomach and bowel disorders in a mammal.

Still further, the present disclosure relates to products containing a procyanidin B2, synthesized and/or isolated in accordance with the methods disclosed herein, and a label indicating the intended method of treatment.

DETAILED DESCRIPTION

Definitions

Figure 1:
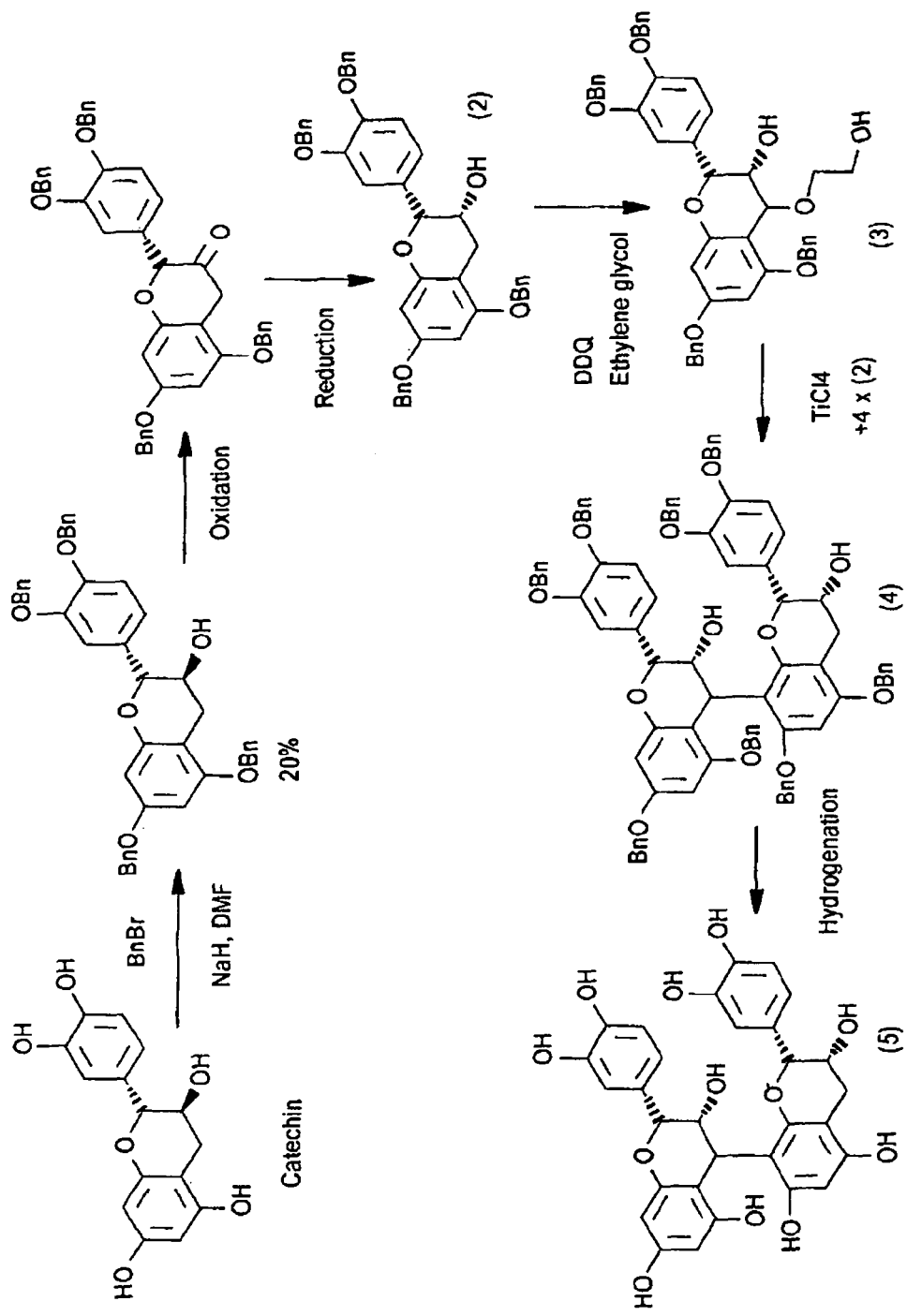
FIG. 1 is a schematic representation of the 6-step synthetic method to produce procyanidin B2, as previously described by Tuckmantel et al (1999).

Unless defined otherwise, all technical and scientific terms used herein have the same meaning as is commonly understood by one of skill in the art to which the disclosure belong. All patents, patent applications, published applications and publications, Genbank sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

Proanthocyanidins are polyphenolic molecules that belong to the flavanoid family of compounds. Proanthocyanidins are also known as proanthocyanins, leucoanthocyanins, anthocyanogens and procyanidins; these terms can be used interchangeably.

"Isolated Procyanidin B2" refers to procyanidin B2 (or epichatechin-4β-8-epicatechin or the epicatechin-dimer or the epicatechin B2 dimer) purified or isolated by the methods disclosed herein.

"Synthetic Procyanidin B2" refers to procyanidin B2 (or epichatechin-4β→8-epicatechin or the epicatechin-dimer or the epicatechin B2 dimer) produced by the methods disclosed herein.

"Epicatechin," as used herein, refers to both unsubstituted and substituted epicatechins. Substituted epicatechins include epicatechins of Formula I, wherein $R_1$ and $R_2$ are independently selected from hydrogen and hydroxyl; $R_3$ is selected from hydrogen, optionally substituted)-glycosyl, C(O)-(optionally substituted aryl), and C(O)-(optionally substituted heteroaryl); and $R_4$ is selected from hydrogen, catechin, epicatechin, epiafzelechin, and gallates of catechin and epicatechin (see, for example, U.S. patent application Ser. No. 10/077,596, published on Jan. 23, 2003 as Publication No. US 2003/0017998). In addition, "epicatechin" is intended to include (+)-epicatechin, (−)-epicatechin, and (±)-epicatechin. 1

"Mammal" and "mammalian subject" includes, but is not limited to, humans and non-human mammals, such as companion animals (cats, dogs, and the like), lab animals (such as mice, rats, guinea pigs, and the like) and farm animals (cattle, horses, sheep, goats, swine, and the like).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts" means salts that are pharmaceutically acceptable and have the desired pharmacological properties. Such salts include salts that can be formed when acidic protons present in the compounds are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, trimethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When there are two acidic groups present, a pharmaceutically acceptable salt can be a mono-acid-mono-salt or a di-salt; and similarly where there are more than two acidic groups present, some or all of such groups can be salified.

A "therapeutically effective amount" in general means the amount that, when administered to a subject or animal for treating a disease, is sufficient to affect the desired degree of treatment for the disease. A "therapeutically effective amount" or a "therapeutically effective dosage" preferably inhibits, reduces, disrupts, and/or disassembles amyloidosis; fibril formation, deposition, accumulation and/or persistence; or a disease associated with α-synuclein/NAC fibril formation in a patient by at least 20%, more preferably by at least 40%, even more preferably by at least 60%, and still more preferably by at least 80%, relative to untreated subjects. A broad range of disclosed composition dosages are believed to be both safe and effective. For example, effective amounts of a proanthocyanidin or procyanidin, or other disclosed compositions for treatment of a mammalian subject are about 1 mg to about 10,000 mg/kg of body weight of the subject, but more preferably from about 10 mg/kg of body weight to 100 mg/kg of body weight.

"Treating" or "treatment" of a disease includes preventing the disease from occurring in a mammal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). "Treating" amyloidosis or "amyloid diseases" includes any one or more of the following: preventing, inhibiting, reducing, disassembling, disrupting, and disaggregating amyloid fibrils and amyloid protein deposits, such as Aβ and the other amyloids referred to herein.

"Treating" an α-synuclein disease or "treating α-synuclein or NAC fibrillogenesis" includes any one or more of the following: preventing, inhibiting, reducing, disassembling, disrupting, and disaggregating α-synuclein/NAC fibrils and α-synuclein/NAC-associated protein deposits, such as those in Lewy body disease, Parkinson's disease and multiple system atrophy.

"NAC" (non-amyloid component) is a 35-amino acid peptide fragment of α-synuclein, which also, like α-synuclein, has the ability to form amyloid-like fibrils when incubated at 37° C., and are positive with amyloid stains such as Congo red (demonstrating a red/green birefringence when viewed under polarized light) and Thioflavin S (demonstrating positive fluorescence) (Hashimoto et al., Brain Res. 799:301-306, 1998; Ueda et al., Proc. Natl. Acad. Sci. U.S.A 90:11282-11286, 1993). Inhibition of NAC fibril formation, deposition, accumulation, aggregation, and/or persistence is believed to be effective treatment for a number of diseases involving α-synuclein, such as Parkinson's disease, Lewy body disease and multiple system atrophy.

"Fibrillogenesis" refers to the presence of amyloid fibrils or fibrils formed containing α-synuclein and/or NAC. Inhibition of such fibrillogenesis with a therapeutic compound can include, but is not limited to, treating, inhibiting, preventing, or managing such amyloid, α-synuclein and/or NAC fibril formation, deposition, accumulation, aggregation and/or persistence in a mammalian subject.

A "pharmaceutical agent" or "pharmacological agent" or "pharmaceutical 13 composition" refers to a compound or combination of compounds used for treatment, preferably in a pure or near pure form. In the specification, pharmaceutical or pharmacological agents include the proanthocyanidins and procyanidins as examples. Disclosed pharmaceutical or pharmacological compounds or compounds in compositions, are preferably purified to 80% homogeneity, and more preferably 90% homogeneity. Compounds and compositions purified to 99.9% homogeneity are believed to be advantageous. As a test or confirmation, a pure compound on HPLC would yield a single sharp-peak band.

The disclosed compounds and compositions can possess one or more chiral centers, and can therefore be produced as individual stereoisomers or as mixtures of stereoisomers, depending on whether individual stereoisomers or mixtures of stereoisomers of the starting materials are used. Unless indicated otherwise, the description or naming of a compound or group of compounds is intended to include both the individual stereoisomers and mixtures (racemic or otherwise) of stereoisomers. Methods for the determination of stereochemistry and the separation of stereoisomers are well known to a person of ordinary skill in the art [see, e.g., the discussion in Chapter 4 of March J: Advanced Organic Chemistry, 4th ed. John Wiley and Sons, New York, N.Y., 1992].

Disclosed compounds for pharmacological or pharmaceutical treatment of an amyloid disease, or for treatment of α-synuclein/NAC fibrillogenesis, will include and not be limited to proanthocyanidins, procyanidins, anthocyanins, condensed tannins, leucoanthocyanidins, leucocyanins, anthocyanogens, epicatechin-catechin polymers or oligomers, flavanoids, flavan-3,4-diols, propelargonidins, and A-type, B-type and C-type procyanidins.

Compositions and compounds containing proanthocyanidin B2 can be prepared in accordance with the present disclosure using standard techniques well known to those skilled in the pharmaceutical art. Such compositions can be administered in dosages and by techniques well known to those skilled in the art taking into consideration such factors as age, sex, weight, and condition of the particular patient, and the route of administration. The compositions can be co-administered or sequentially administered with other potential anti-amyloid agents, or anti-α-synuclein/NAC agents; again taking into consideration such factors as the age, sex, weight and condition of the particular patient, and the route of administration.

Examples of compositions useful to effect the disclosed aims include solid compositions for oral administration such as capsules, tablets, pills, and the like, as well as chewable solid formulations, to which the present disclosure may be well suited; liquid reparations for orifice, e.g., oral, nasal, administration such as suspensions, syrups or elixirs; and preparations for parental, subcutaneous, intradermal, intramuscular or intravenous administration (e.g., injectable administration) such as sterile suspensions or emulsions. The active proanthocyanidin compound can be in admixture with a suitable carrier, diluent, or excipient such as sterile water, physiological saline or the like. The active anti-amyloid compounds of the present disclosure can be provided in lyophilized form for reconstituting, for instance, in isotonic, aqueous, saline buffer.

These compounds can be synthesized, isolated or purified as described in the present disclosure, e.g., compounds or combinations thereof can be substantially pure; for instance, synthesized and then purified to apparent homogeneity. Purity is a relative concept, and the numerous Examples demonstrate isolation of inventive compounds or combinations thereof, as well as purification thereof, such that by the methods exemplified a skilled artisan can obtain a substantially pure compound or combination thereof, or purify them to apparent homogeneity (e.g., purity by HPLC; observation of a single chromatographic peak). As defined herein, a substantially pure compound or combination of compounds is at least about 70% pure, more advantageously at least 80% pure, more preferably greater than 90% pure, e.g., at least 90-95% pure, or even purer such as greater than 95% pure, e.g., 99.99% pure.

Moreover, stereoisomers of the oligomers are encompassed within the scope of the disclosure. The stereochemistry of the substituents on a flavanoid monomer of the oligomer can be described in terms of their relative stereochemistry, "alpha/beta" or "cis/trans", or in the terms of the absolute stereochemistry, R/S. The term "alpha" indicates that the substituent is oriented below the plane of the flavan ring, whereas "beta" indicates that the substituent is oriented above the plane of the ring. The term "cis" indicates that the two substituents are oriented on the same face of the ring, whereas "trans" indicates that the two substituents are oriented on opposite faces of the ring. The terms R and S are used to denote the arrangement of the substituents about a stereogenic or "chiral" center, based on the ranking of the groups according to the atomic number of the atoms directly attached to that stereogenic center. For example, the polyphenol, (+)-catechin, can be defined as (2R,trans)-2-(3',4'-dihydroxyphenyl)-3,4-dihydro-2H-1-benzopy-ran-3,5,7-triol, or as (2R, 3S)-flavan-3,3',4',5,7-pentaol. Interflavan (polyphenol-polyphenol) bonding is often characterized using the relative terms α/β or cis/trans; α/β is used herein to designate the relative stereochemistry of the interflavan bonding.

There are multiple stereochemical linkages between position 4 of a monomer and position 6 and 8 of the adjacent monomer; and the stereochemical linkages between monomeric units is designated as (4α→6) or (4β→6) or (4α→8) or (4β→8) for linear oligomers. When catechin is linked to another catechin or epicatechin, the linkages are advantageously (4α→6) or (4α→8). When epicatechin is linked to catechin or another epicatechin, the linkages are advantageously (4β→6) or (4β→8).

In addition to carbon position 4, a bond to carbon position 2 has alpha or beta stereochemistry, and a bond to carbon position 3 has alpha or beta stereochemistry (e.g., (–)-epicatechin or (+)-catechin).

Disclosed are methods pertaining to the synthesis, isolation and purification of procyanidin B2 and the discovery that isolated, purified and synthesized procyanidin B2 are potent inhibitors of amyloid fibrillogenesis. Methods of synthesis, isolation, purification and use of procyanidin B2 are also disclosed for the therapeutic intervention of Alzheimer's disease, type 2 diabetes, Parkinson's disease, systemic AA amyloidosis and other diseases involving amyloid fibril formation and accumulation, especially methods of isolation and synthesis of procyanidin B2 and related compounds, and to the use of those compounds.

The present methods of synthesis of procyanidin B2 overcome many of the limitations of previously described methods. The methods described herein for the synthesis of procyanidin B2, 1) begin with a different starting material than before (i.e., epicatechin instead of catechin), 2) involve a shorter synthetic route than has been previously described (the new synthetic route is a 5-step synthesis instead of the 6-step synthesis previously described) and 3) provide a 5-fold higher yield of synthesis than was previously described (following the first step the yield is 75% for the methods described herein, compared to 20% for the route previously described; furthermore, the overall yield for the 5-step synthesis described herein is 10%, compared to an overall yield of only ~2% for the synthesis described previously).

It will be understood from the detailed description that the aforementioned list is exemplary and is provided to illustrate the types of compounds that can be prepared by the methods disclosed herein and it is not intended as an exhaustive list of the compounds encompassed by the present disclosure.

Tannins, Flavanoids, Proanthocyanidins, and Procyanidins

Tannins are classically divided into 2 groups. Hydrolysable tannins are esters of phenolic acids and a polyol, usually glucose. The phenolic acids are either gallic acid in gallotannins or other phenolic acids derived from the oxidation of galloyl residues in ellagitannins. Proanthocyanidins, forming the second group of tannins, are far more common in our diet. They are polymers made of elementary flavan-3-ol units. A key feature of proanthocyanidins is that they yield anthocyanidins upon heating in acidic media, hence their name (reviewed in Santos-Buelga and Scalbert, J. Sc. Food Agri. 80:1094-1117, 2000).

Structurally, tannins possess 12-16 phenolic groups and 5-7 aromatic rings per 1000 units of relative molecular mass (E. Haslam, Practical Polyphenoics—from Structure to Molecular Recognition and Physiological Action, Cambridge University Press, Cambridge, 1998). This feature, together with their high molecular weight, clearly makes the tannins and similar phenolic polymers found in processed products, such as red wine or black tea, different both in structure and properties from the low-molecular-weight phenolic acids and monomeric flavanoids. The phenolic polymers, formed by enzymatic and/or chemical transformation of simple flavanols, proanthocyanidins and other phenolic compounds, are called tannin-like compounds.

Proanthocyanidins are polyphenolic molecules occurring naturally in fruits, berries and other plant material. These molecules belong to the flavanoid family of compounds. The flavanoid polyphenolics include the catechins, anthocyanins, and proanthocyanidins. Proanthocyanidins are also known in the art as condensed tannins, leucoanthocyanidins, leucodelphinins, leucocyanins, anthocyanogens, epicatechin-catechin polymers and procyanidins. For a review of procyanidins and proanthocyanidins, see Santos-Buelga and Scalbert, J. Sc. Food Agri. 80:1094-1117, 2000.

Proanthocyanidin polymers or oligomers are known to have varying numbers of flavanoid units, and have been reported for example in Mattice et al, Phytochem. 23:1309-1311, 1984; Czochanska et al, J. C. S. Chem. Comm. 375, 1979; and Jones et al, Photochemistry, 15:1407-1409, 1976. Proanthocyanidin oligomers or polymers useful for the present anti-amyloid activity are comprised of monomeric units of leucoanthocyanidins. Leucoanthocyanidins are generally monomeric flavanoids which include catechins, epicatechins, gallocatechins, galloepicatechins, flavonols, flavan-3,4-diols, leucocyanidins and anthocyanidins. The therapeutically effective proanthocyanidin polymers have from 2 to 20 flavanoid units, and more preferably from 2 to 11 flavanoid units.

Procyanidins, also referred to as proanthocyanidins, are polymeric or oligomeric compounds composed of epicatechin and catechin residues. Disclosed compounds include dimers of epicatechin and catechin residues, and trimers of epicatechin. Catechin and epicatechin residues can be combined in all possible combinations in polymeric procyanidins to molecular weights of up to about 10,000 daltons. Proanthocyanidin polymers are known to have a varying number of flavanoid units. The polymers preferably contain two to fifteen monomeric flavanoid subunits, most preferably two to ten subunits.

Proanthocyanidins are polymeric flavan-3-ols whose elementary units are linked by C—C and occasionally C—O—C bonds. The flavan-3-ol units have the typical C6-C3-C6 flavanoid skeleton. The three rings are distinguished by the letters A, B and C. They differ structurally according to the number of hydroxyl groups on both aromatic rings and the stereochemistry of the asymmetric carbons on the heterocycle. The most common proanthocyanidins in food are procyanidins with a 3',4'-dihydroxy substitution on the B ring and prodelphinidins with a 3',4',5'-trihydroxy substitution. Procyanidins or mixed procyanidins/prodelphinidins are most common in food. Propelargonidins with 4'-hydroxy B-rings are relatively rare in food sources, but notably disclosed herein in the form of epiafzelechin. The three carbons C2, C3, C4 of the flavanol heterocycle are asymmetric and can occur in different configurations. With some very rare exceptions, the configuration of C2 is R. Flavan-3-ol units with the 2S configuration are distinguished by the prefix enantio (ent-). The stereochemistry of the C2-C3 linkage can be either trans (2R,3S) or cis (2R,3R) as in (+)-(gallo)catechin and (−)-epi(gallo)catechin polymers, respectively. The interflavan bond at C4 is always trans with respect to the hydroxy group at C3 (E. Haslam, Practical Polyphenoics—from Structure to Molecular Recognition and Physiological Action, Cambridge University Press, Cambridge, 1998).

The most usual interflavanol linkages are C—C bonds established with the C4 of one flavanoid unit ("extension or upper unit"). Such proanthocyanidins belong to the so-called B-type (dimeric) and C type (trimeric) proanthocyanidins. Compounds with doubly linked units (one C—C and one C—O; "A type linkage") have also been reported in some food sources such as tea leaf, cocoa and cranberry fruits (L J. Porter, Flavans and proanthocyanidins, in The Flavanoids-Advances in Research Since 1986, Ed. by J B Harborne, Chapman and Hall, London, pp. 23-55, 1994). In these A-type proanthocyanidins, an additional ether linkage between the C2 of the upper unit and the oxygen-bearing C7 or C5 of the lower one is formed in addition to the usual C4-C8 or C4-C6 bond.

Initially, oligomeric proanthocyanidins were named by an alpha-numeric system, with a letter A, B or C to describe the type of interflavanol linkage; a number was added to the letter as they were detected (Thompson et al, J. Chem. Soc. Perkins Trans. 1: 1387-1399, 1972). A new nomenclature was later introduced to name an increasing number of new structures, based on that utilized for the polysaccharides (Hemingway et al, J. Chem. Soc. Perkins Trans. 1: 1387-1399, 1972). In this nomenclature, the elementary units of the oligomers are designated with the name of the corresponding flavan-3-ol monomers. The interflavanol linkage and its direction are indicated with an arrow (4→) and its configuration at C4 is described as α or β. In type-A doubly linked proanthocyanidins, both linkages are indicated. It is unnecessary to indicate oxygen in the additional ether bond since it is obvious from the substitution pattern of catechin lower units (L J Porter, in The Flavanoids-Advances in Research since 1980, Ed. by J B Harborne, Chapman and Hall, London, pp. 21-62, 1988). For instance, according to this nomenclature, procyanidin dimer B 1 becomes epicatechin-4β→8-catechin and dimer A2 becomes epicatechin-2β→7, 4β→8-epicatechin.

Flavanol units can bear various acyl or glycosyl substituents. The most common acyl substituent is gallic acid which forms an ester with the hydroxyl n the C3 position, as in tea (Nonaka et al, Chem. Pharmaceutic. Bull. 31:3906-3914, 1983) and wine (Prieur et al, Phytochem. 36:781-784, 1994). Several glycosylated proanthocyanidin oligomers have also 25 been characterized. The sugar is generally linked to the hydroxyl group at the C3 position (Ishimaru et al, Phytochem. 26:1167-1170, 1987; Zhang et al, Phytochem. 27:3277-3280, 1988), but also at the C5 position (Gujer et al, Phytochem. 25:1431-1436, 1986). Although proanthocyanidins heterosides are less frequently reported than other flavanoid glycosides, their occurrence can be underestimated, as sugars are frequently associated with purified proanthocyanidin polymers (Porter et al, Phytochem. 24:567-569, 1985; Mathews et al, J. Agric. Food Chem. 45:1195-1201, 1997). Such variations, and other variations disclosed herein, are included with the scope of disclosure of the disclosed proanthocyanidins.

Methods for the Synthesis of Procyanidin B2

In accordance with the present disclosure, procyanidin B2 is synthesized by the esterification of an epicatechin to form a 5,7,3',4',4''-penta-O-acyl-epicatechin. Suitable acyl groups include acetyl, other short chain acyl groups (for example, $C_1$-$C_6$ (i.e., $C_1$, $C_2$, $C_3$, $C_4$, $C_5$, and $C_6$) acyl groups), benzoyl and substituted benzoyl groups. The 5,7,3',4',3''-penta-O-acyl-epicatechin is then protected to form a 5,7,3',4'-tetra-O-protected epicatechin. Suitable protecting groups include benzyl and substituted benzyl groups. An adduct precursor is then coupled with a first portion of the 5,7,3',4'-tetra-O-protected epicatechin to form a 4''-substituted, 5,7,3',4'-tetra-O-protected epicatechin. Suitable adduct precursors include C.sub.1-C.sub.6 alkanols, ethylene glycol, other alcohols including water, and thiols. A second portion of the 5,7,3',4'-tetra-O-protected epicatechin is dimerized with the 4''-substituted, 5,7,3',4'-tetra-O-protected epicatechin to form a 5,7,3',4'-tetra-O-protected epicatechin-4β→8-5,7,3',4'-tetra-O-protected epicatechin. The dimerized 5,7,3',4'-tetra-O-protected epicatechin-4β→8-5,7,3',4'-tetra-O-protected epicatechin can then be deprotected to form procyanidin B2.

In one particular embodiment, esterification produces a pentaacetylated epicatechin.

Acetylation of epicatechin under normal conditions (i.e., acetic anhydride in pyridine) gives an 87% yield of the epicatechin pentaacetate. Treatment of this pentaacetate under typical benzylation conditions (8.0 equivalents of benzyl chloride with at least 10 equivalents of sodium hydride in dimethylformamide for 24 hours at room temperature) leads to benzylation. However, whereas the reported benzylation of catechin using this method yields mostly a tetrabenzlyated product (Kawamoto et al, Synthetic Comm. 26(3):531-534, 1996), starting with epicatechin as described in the present disclosure predominantly leads to the generation of a pentabenzylated product. Shortening the reaction time, to between about 1 hour and about 3 hours, gives the desired tetrabenzylated product in about 40% yield, together with under and over benzylated by-products. Using between about 4.0 and about 4.2 equivalents of benzyl chloride (e.g., about 4.1 equivalents of benzyl chloride) and a longer reaction time (e.g., a reaction time of between about 24 hours and about 72 hours), a much higher 75% yield of the tetrabenzlyated product was obtained. The previous study by Tuckmantel generated a tetrabenzylated product from catechin starting materials, but with only a 20% yield. Using the synthetic methods disclosed herein, 10-20% of the reaction product epimerises at C-3, but this problem is circumvented by altering the reaction work-up conditions, such as by pouring the reaction mixture onto ice cold 1M hydrochloric acid, and leading to the generation of the tetrabenzyl-epicatechin intermediate (2) in 75% yield. It should be noted that under these reaction conditions the acetate group on C-3 is hydrolyzed to the 3-hydroxyl group.

Figure 9:
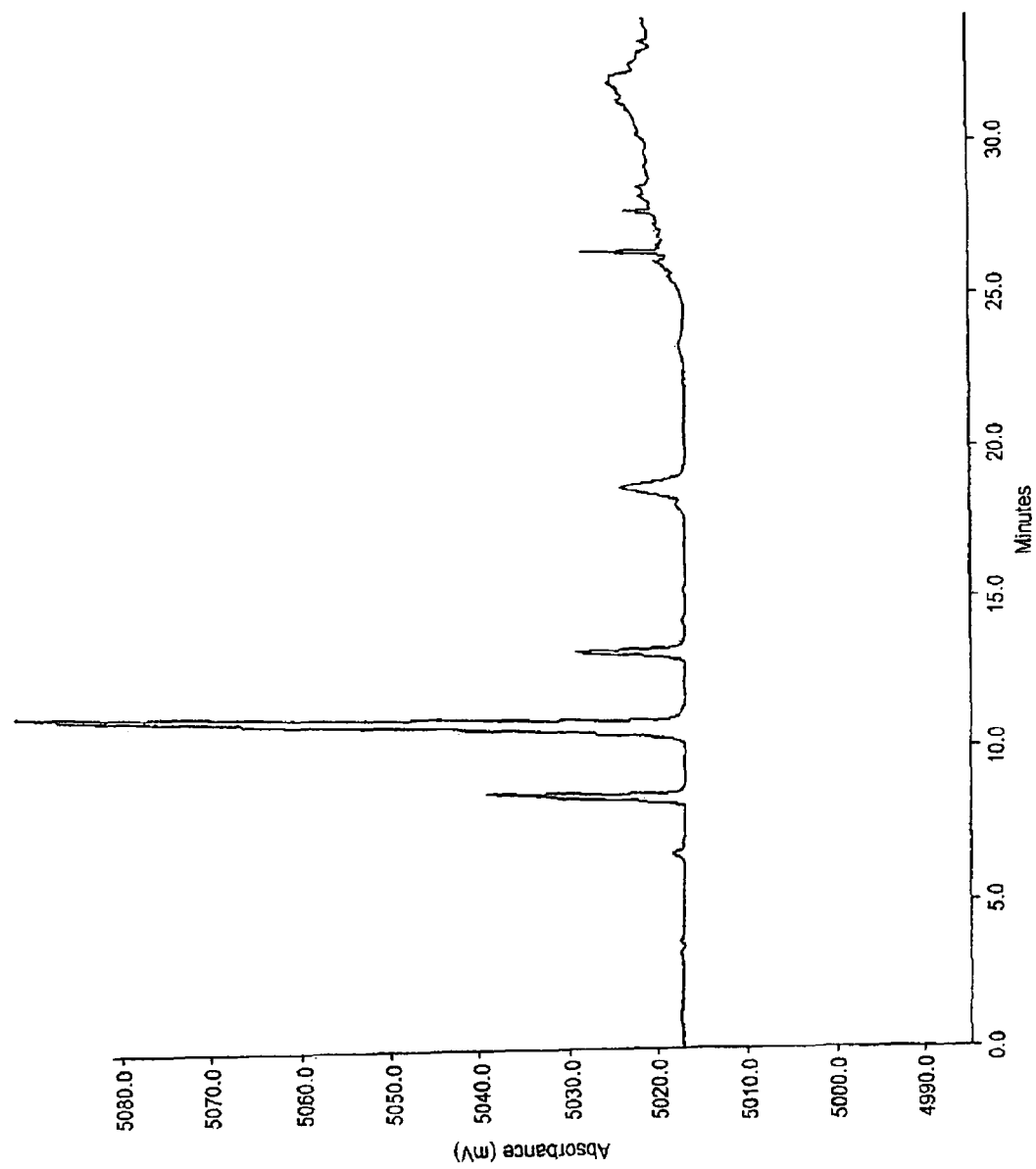
FIG. 9 is an HPLC tracing of procyanidin B2 (main peak at 10.3 minutes), following step 5 of the synthetic route of FIG. 2. Eighty percent (80%) of the procyanidin B2 was observed with small amounts of epicatechin at 12.4 minutes, and the procyanidin trimer C1 at 17.6 minutes.
Figure 10:
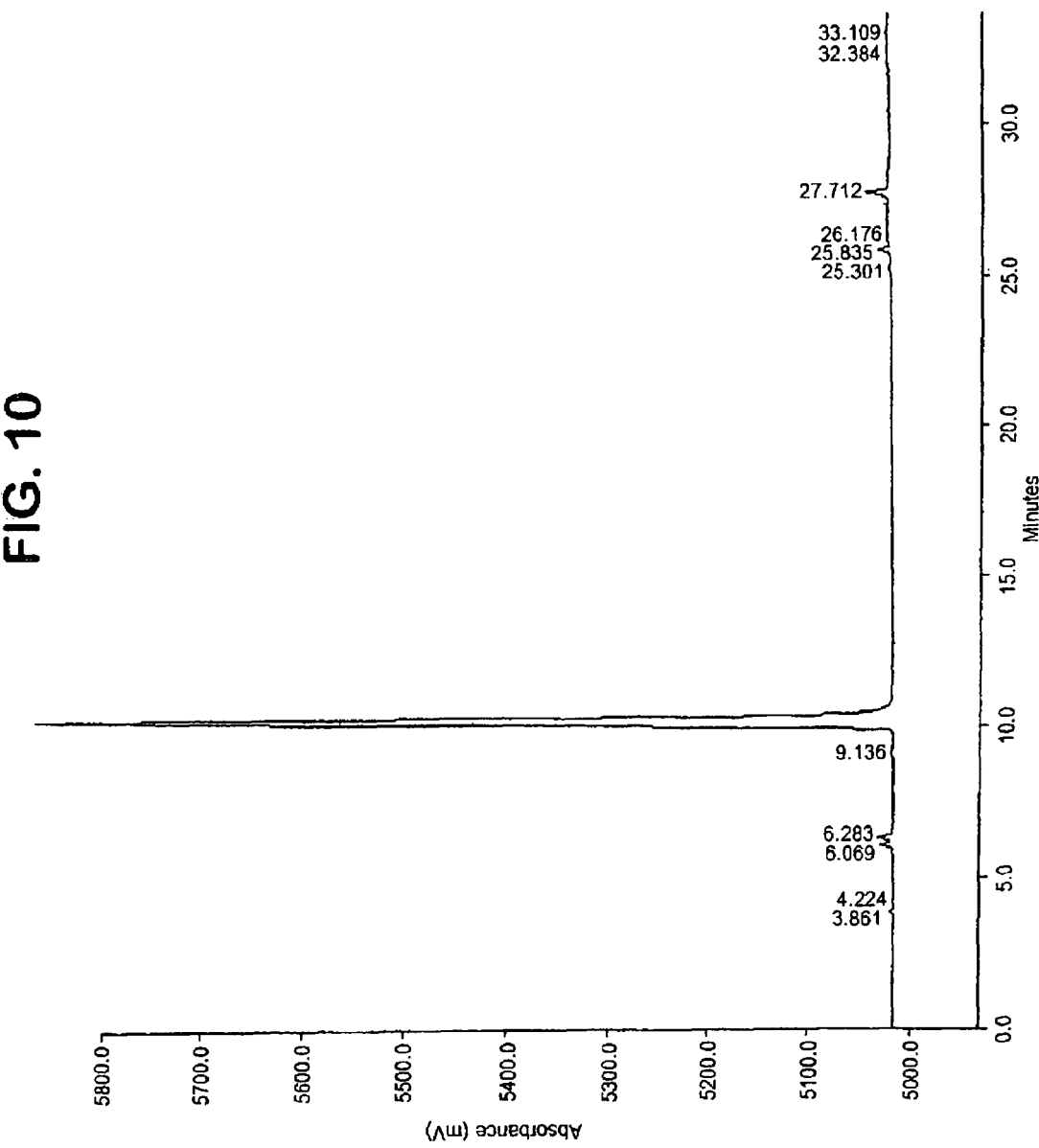
FIG. 10 is an HPLC tracing of procyanidin B2 following the synthetic route of FIG. 2, and final purification by LH20 column chromatography.

Coupling of the ethylene glycol adduct with a four-fold excess of tetrabenzyl-epicatechin using titanium tetrachloride (step 4, FIG. 2) gives a 39% yield of the protected dimer. Modification of the published workup procedure by first removing the excess reactant by crystallization, then separation of the mother liquor by column chromatography, unexpectedly dramatically improves the isolation of the protected dimer (4). Deprotection by conventional hydrogenolysis of the benzyl groups leads to the generation of the procyanidin B2 product (5). Some degree of disproportionation is observed, with the presence of monomeric epicatechin and the trimer procyanidin C1 being detected in the HPLC chromatogram of the crude product (FIG. 9). The free dimer procyanidin B2 is then optionally purified by column chromatography over Sephadex LH20 chromatography in a 50% yield, to give the pure procyanidin B2 dimer (FIG. 10).

To summarize, the synthetic methods for the production of procyanidin B2 disclosed herein differ from previous synthetic methods (Tuckmantel et al, J. Am. Chem. Soc. 121: 12073-12081, 1999) at least as follows:

1) the methods disclosed herein for the production of procyanidin B2 begins with epicatechin as the starting material, whereas the prior art method employed catechin as the starting material;

2) the methods disclosed herein for the production of procyanidin B2, following step 1, forms a pentaacylated product, whereas the prior art method did not produce a pentaacylated product but primarily a tetrabenzylated product;

3) the methods disclosed herein for the production of procyanidin B2 leads to the formation of synthesized 5,7,3',4'-tetra-O-benzylepicatechin in 75% yield from commercially available epicatechin in two steps, whereas the prior art method produced this product in only 20% yield from catechin and took three steps;

4) the methods disclosed herein for the production of procyanidin B2, in step 1, includes pouring the reaction mixture onto ice-cold 1M hydrochloric acid, whereas the prior art method did not employ this step and primarily used oxidation/reduction reactions to form the tetrabenzylated product;

5) the methods disclosed herein for the production of procyanidin B2, in step 4, includes removing excess reactant by crystallization, then purifying the dimer by silica gel column chromatography, whereas the prior art method did not use this methodology; and 6) the methods disclosed herein for the production of procyanidin B2 gives an overall 5-fold increase in yield of procyanidin B2 (i.e., 10%) as compared to the prior art method (only ~2%).

Methods for the Isolation of Procyanidin B2

In accordance with the present disclosure, procyanidin B2 is isolated by extracting a sample of bark powder from plant matter of the genus *Uncaria* with an alcohol to form an extract. Suitable alcohols include $C_1$-$C_6$ alcohols such as, for example, methanol, ethanol and propanol; water; acetone; and ethyl acetate The extract is fractionated using flash vacuum fractionation to form a plurality of flash vacuum fractions. The flash vacuum fractions are analyzed to determine the flash vacuum fractions comprising procyanidin B2. At least one of the flash vacuum fractions comprising procyanidin B2 is then fractionated using silica gel column chromatography to form a plurality of silica gel fractions. The silica gel fractions are then analyzed to determine the silica gel fractions comprising procyanidin B2. At least one of the silica gel fractions comprising procyanidin B2 is fractionated using Sephadex LH20 column chromatography to form a plurality of Sephadex LH20 fractions. The Sephadex LH20 fractions are optionally analyzed to determine the Sephadex LH20 fractions comprising procyanidin B2. Suitable methods for analyzing the fractions include thin layer chromatography (TLC), low and high pressure liquid chromatography (HPLC), electrospray (ES) mass spectrometry (MS), and nuclear magnetic resonance (NMR; e.g., $^1$H and $^{13}$C), either alone or in combination.

Amyloid and Amyloidosis

Amyloid is a generic term referring to a group of diverse but specific extracellular protein deposits which all have common morphological properties, staining characteristics, and X-ray diffraction spectra. Regardless of the nature of the amyloid protein deposited, all amyloids have the following characteristics: 1) showing an amorphous appearance at the light microscopic level, appearing eosinophilic using hematoxylin and eosin stains; 2) staining with Congo red and demonstrating a red/green birefringence as viewed under polarized light (Puchtler et al., J. Histochem. Cytochem. 10:355-364, 1962), 3) containing a predominant beta-pleated sheet secondary structure, and 4) ultrastructurally consisting of non-branching fibrils of indefinite length and with a diameter of 7-10 nm.

Amyloidoses and "amyloid diseases" today are classified according to the specific amyloid protein deposited. The amyloids include, but are not limited to, the amyloid associated with Alzheimer's disease, Down's syndrome, hereditary cerebral hemorrhage with amyloidosis of the Dutch type and inclusion body myositosis (where the specific amyloid is referred to as beta-amyloid protein or Aβ), the amyloid associated with chronic inflammation, various forms of malignancy and familial Mediterranean fever (where the specific amyloid is referred to as AA amyloid or inflammation-associated amyloid), the amyloid associated with multiple myeloma and other B-cell dyscrasias (where the specific amyloid is referred to as AL amyloid), the amyloid associated with type 2 diabetes (where the specific amyloid is referred to as amylin or islet amyloid), the amyloid associated with the prion diseases including Creutzfeldt-Jakob disease, Gerstmann-Straussler syndrome, kuru, and scrapie (where the specific amyloid is referred to as PrP amyloid), the amyloid associated with long-term hemodialysis and carpal tunnel syndrome (where the specific amyloid is referred to as $0_2$-microglobulin amyloid), the amyloid associated with senile cardiac amyloid and familial amyloidotic polyneuropathy (where the specific amyloid is referred to as prealbumin or transthyretin amyloid), and the amyloid associated with endocrine tumors such as medullary carcinoma of the thyroid (where the specific amyloid is referred to as variants of procalcitonin).

Although amyloid deposits in clinical conditions share common physical properties relating to the presence of a beta-pleated sheet conformation, it is now clear that many different chemical types exist and additional ones are likely to be described in the future. It is currently thought that there are several common pathogenetic mechanisms that can be operating in amyloidosis in general. In many cases, a circulating precursor protein can result from overproduction of either intact or aberrant molecules (for example, in plasma cell dyscrasias), reduced degradation or excretion (serum amyloid A in some secondary amyloid syndromes and beta.sub.2-microglobulin in long-term hemodialysis), or genetic abnormalities associated with variant proteins (for example, familial amyloidotic polyneuropathy). Proteolysis of a larger protein precursor molecule occurs in many types of amyloidosis, resulting in the production of lower molecular weight fragments that polymerize and assume a beta-pleated sheet conformation as tissue deposits, usually in an extracellular location. The precise mechanisms involved and the aberrant causes leading to changes in proteolytic processing and/or translational modification are not known in most amyloids.

Systemic amyloid diseases which include the amyloid associated with chronic inflammation, various forms of malignancy and familial Mediterranean fever (i.e., AA amyloid or inflammation-associated amyloidosis) (Benson and Cohen, Arth. Rheum 22:36-42, 1979; Kamei et al, Acta Path. Jpn. 32:123-133, 1982; McAdam et al., Lancet 2:572-573, 1975; Metaxas, Kidney Int. 20:676-685, 1981), and the amyloid associated with multiple myeloma and other B-cell dyscrasias (i.e., AL amyloid) (Harada et al., J. Histochem. Cytochem. 19:1-15, 1971), as examples, are known to involve amyloid deposition in a variety of different organs and tissues generally lying outside the central nervous system. Amyloid deposition in these diseases can occur, for example, in liver, heart, spleen, gastrointestinal tract, kidney, skin, and/or lungs (Johnson et al, N. Engl. J. Med. 321:513-518, 1989). For most of these amyloidoses, there is no apparent cure or effective treatment and the consequences of amyloid deposition can be detrimental to the patient. For example, amyloid deposition in the kidney can lead to renal failure, whereas amyloid deposition in the heart can lead to heart failure. For these patients, amyloid accumulation in systemic organs leads to eventual death generally within 3-5 years. Other amyloidoses can affect a single organ or tissue such as observed with the A$\beta$ amyloid deposits found in the brains of patients with Alzheimer's disease and Down's syndrome; the PrP amyloid deposits found in the brains of patients with Creutzfeldt-Jakob disease, Gerstmann-Straussler syndrome, and kuru; the islet amyloid (amylin) deposits found in the islets of Langerhans in the pancreas of 90% of patients with type II diabetes (Johnson et al, N. Engl. J. Med. 321:513-518, 1989; Lab. Invest. 66:522 535, 1992); the $\beta_2$-microglobulin amyloid deposits in the medial nerve leading to carpal tunnel syndrome as observed in patients undergoing long-term hemodialysis (Geyjo et al, Biochem. Biophys. Res. Comm. 129: 701-706, 1985; Kidney Int. 30:385-390, 1986); the prealbumin/transthyretin amyloid observed in the hearts of patients with senile cardiac amyloid; and the prealbumin/transthyretin amyloid observed in peripheral nerves of patients who have familial amyloidotic polyneuropathy (Skinner and Cohen, Biochem. Biophys. Res. Comm 99:1326-1332, 1981; Saraiva et al, J. Lab. Clin. Med. 102: 590-603, 1983; J. Clin. Invest. 74:104-119, 1984; Tawara et al, J. Lab. Clin. Med. 98:811-822, 1989).

Alzheimer's Disease and the Aging Population

Alzheimer's disease is a leading cause of dementia in the elderly, affecting 5-10% of the population over the age of 65 years (A Guide to Understanding Alzheimer's Disease and Related Disorders, Jorm, ed., New York University Press, New York, 1987). In Alzheimer's disease, the parts of the brain essential for cognitive processes such as memory, attention, language, and reasoning degenerate, robbing victims of much that makes us human, including independence. In some inherited forms of Alzheimer's disease, onset is in middle age, but more commonly, symptoms appear from the mid-60's onward. Alzheimer's disease today affects 4-5 million Americans, with slightly more than half of these people receiving care at home, while the others are in many different health care institutions. The prevalence of Alzheimer's disease and other dementias doubles every 5 years beyond the age of 65, and recent studies indicate that nearly 50% of all people age 85 and older have symptoms of Alzheimer's disease (2000 Progress Report on Alzheimer's Disease, National Institute on Aging/National Institute of Health). In addition, 13% (33 million people) of the total population of the United States are age 65 and older, and this percentage will climb to 20% by the year 2025 (2000 Progress Report on Alzheimer's Disease).

Alzheimer's disease also puts a heavy economic burden on society. A recent study estimated that the cost of caring for one Alzheimer's disease patient with severe cognitive impairments, at home or in a nursing home, is more than $47,000 per year (A Guide to Understanding Alzheimer's Disease and Related Disorders). For a disease that can span from 2 to 20 years, the overall cost of Alzheimer's disease to families and to society is staggering. The annual economic toll of Alzheimer's disease in the United States in terms of health care expenses and lost wages of both patients and their caregivers is estimated at $80 to $100 billion (2000 Progress Report on Alzheimer's Disease). Therefore, it is clear that there is a need for more effective treatments for Alzheimer's disease patients.

Amyloid as a Therapeutic Target for Alzheimer's Disease

Alzheimer's disease is characterized by the deposition and accumulation of a 39-43 amino acid peptide termed the beta-amyloid protein, A$\beta$ or $\beta$/A4 (Glenner and Wong, Biochem. Biophys. Res. Comm. 120:885-890, 1984; Masters et al., Proc. Natl. Acad. Sci. USA 82:4245-4249, 1985; Husby et al., Bull. WHO 71:105-108, 1993). A$\beta$ is derived by protease cleavage from larger precursor proteins termed beta-amyloid precursor proteins (or $\beta$PPs) of which there are several alternatively spliced variants. The most abundant forms of the $\beta$PPs include proteins consisting of 695, 751 and 770 amino acids (Tanzi et al., Nature 331:528-530, 1988; Kitaguchi et al., Nature 331:530-532, 1988; Ponte et al., Nature 331:525-527, 1988).

The small A$\beta$ peptide is a major component which makes up the amyloid deposits of "plaques" in the brains of patients with Alzheimer's disease. In addition, Alzheimer's disease is characterized by the presence of numerous neurofibrillary "tangles," consisting of paired helical filaments which abnormally accumulate in the neuronal cytoplasm (Grundke-Iqbal et al., Proc. Natl. Acad. Sci. USA 83:4913-4917, 1986; Kosik et al., Proc. Natl. Acad. Sci. USA 83:4044-4048, 1986; Lee et al., Science 251:675-678, 1991). The pathological hallmark of Alzheimer's disease is therefore the presence of "plaques" and "tangles", with amyloid being deposited in the central core of the plaques. The other major type of lesion found in the Alzheimer's disease brain is the accumulation of amyloid in the walls of blood vessels, both within the brain parenchyma and in the walls of meningeal vessels that lie outside the brain. The amyloid deposits localized to the walls of blood vessels are referred to as cerebrovascular amyloid or congophilic angiopathy (Mandybur, J. Neuropath. Exp. Neurol. 45:79-90, 1986; Pardridge et al., J. Neurochem. 49:1394-1401, 1987).

For many years, there has been an ongoing scientific debate as to the importance of "amyloid" in Alzheimer's disease, and whether the "plaques" and "tangles" characteristic of this disease were a cause or merely a consequence of the disease. Within the last few years, studies now indicate that amyloid is indeed a causative factor for Alzheimer's disease and should not be regarded as merely an innocent bystander. The Alzheimer's A$\beta$ protein in cell culture has been shown to cause degeneration of nerve cells within short periods of time (Pike et al., Br. Res. 563:311-314, 1991; J. Neurochem. 64:253-265, 1995). Studies suggest that it is the fibrillar structure (consisting of a predominant beta-pleated sheet secondary structure), characteristic of all amyloids, that is responsible for the neurotoxic effects. A$\beta$ has also been found to be neurotoxic in slice cultures of hippocampus (Harrigan et al., Neurobiol. Aging 16:779-789, 1995) and induces nerve cell death in transgenic mice (Games et al., Nature 373:523-527, 1995; Hsiao et al., Science 274:99-102, 1996). Injection of the Alzheimer's A$\beta$ into rat brain also causes memory impairment and neuronal dysfunction Flood et al., Proc. Natl. Acad. Sci. USA 88:3363-3366, 1991; Br. Res. 663:271-276, 1994).

Probably, the most convincing evidence that A$\beta$ amyloid is directly involved in the pathogenesis of Alzheimer's disease comes from genetic studies. It has been discovered that the production of Aβ can result from mutations in the gene encoding its precursor, beta amyloid precursor protein (Van Broeckhoven et al., Science 248:1120-1122, 1990; Murrell et al., Science 254:97-99, 1991; Haass et al., Nature Med. 1:1291-1296, 1995). The identification of mutations in the beta-amyloid precursor protein gene which causes early onset familial Alzheimer's disease is the strongest argument that amyloid is central to the pathogenetic process underlying this disease. Four reported disease-causing mutations have now been discovered which demonstrate the importance of Aβ in causing familial Alzheimer's disease (reviewed in Hardy, Nature Genet. 1:233-234, 1992). All of these studies suggest that providing a drug to reduce, eliminate or prevent fibrillar Aβ formation, deposition, accumulation and/or persistence in the brains of human patients will serve as an effective therapeutic.

Parkinson's Disease and α-Synuclein Fibril Formation

Parkinson's disease is a neurodegenerative disorder that is pathologically characterized by the presence of intracytoplasmic Lewy bodies (Lewy in Handbuch der Neurologie, M. Lewandowski, ed., Springer, Berlin, pp. 920-933, 1912; Pollanen et al., J. Neuropath. Exp. Neurol. 52:183-191, 1993), the major components of which are filaments consisting of α-synuclein (Spillantini et al., Proc. Natl. Acad. Sci. USA-.sub.—95:6469-6473, 1998; Arai et al., Neurosc. Lett. 259: 83-86, 1999), a 140-amino acid protein (Ueda et al., Proc. Natl. Acad. Sci. U.S.A. 90:11282-11286, 1993). Two dominant mutations in α-synuclein causing familial early onset Parkinson's disease have been described suggesting that Lewy bodies contribute mechanistically to the degeneration of neurons in Parkinson's disease (Polymeropoulos et al., Science 276:2045-2047, 1997; Kruger et al., Nature Genet. 18:106-108, 1998). Recently, in vitro studies have demonstrated that recombinant α-synuclein can indeed form Lewy body-like fibrils (Conway et al., Nature Med. 4:1318-1320, 1998; Hashimoto et al., Brain Res. 799:301-306, 1998; Nahri et al., J. Biol. Chem. 274:9843-9846, 1999). Most importantly, both Parkinson's disease-linked α-synuclein mutations accelerate this aggregation process that suggests that such in vitro studies can have relevance for Parkinson's disease pathogenesis.

α-Synuclein aggregation and fibril formation fulfills the criteria of a nucleation-dependent polymerization process (Wood et al., J. Biol. Chem. 274:19509-19512, 1999). In this regard, α-synuclein fibril formation resembles that of Alzheimer's beta-amyloid protein (Aβ) fibrils. α-Synuclein recombinant protein and non-amyloid component (known as NAC), which is a 35-amino acid peptide fragment of α-synuclein, both have the ability to form fibrils when incubated at 37° C., and are positive with amyloid stains such as Congo red (demonstrating a red/green birefringence when viewed under polarized light) and Thioflavin S (demonstrating positive fluorescence) (Hashimoto et al., Brain Res. 799:301-306, 1998; Ueda et al., Proc. Natl. Acad. Sci. U.S.A 90:11282-11286, 1993).

In addition, accumulation of α-synuclein/NAC is also a cytopathological feature common to Lewy body disease and multiple system atrophy (Wakabayashi et al, Acta Neuropath. 96:445-452, 1998; Piao et al, Acta Neuropath. 101:285-293, 2001). Multiple system atrophy is a sporadic neurodegenerative disease in adults characterized by neuronal and glial cytoplasmic inclusions, containing α-synuclein/NAC.

Parkinson's disease α-synuclein/NAC fibrils, like the Aβ fibrils of Alzheimer's disease, also consist of a predominant beta-pleated sheet structure. It is therefore believed that compounds found to inhibit Alzheimer's disease Aβ amyloid fibril formation can also be anticipated to be effective in the inhibition of α-synuclein and/or NAC fibril formation. These compounds would therefore also serve as therapeutics for Parkinson's disease, in addition to having efficacy as a therapeutic for Alzheimer's disease and other amyloid disorders.

Islet Amyloid Polypeptide (IAPP) and Type 2 Diabetes

Islet amyloid deposits are observed in ~90% of patients with well-established type 2 diabetes and would appear to be a characteristic feature of the disease process (Westermark, J. Med. Sci. 77:91-94, 1972; Clark et al, Diabetes Res. 9:151-159, 1988). In many patients, the deposits are widespread and affect many islets. The degree of islet (predominantly β-cell) mass that has been replaced by amyloid can be a marker for the severity of the diabetic disease process, with those individuals requiring insulin treatment having the greatest islet mass reduction and amyloid formation (Westermark, Amyloid: Int. J. Exp. Clin. Invest. 1:47-60, 1994). Since islet amyloid has been observed in autopsy samples obtained from different populations, it appears to be a phenomenon common to the disease rather than to a subpopulation of individuals with the syndrome (Westermark, J. Med. Sci. 77:91-94, 1972; Clark et al, Diabetes Res. 9:151-159, 1988). The prevalence of islet amyloid deposits increases with age (Bell, Am. J. Path. 35:801-805, 1959), which is not surprising because normal aging is associated with a deterioration in glucose tolerance and an increased prevalence of type 2 diabetes (Davidson, Metabolism 28:687-705, 1979).

The major protein in islet amyloid is a 37-amino acid peptide known as islet amyloid polypeptide (IAPP) or amylin. IAPP is a known normal secretory product of the pancreatic β-cells (Kanh et al, Diabetes 39:634-638, 1990) that is stored in insulin-bearing cytoplasmic granules (Clark et al, Cell Tissue Res. 257:179-185, 1989). It has long been questioned whether the deposition of islet amyloid is involved in, or merely a consequence of, the pathogenesis of type 2 diabetes. However, a number of studies now suggest that, in fact, islet amyloid formation, deposition and persistence can be an important primary factor leading to β-cell dysfunction and cell death, hyperglycemia, and in the development of type 2 diabetes.

IAPP has been hypothesized to have an important role in the pathogenesis of type 2 diabetes through its impairment of B-cell function and reduction of β-cell mass (Johnson et al, N. Engl. J. Med. 321:513-518, 1989). Besides being able to form islet amyloid deposits that replace β-cell mass, amyloid fibrils appear to damage islets directly. Studies in which islets were incubated in the presence of human or rat IAPP demonstrated that human IAPP formed amyloid fibrils in a concentration-dependent manner and was associated with the death of pancreatic islet β-cells (Lorenzo et al, Nature 368:756-760, 1994). Cell death did not occur in the presence of rat IAPP that does not form amyloid fibrils (Lorenzo et al, Nature 368:756-760, 1994).

Studies involving transgenic mouse models have allowed further insight into the role of islet amyloid in the pathogenesis of type 2 diabetes. More recent studies do suggest that development of IAPP-derived islet amyloid does not depend on hyperglycemia and is progressive (Verchere et al, Proc. Natl. Acad. Sci. U.S.A. 93:3492-3496, 1996). In these latter studies, hyperglycemia developed in only 31% of male transgenic mice and in 14% of male nontransgenic animals. When pancreatic sections from these mice were examined, islet amyloid was found in every transgenic mouse with diabetes. However, two-thirds of male transgenic animals that were normoglycemic also developed islet amyloid deposits indicating that hyperglycemia was not a prerequisite for islet amyloid formation. The data from these and other studies further suggested that human IAPP fibrils can be cytotoxic to β-cells and thus could produce early alterations in islet function (Lorenzo et al, Nature 368:756-760, 1994; Janson et al, Diabetes 47:A250, 1998). Islet amyloid deposition appears to be an early feature of the islet lesion of type 2 diabetes and progressive accumulation of islet amyloid is associated with further β-cell mass reduction (Clark et al, Diabetes Res. 9:151-159, 1988; Westermark and Wilander, Diabetologia 15:417-421, 1978). Thus, a progressive reduction in islet mass caused by increased amyloid deposition is associated with a progressive impairment in insulin secretion, reduction in glucose tolerance, and eventually the development of fasting hyperglycemia. The studies in transgenic animals suggest not just that hyperglycemia is associated with the development of islet amyloid, but that amyloid contributes to the development of hyperglycemia by replacing β-cells. These studies as a whole suggest that islet amyloid formation plays a central role in the development of β-cell failure of type 2 diabetes. Therefore, agents or compounds able to inhibit or disrupt islet amyloid (i.e., IAPP or amylin) formation, deposition, accumulation or persistence can lead to new potential treatments for type 2 diabetes.

Pharmacology and Utility

The disclosed procyanidin B2 compounds act to inhibit or prevent amyloid fibril formation, inhibit or prevent amyloid fibril growth, and/or cause disassembly, disruption, and/or disaggregation of preformed amyloid fibrils and amyloid protein deposits. Their activity can be measured in vitro by methods such as those discussed in Examples 7-9, 14 and 15, while their activity in vivo against amyloidoses can be measured in animal models, such as those of Alzheimer's disease, and in humans by a method such as that disclosed in Example 9.

The amyloid diseases also include, but are not limited to, the amyloid associated with Down's syndrome, hereditary cerebral hemorrhage with amyloidosis of the Dutch type, and inclusion body myositosis (Askanas et al, Ann. Neurol. 43:521-560, 1993) (wherein the specific amyloid is referred to as beta-amyloid protein or Aβ), the amyloid associated with chronic inflammation, various forms of malignancy and Familial Mediterranean Fever (wherein the specific amyloid is referred to as AA amyloid or inflammation-associated amyloidosis), the amyloid associated with multiple myeloma and other B-cell dyscrasias (wherein the specific amyloid is referred to as AL amyloid), the amyloid associated with type II diabetes (wherein the specific amyloid protein is referred to as amylin or islet amyloid polypeptide), the amyloid associated with the prion diseases including Creutzfeldt-Jakob disease, Gerstmann-Straussler syndrome, kuru and animal scrapie (wherein the specific amyloid is referred to as PrP amyloid), the amyloid associated with long-term hemodialysis and carpal tunnel syndrome (wherein the specific amyloid is referred to as $\beta_2$-microglobulin amyloid), the amyloid associated with senile cardiac amyloid and Familial Amyloidotic Polyneuropathy (wherein the specific amyloid is referred to as transthyretin or prealbumin), and the amyloid associated with endocrine tumors such as medullary carcinoma of the thyroid (wherein the specific amyloid is referred to as variants of procalcitonin). In addition, the α-synuclein protein which forms fibrils, and is Congo red and Thioflavin S positive, is found as part of Lewy bodies in the brains of patients with Parkinson's disease, Lewy body disease (Lewy in Handbuch der Neurologie, M. Lewandowski, ed., Springer, Berline pp. 920-933, 1912; Pollanen et al, J. Neuropath. Exp. Neurol. 52:183-191, 1993; Spillantini et al, Proc. Natl. Acad. Sci. USA 95:6469-6473, 1998; Arai et al, Neurosc. Lett. 259:83-86, 1999), and multiple system atrophy (Wakabayashi et al, Acta Neuropath. 96:445-452, 1998). For purposes of this disclosure, Parkinson's disease, due to the fact that fibrils develop in the brains of patients with this disease (which are Congo red and Thioflavin S positive, and which contain predominant beta-pleated sheet secondary structure), should be regarded as a disease that also displays the characteristics of an amyloid-like disease.

Specific procyanidins or proanthocyanidins are effective agents to disrupt/cause disassembly of amyloid and α-synuclein fibrils for a variety of amyloidoses including Alzheimer's and Parkinson's disease. One of the procyanidins, namely procyanidin B2 (also referred to as epicatechin-4β→8-epicatechin) is very effective as an inhibitor of Aβ (i.e., beta-amyloid protein) and α-synuclein fibrillogenesis. However, the procyanidin B2 used was not commercially available and had to be isolated from plant material by a method that required a lot of raw material and a long time to complete. Furthermore, the only published method available to synthesize procyanidin B2 (Tuckmantel et al, J. Am. Chem. Soc., 121:12073-12081, 1999) had a very low yield (~2% of starting materials), and therefore required a great amount of starting material (i.e., catechin) to produce substantial quantities (gram to kilograms) of procyanidin B2.

In order to circumvent these problems and in order to produce increased production of procyanidin B2 as a potential new therapeutic for the treatment of Alzheimer's, Parkinson's and other amyloid disorders, a quick and more efficient isolation method for the production of procyanidin B2 was needed. Provided herein are new methods of isolation of procyanidin B2 from plant material, and more specifically, from *Uncaria tomentosa* (i.e., cat's claw). In addition, provided herein are new methods of synthesis of procyanidin B2. Provided herein is a synthetic route to procyanidin B2 which is different from that previously described in that the synthetic route provided herein, 1) begins with a different starting material than before (i.e., epicatechin instead of catechin), 2) is a shorter synthetic route than has been previously described, and 3) provides a higher yield of synthesis that was previously described.

*Uncaria tomentosa* (Cat's Claw)

The herb *Uncaria tomentosa*, also known as "Una de Gato" (in Spanish) or "Cat's claw" (in English) refers to a woody vine that grows within the Peruvian Amazon rain forest. This slow growing vine takes 20 years to reach maturity, and can grow over 100 feet in length as it attaches and wraps itself around the native trees. It is found abundantly in the foothills, at elevations of two to eight thousand feet. The vine is referred to as "Cat's claw" because of its distinctive curved claw-like thorns that project from the base of its leaves.

Provided herein are *Uncaria tomentosa* derived compounds, including procyanidins and proanthocyanidins, for the treatment of amyloidosis associated with Alzheimer's disease, type 2 diabetes, systemic AA amyloidosis, and other amyloid diseases, as well as for the treatment of α-synuclein/NAC fibril formation and accumulation, such as that observed in patients with Parkinson's disease.

Methods Previously Used to Synthesize Procyanidin B2

The earliest synthetic routes towards the procyanidins in general, and procyanidin B2 in particular, were mostly of low yield, and were mainly designed to obtain small amounts to confirm the structures. Later work found that more efficient formation of a dimer could be obtained from treating an epicatechin polymer (e.g., from *Photinia glabrescens*) with an excess of epicatechin and acid (Hemingway et al, J. C. S. Perkin 1: 1209-1216, 1982). In another adaptation of the same methodology, it was found that an even more efficient reaction could be obtained by treating the preformed thiol ether of epicatechin (formed from the polymer) with an excess of epicatechin in acid (Fletcher et al, J. C. S. Perkin 1: 1628-1637, 1977; Steynberg, Tetrahedron 54:8153-8158, 1998). These methods relied on the supply of crude epicatechin or catechin polymer, and required the use of tedious separation techniques to purify the products.

There have been some synthetic approaches to procyanidins made from simple phloroglucinol derived starting materials (Steynberg, Tetrahedron 54:8153-8158, 1998; Nay et al, J. Org. Chem. 2379-2384, 2001; Arnaudinaud, Tetrahedron Letters 42:5669-5671, 2001). These approaches all require the often lengthy and sometimes inefficient use of an optical resolution step to obtain the single enantiomer of the required product. These approaches have also only been used to synthesize catechin based dimers, and are not readily adaptable for making the epicatechin dimer procyanidin B2.

A more recent synthetic route for the synthesis of procyanidin B2 is reported in the literature by Tuckmantel et al (J. Am. Chem. Soc. 121:12073-12081, 1999) (see FIG. 1 for Tuckmantel's synthetic route). Tuckmantel's synthesis of procyanidin B2 starts with direct benzylation of catechin and only resulted in a ~2% overall yield from commercially available catechin. The synthesis route started from the already optically active flavanol, catechin, utilizing protecting groups that allowed most of the chemistry to be carried out on more easily handled less polar compounds. However, there are two main limitations in this published synthetic route. The first limitation in the described method is the low yield of tetrabenzyl-catechin, just 20% in the first step of the synthetic route, which make commercial production (kilogram quantities) too costly. The second limitation in the previously described method is the requirement of a two step inversion of stereochemistry at C-3 to give the key intermediate, tetrabenzyl-epicatechin 2. The overall yield of tetrabenzyl-epicatechin was only ~15% from the starting catechin material. This further limits the effectiveness of the synthesis of procyanidin B2 5, as intermediate 2 is required in a four fold excess (see step 5, FIG. 1), which makes any improved synthesis of reaction intermediate 2 (i.e., tetrabenzylated product) (FIG. 1) even more useful. The tetrabenzylated epicatechin product is therefore an important intermediate for the synthesis of procyanidin B2.

In addition, *Uncaria tomentosa* or cat's claw is expected to have immune-supporting, anti-inflammatory, anti-viral, anti-mutagenic and antioxidant properties. The anti-inflammatory properties, for example, are expected to be beneficial for the treatment of arthritis, rheumatism, bursitis and gout. Without being bound by theory, it is believed that its beneficial effects in treating arthritis pain can be due, in part, to its ability to cleanse the digestive tract and aid in removing toxins from the body.

Further, *Uncaria tomentosa* or cat's claw is expected to alleviate pain. As such, Una de Gato is expected to be helpful in reducing pain associated with, for example, chemotherapy, radiation treatment and AZT use ("New Quinovic Glycosides from *Uncaria tomentosa*", Journal of Natural Products, 51 (2):257-261, 1988).

*Uncaria tomentosa* or cat's claw is also expected to be useful in stopping viral infections in the early stages, fighting opportunistic infections in AIDs patients, and decreasing the visible size of some skin tumors and cysts.

*Uncaria tomentosa* can also be used to treat a variety of ailments, including cancer, AIDs, Crohn's disease, respiratory infections, allergies, herpes, prostrate problems, lupus, Epstein Barr virus, chronic fatigue syndrome, and a variety of stomach and bowel disorders.

Pharmaceutical Compositions and Administration

In general, isolated, purified and/or synthetic procyanidin B2 compounds are administered in therapeutically effective amounts by any of the usual modes known in the art, either singly or in combination with at least one other compound of this disclosure and/or at least one other conventional therapeutic agent for the disease being treated. A therapeutically effective amount can vary widely depending on the disease, its severity, the age and relative health of the animal being treated, the potency of the compound(s), and other factors. As anti-fibril agents, therapeutically effective amounts of compounds of this disclosure can range from 1-1000 mg/kg of body weight; for example, 10-100 mg/kg of body weight. A person of ordinary skill in the art will be conventionally able, and without undue experimentation, having regard to that skill and to this disclosure, to determine a therapeutically effective amount of a compound for the treatment of amyloidosis or α-synuclein/NAC fibril formation.

In general, isolated, purified and/or synthetic procyanidin B2 compounds will be administered as pharmaceutical compositions by one of the following routes: oral, topical, systemic (e.g., transdermal, intranasal, or by suppository), or parenteral (e.g., intramuscular, subcutaneous, or intravenous injection). Compositions can take the form of tablets, pills, capsules, semisolids, powders, sustained release formulations, solutions, suspensions, elixirs, aerosols, or any other appropriate compositions; and comprise at least one compound of this disclosure in combination with at least one pharmaceutically acceptable excipient. Suitable excipients are well known to persons of ordinary skill in the art, and they, and the methods of formulating the compositions, can be found in such standard references as Alfonso A R: Remington's Pharmaceutical Sciences, 17th ed., Mack Publishing Company, Easton Pa., 1985. Suitable liquid carriers, especially for injectable solutions, include water, aqueous saline solution, aqueous dextrose solution, and glycols.

In particular, the compound(s) can be administered orally, for example, as tablets, troches, lozenges, aqueous or oily suspensions, dispersible powders or granules, emulsions, hard or soft capsules, syrups or elixirs. In one embodiment, only one such compound is administered in any particular dosage form. Compositions intended for oral use can be prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations.

Tablets contain the compound in admixture with non-toxic pharmaceutically acceptable excipients that are suitable for the manufacture of tablets. These excipients include, for example, inert diluents, such as calcium carbonate, sodium carbonate, lactose, calcium phosphate or sodium phosphate; granulating and disintegrating agents, for example, maize starch or alginic acid; binding agents, for example, maize starch, gelatin or acacia; and lubricating agents, for example, magnesium stearate or stearic acid or talc. The tablets can be uncoated or they can be coated by known techniques to delay disintegration and absorption in the gastrointestinal tract and thereby provide a sustained action over a longer period. For example, a time delay material such as glycerol monostearate or glycerol distearate can be employed. Formulations for oral use can also be presented as hard gelatin capsules wherein the compound is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Aqueous suspensions contain the compound in admixture with excipients suitable for the manufacture of aqueous suspensions. Such excipients include, for example, suspending agents, for example, sodium carboxymethylcellulose, methylcellulose, hydroxypropylmethyl cellulose, sodium alginate, polyvinylpyrrolidone, gum tragacanth and gum acacia; and dispersing or wetting agents that are naturally occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids such as hexitol, for example polyoxyethylene sorbitol monooleate, or condensation products of ethylene oxide with partial esters from fatty acids and a hexitol annhydride, for example polyethylene sorbitan monooleate. The aqueous suspensions can also contain one or more preservatives, for example ethyl or n-propyl p-hydroxybenzoate, one or more coloring agents, one or more flavoring agents, and/or one or more sweetening agents, such as sucrose or saccharin.

Oily suspensions can be formulated by suspending the compound in a vegetable oil, for example arachis oil, olive oil, sesame oil, or coconut oil, or in a mineral oil such as liquid paraffin. The oily suspensions can contain a thickening agent, for example beeswax, hard paraffin or cetyl alcohol. Sweetening agents, such as those set forth below, and flavoring agents can be added to provide a palatable oral preparation. These compositions can be preserved by the addition of an antioxidant such as ascorbic acid.

Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already described above. Additional excipients, for example sweetening, flavoring and agents, can also be present.

The compounds can also be in the form of oil-in-water emulsions. The oily phase can be a vegetable oil, for example olive oil or arachis oils, or a mineral oil, for example liquid paraffin, or mixtures thereof. Suitable emulsifying agents can be naturally-occurring gums, for example gum acacia or gum tragacanth, naturally occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsion can also contain sweetening and flavoring agents. Syrups and elixirs can be formulated with sweetening agents, for example, glycerol, sorbitol or sucrose. Such formulations can also contain a demulcent, a preservative and flavoring and coloring agents.

The compound can also be administered by injection or infusion, either subcutaneously, or intravenously, or intramuscularly, or intrasternally, or intranasally, or by infusion techniques in the form of sterile injectable or oleaginous suspension. The compound can be in the form of a sterile injectable aqueous or oleaginous suspensions. These suspensions can be formulated according to the known art using suitable dispersing of wetting agents and suspending agents such as those that have been described above. The sterile injectable preparation can also be a sterile injectable solution or suspension in a non-toxic parenterally-acceptable diluent or solvent for example, as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oils can be conventionally employed including synthetic mono- or diglycerides. In addition, fatty acids such as oleic acid find use in the preparation of injectables. Dosage regimens can be adjusted to provide the optimum therapeutic response. For example, several divided dosages can be administered daily or the dosage can be proportionally reduced as indicated by the exigencies of the therapeutic situation.

It is especially advantageous to formulate the compounds in dosage unit form for ease of administration and uniformity of dosage. Dosage unit form as used herein refers to physically discrete units suited as unitary dosages for the subjects to be treated, each containing a therapeutically effective quantity of the compound and at least one pharmaceutical excipient.

A drug product will comprise a dosage unit form within a container that is labeled or accompanied by a label indicating the intended method of treatment, such as the treatment of an amyloid disease, such as Alzheimer's disease, or of a disease associated with α-synuclein/NAC fibril formation, such as Parkinson's disease. The compounds may be packaged as articles of manufacture containing packaging material, a compound provided herein, which is, for example, effective for treatment of an amyloid disease, within the packaging material, and a label that indicates that the compound is used for treating, for example, an amyloid disease.

The following non-limiting Examples are given by way of illustration only and are not considered a limitation of this disclosure, many apparent variations of which are possible without departing from the spirit or scope thereof.

EXAMPLES

Example 1

General Experimental Procedures and HPLC Conditions Used in the Synthesis of Procyanidin B2

All solvents were distilled before use and were removed by rotary evaporation at temperatures up to 35° C. Octadecyl functionalised silica gel (C18) was used for reversed-phase (RP) flash chromatography, and Merck silica gel 60, 200-400 mesh, 40-63 µm, was used for silica gel flash chromatography. Thin layer chromatography was carried out using Merck DC-plastikfolien Kieselgel 60 $F_{254}$, first visualised with an ultraviolet (UV) lamp, and then by dipping in a vanillin solution (1% vanillin, 1% $H_2SO_4$ in ethanol), and heating. Optical rotations were measured on a Perkin-Elmer 241 polarimeter. Mass, UV, and infrared (IR) spectra were recorded on Kratos MS-80, Shimadzu UV 240, and Perkin-Elmer 1600 FTIR instruments, respectively. NMR spectra, at 25° C., were recorded at 500 or 300 MHz for $^1$H, and 125 or 75 MHz for $^{13}$C on Varian INOVA-500 or VXR-300 spectrometers. Chemical shifts are given in ppm on the δ scale referenced to the solvent peaks $CHCl_3$ at 7.25 and $CDCl_3$ at 77.0 ppm or $(CH_3)_2CO$ at 2.15 and $(CD_3)_2CO$ at 30.5 ppm.

For all studies involving high pressure liquid chromatography (HPLC) analysis, the analytical HPLC equipment consisted of a Waters 717 autosampler, 600 pump and controller, and a 2487 UV detector controlled by Omega software. Samples were analyzed by using an RP-18 semi-preparative column (Phenomenex Jupiter 5 µm C18 300A, 250×10 mm)

with a guard column (Phenomenex SecurityGuard cartridge containing a C18 ODS 4×3 mm, 5 μm column) fitted at 30° C. Samples (5 μL) were analyzed using a mobile phase flow rate of 5.0 ml/min, with UV detection at 280 nm. Solvent A consisted of $CH_3CN/H_2O$ (95:5) containing 0.1% TFA. Solvent B consisted of $H_2O$ containing 0.1% TFA. The composition of the mobile phase as a function of time is given in Table 1.

TABLE 1

| Time (minutes) | % Solvent A | % Solvent B |
|---|---|---|
| 0 | 11 | 89 |
| 20 | 11 | 89 |
| 30 | 100 | 0 |
| 31 | 11 | 89 |

Example 2

Figure 2:
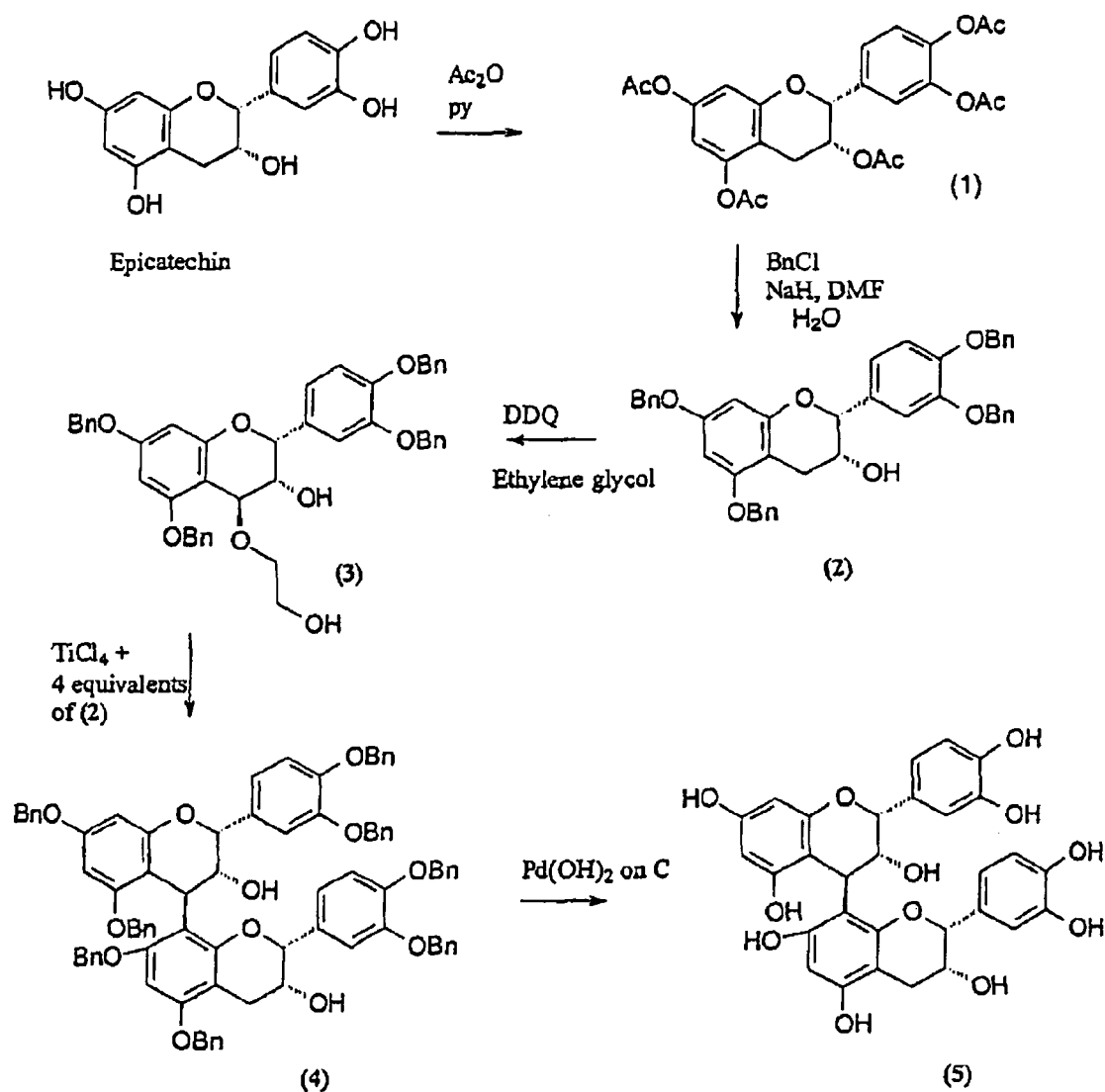
FIG. 2 is a schematic representation of the 5-step methods to produce procyanidin B2 in accordance with the present disclosure.

Preparation of 5,7,3',4',3"-Penta-O-acetylepicatechin (Step 1, FIG. 2)

To a suspension of epicatechin (2.5 g) in pyridine (10 ml) was added drop wise with stirring acetic anhydride (10 ml). The mixture was stirred for a further 48 hours at room temperature, then poured onto ice water (200 ml), allowed to come to room temperature, and then stood for an additional 2 hours. The mixture was extracted with ethyl acetate (200 ml) which was then washed with aqueous hydrochloric acid (1M, 200 ml) separated, dried and evaporated in vacuo to give the epicatechin pentaacetate (1) as a pale yellow gum (4.5 g, 87% yield).

Figure 3:
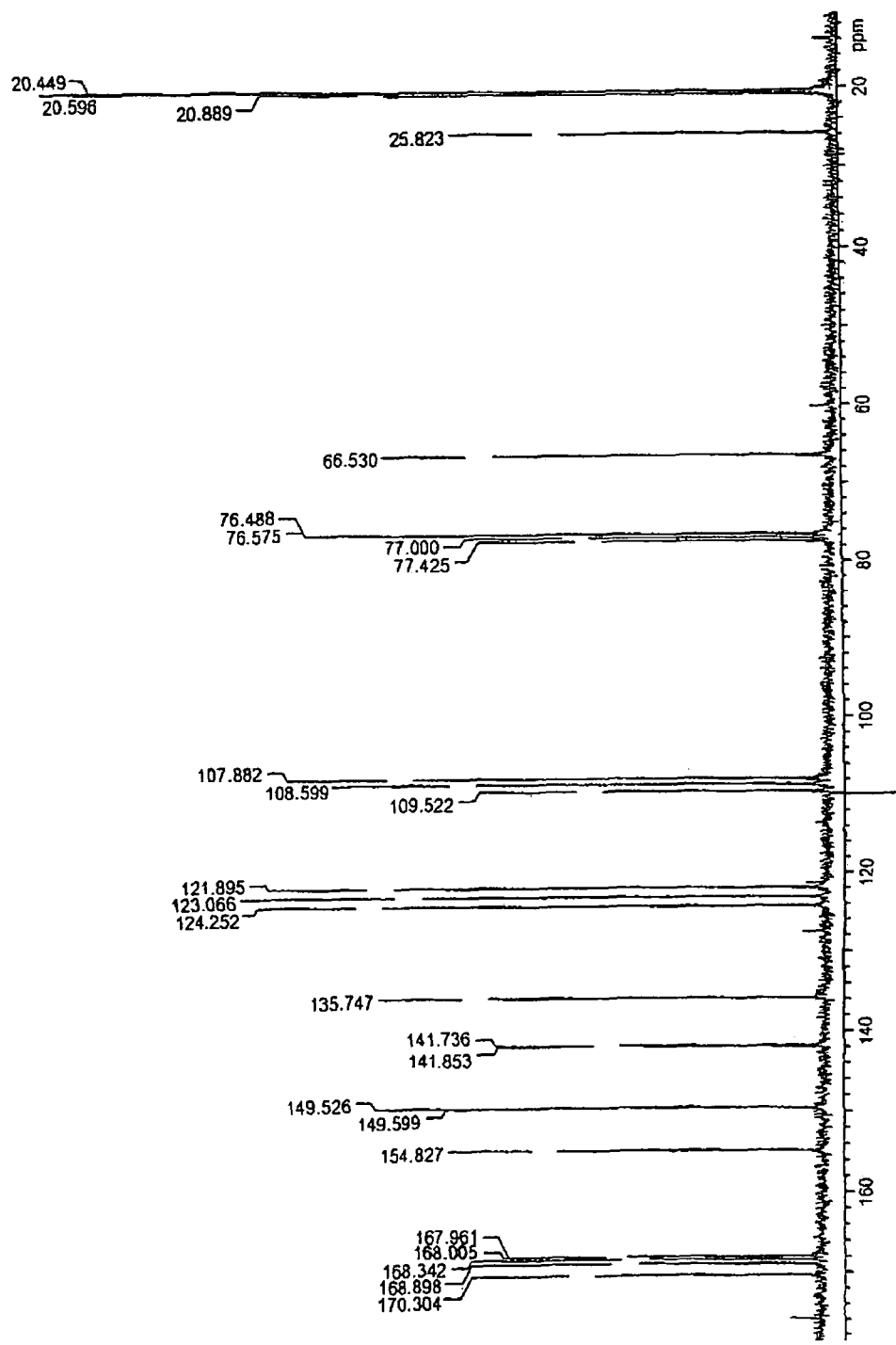
FIG. 3 is the $^{13}$C-NMR (CDCl$_3$) of the epicatechin pentaacetate intermediate following step 1 of the synthetic route of FIG. 2.

$^{13}$C-NMR (CDCl$_3$) 170.3, 168.9, 168.3, 168.0, 167.9, 154.8, 149.6, 149.5, 141.9, 141.7, 135.7, 124.3, 123.1, 121.9, 109.5, 108.6, 107.9, 76.5, 66.5, 25.8, 20.9, 20.6, 20.6, 20.4 and 20.4 (FIG. 3).

Example 3

Preparation of 5,7,3',4'-Tetra-O-benzylepicatechin (Step 2, FIG. 2)

To a stirred solution of epicatechin pentaacetate (1) (4.5 g) and benzyl chloride (4.1 ml) in dimethylformamide (DMF) (50 ml) at 0° C. was added sodium hydride (2.5 g, 80% dispersion in oil) over 10 minutes, and then water (0.54 ml) drop wise over 30 minutes. The mixture was brought to room temperature, stirred for a further 48 hours, then poured onto hydrochloric acid (200 ml, 1M) and ice (200 g). After allowing to come to room temperature and standing for 2 hours, the mixture was extracted into ethyl acetate (2×200 ml), dried and evaporated in vacuo to give an orange gum. Further evaporation under high vacuum overnight gave an orange crystalline solid. Purification by column chromatography over silica gel eluting with cyclohexane/dichloromethane (1:1), followed by dichloromethane (100%) gave the tetrabenzylepicatechin (2) as a pale yellow crystalline solid (4.2 g, 75% yield).

Figure 4:
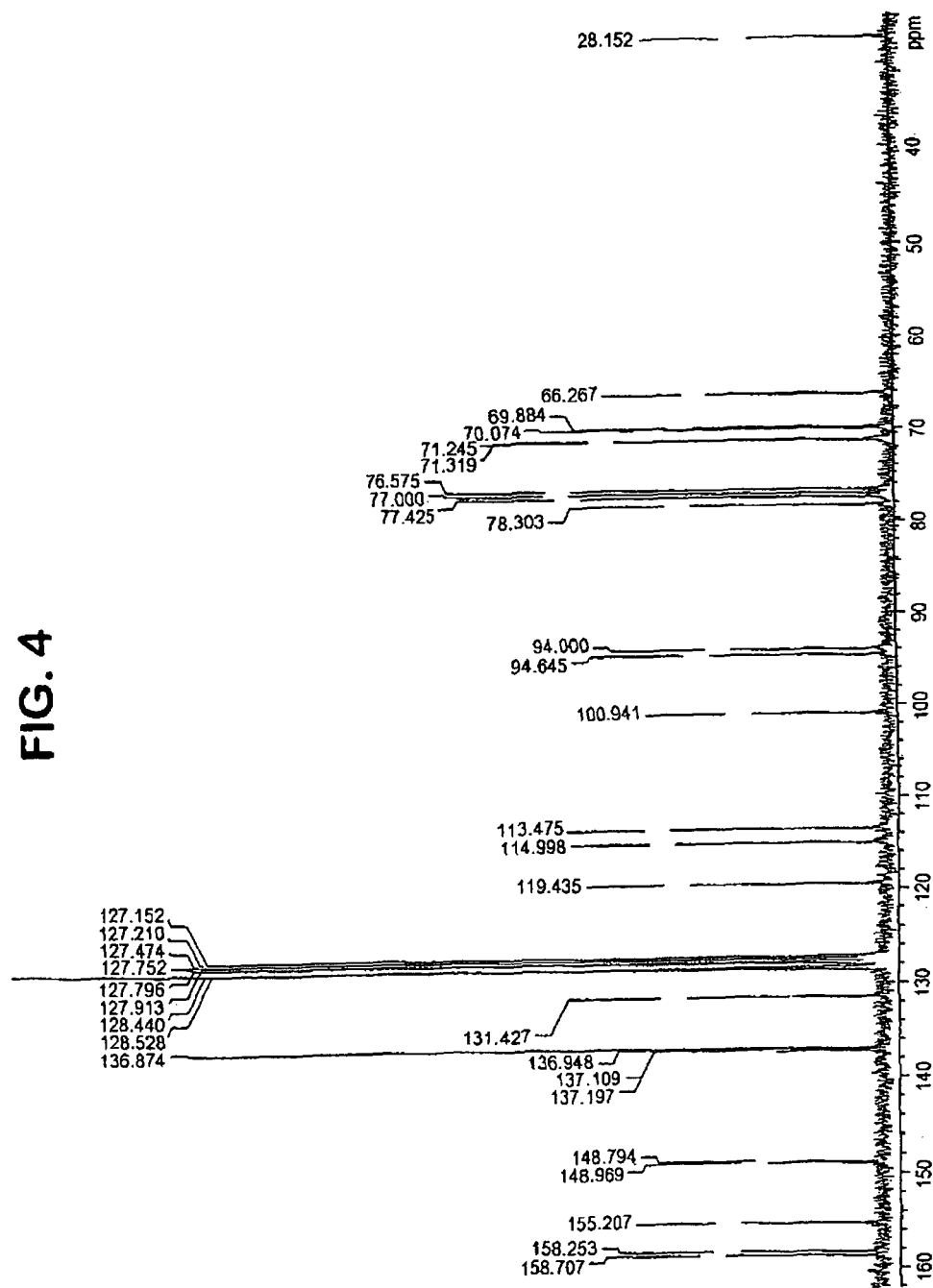
FIG. 4 is the $^{13}$C-NMR (CDCl$_3$) of the tetrabenzylepicatechin intermediate following step 2 of the synthetic route of FIG. 2.

$^{13}$C NMR-(CDCl$_3$) 158.7, 158.3, 155.2, 149.0, 148.8, 137.2, 137.1, 136.9, 131.4, 128.5, 128.4, 127.9, 127.8, 127.7, 127.5, 127.2, 127.2, 119.4, 115.0, 113.5, 100.9, 94.6, 94.0, 78.3, 71.3, 71.2, 70.1, 69.9, 66.3 and 28.2 (FIG. 4).

Example 4

Preparation of 5,7,3',4'-Tetra-O-benzyl-4-(2-hydroxyethoxy)epicatechin (Step 3, FIG. 2)

To a stirred solution of tetrabenzylepicatechin (2) (3 g) in anhydrous dichloromethane ($CH_2Cl_2$) (30 ml) under a calcium chloride ($CaCl_2$) tube was added, at room temperature, ethylene glycol (1.5 ml) and then all at once with good stirring, 2,3-dichloro-5,6-dicyano-1,4-benzoquinone (DDQ) (2.1 g). After 2 hours of vigorous stirring, 4-(dimethylamino)pyridine (DMAP) (1.125 g) was added and stirring continued for 15 minutes. The mixture was then put down a flash vacuum column, eluting with $CH_2Cl_2$ (50 ml), 10% ethyl acetate (EtOAc) in $CH_2Cl_2$ (2×50 ml), then 20% EtOAc in $CH_2Cl_2$ (2×50 ml) to give the crude product. Purification by column chromatography over silica gel eluting with $CH_2Cl_2$ containing increasing proportions of EtOAc gave the ethylene glycol adduct (3) as a pale pink gum (1.35 g, 41 yield %).

Figure 5:
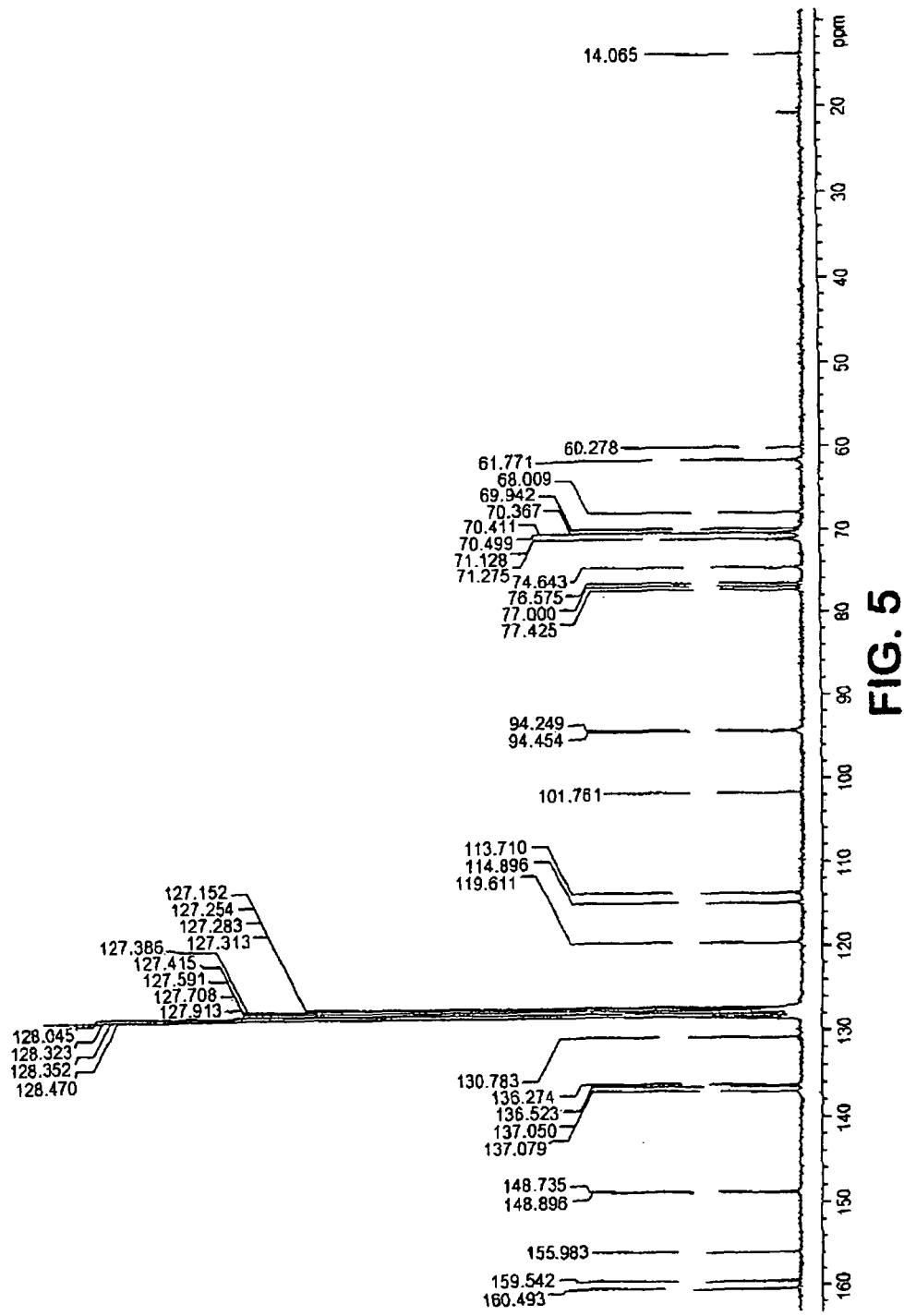
FIG. 5 is the $^{13}$C-NMR (CDCl$_3$) of the ethylene glycol adduct intermediate following step 3 of the synthetic route of FIG. 2.

$^{13}$C NMR-(CDCl$_3$) 160.5, 159.5, 156.0, 148.9, 148.7, 137.1, 137.1, 136.5, 136.3, 130.8, 119.6, 114.9, 113.7, 101.8, 94.4, 94.2, 74.6, 71.3, 71.1, 70.5, 70.4, 70.4, 69.9, 68.0 and 61.8 (FIG. 5).

Example 5

Preparation of 5,7,3',4'-Tetra-O-benzylepicatechin-4β→8-5,7,3',4'-tetra-O-benzylepicatechin (Step 4, FIG. 2)

To a solution of 5,7,3',4'-tetra-O-benzyl-4-(2-hydroxyethoxy)epicatechin (3) (1.0 g) and 5,7,3',4'-tetra-O-benzylepicatechin (2) (4.0 g) in anhydrous tetrahydrofuran (THF) (12 ml) and anhydrous $CH_2Cl_2$ (15 ml) was added, drop-wise with stirring at 0° C. under nitrogen, titanium tetrachloride (TiCl$_4$) (1M in $CH_2Cl_2$, 2.8 ml). The mixture was warmed to room temperature, then stirred for a further 2 hours, then quenched with aqueous saturated sodium hydrogen carbonate (NaHCO$_3$) (20 ml) and water (40 ml). More $CH_2Cl_2$ (100 ml) was added, the organic layer separated, dried and evaporated in vacuo to give the crude product. The product was dissolved in hot ethyl acetate (EtOAc)/ethanol (EtOH) (6 ml/10 ml), and allowed to stand overnight to crystallize. The crystals were filtered off, and washed with a minimum of the cold solvent, and then the mother liquor was evaporated to dryness.

Purification of the dimer (4) from the mother liquor by column chromatography over silica gel eluting with cyclohexane/$CH_2Cl_2$/EtOAc (13:13:1) gave the benzylated dimer (4) as a pale yellow gum (0.70 g, 39% yield).

Figure 6:
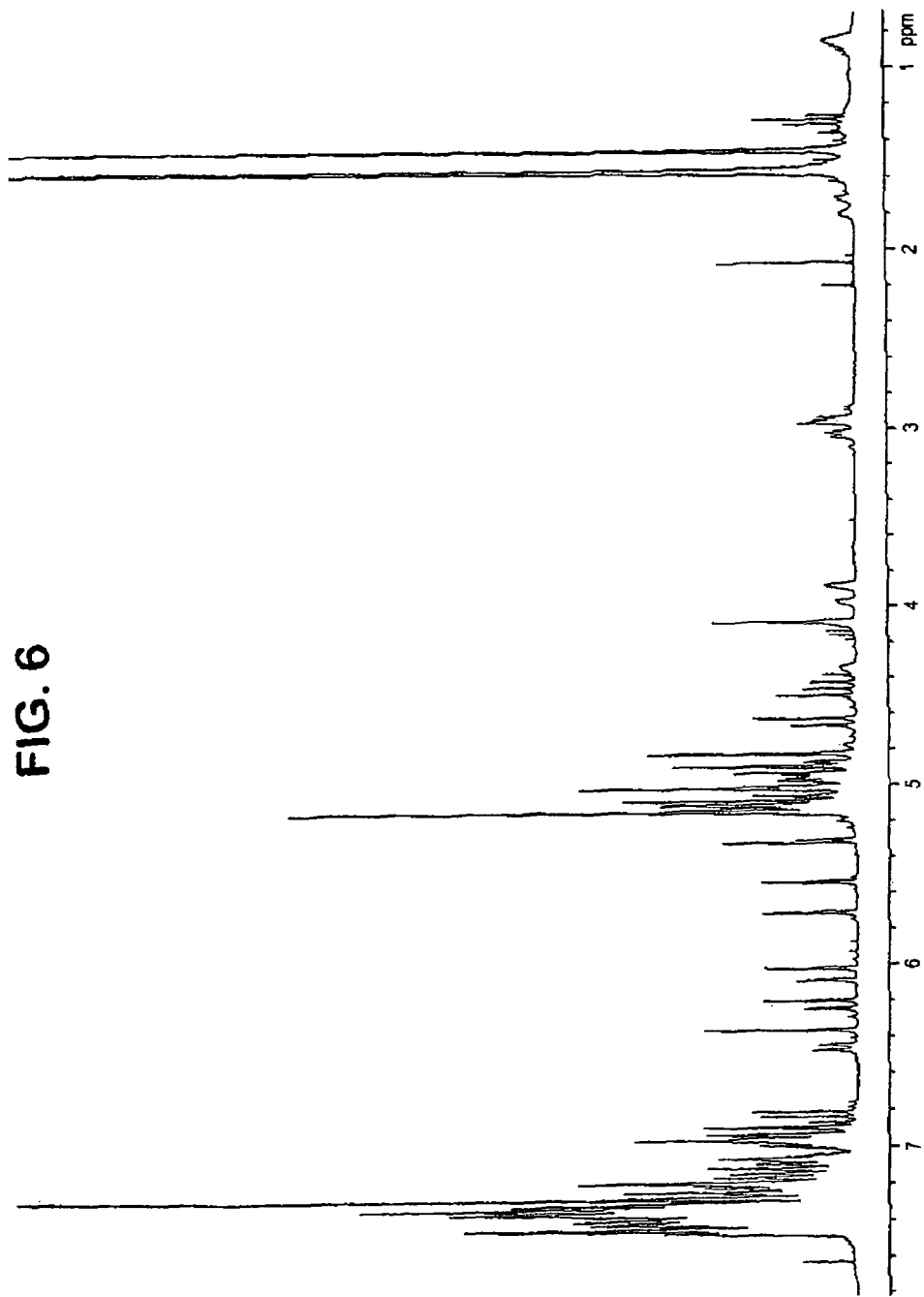
FIG. 6 is the $^1$H-NMR (CDCl$_3$) of the protected dimer intermediate following step 4 of the synthetic route of FIG. 2.
Figure 7:
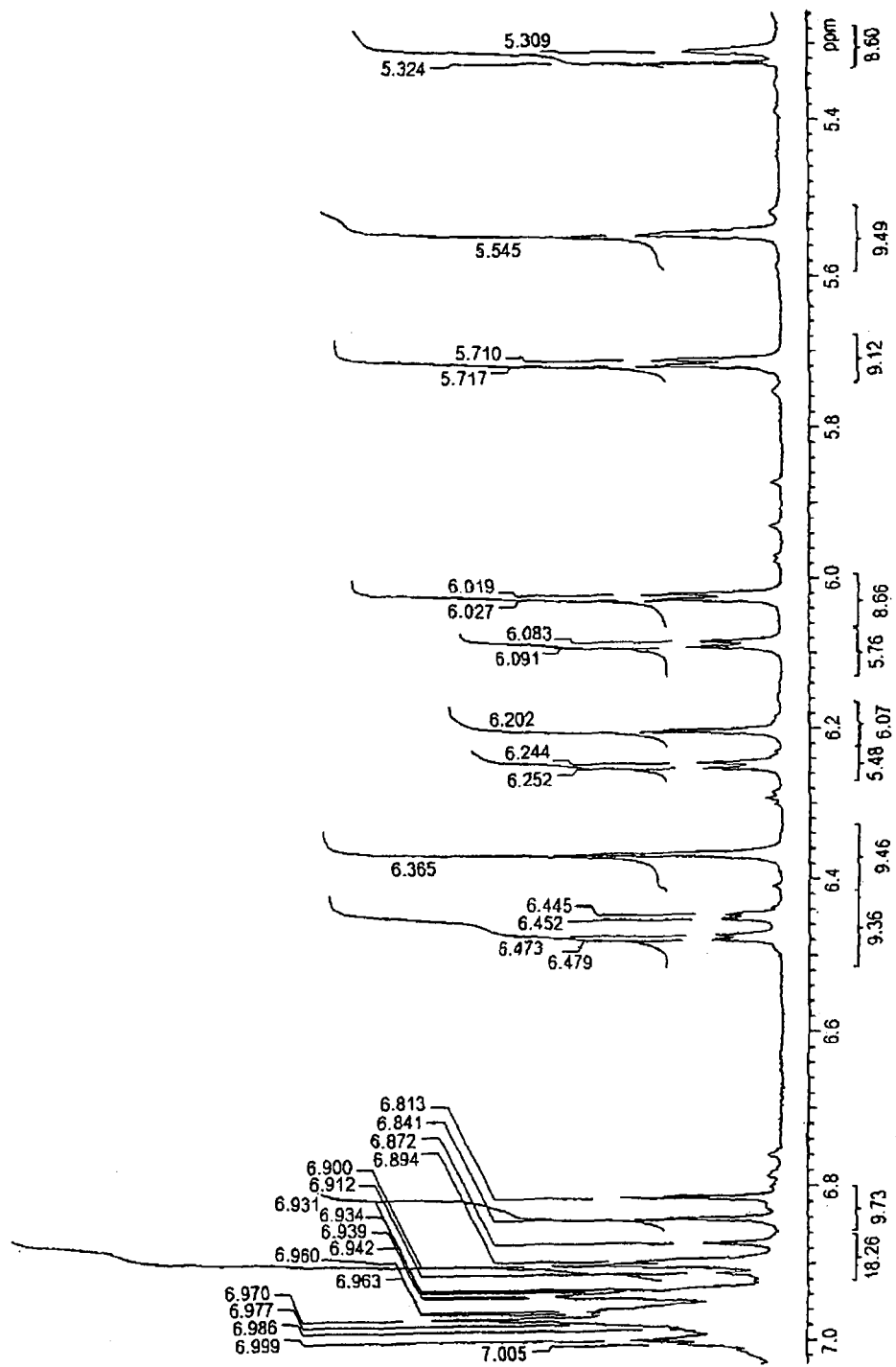
FIG. 7 is the $^1$H-NMR (CDCl$_3$) of the protected dimer intermediate following step 4 of the synthetic route of FIG. 2, with an expansion of the 5.2 to 7.1 ppm region of FIG. 6.
Figure 8:
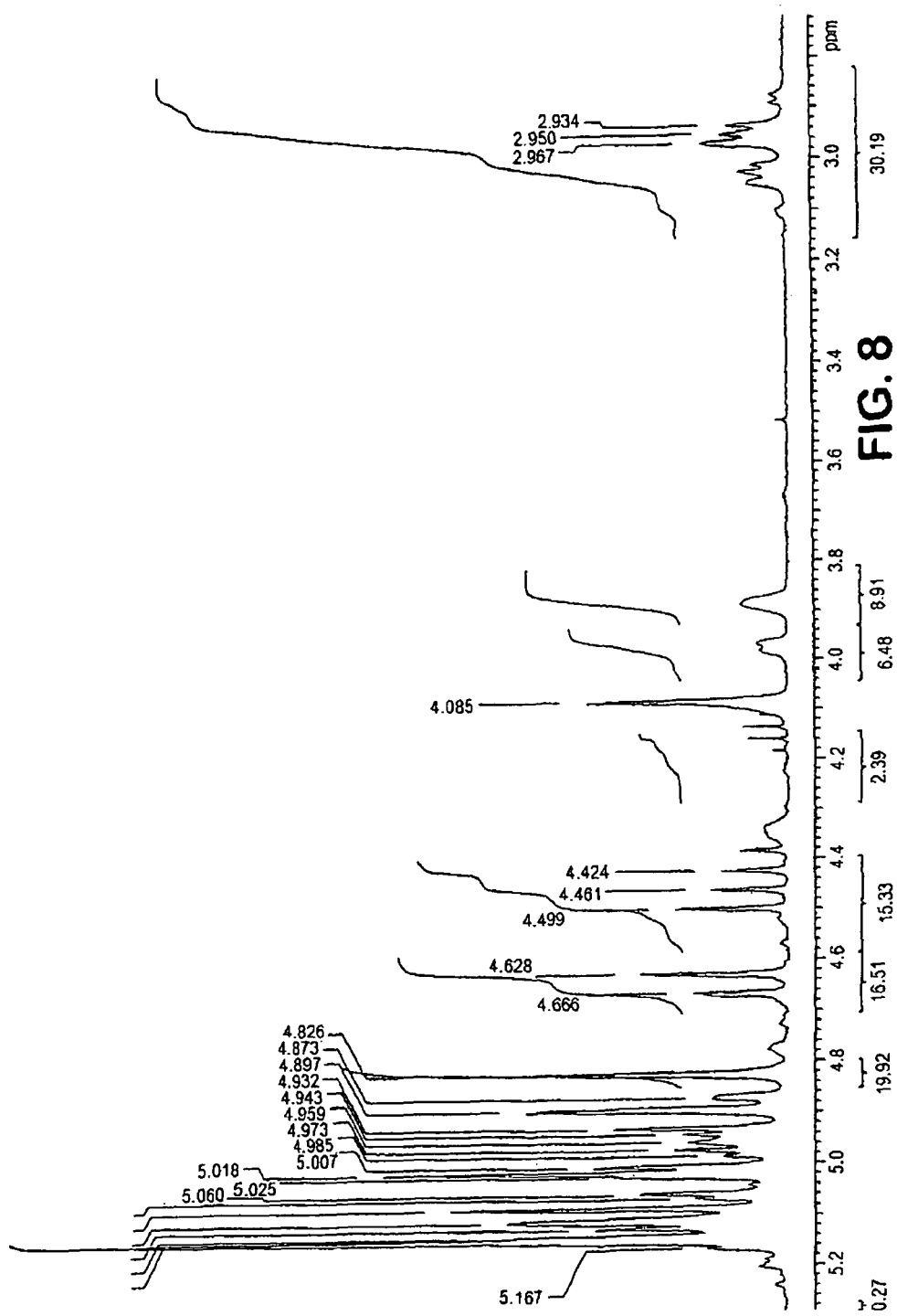
FIG. 8 is the $^1$H-NMR (CDCl$_3$) of the protected dimer intermediate following step 4 of the synthetic route of FIG. 2, with an expansion of the 2.0 to 5.2 ppm region of FIG. 6.

$^1$H-NMR (CDCl$_3$) (consisting of 2 rotamers, approx. 3:1, MR=major, mr=minor rotamer) 6.82, 6.46 (Abq, 2H, MR, J 8 Hz, B part d with J 1.5 Hz), 6.37 (s, 1H, MR), 6.25, 6.09 ABq, 2H, mr, J 2.5 Hz), 6.20 (s, 1H, m), 6.02, 5.71 (Abq, 2H, MR, J 2 Hz), 5.54 (s, 1H, MR), 5.31 (s, 1H, m), 4.65, 4.47 (ABq, 2H, MR, J 11 Hz), 4.65, 4.41 (ABq, 2H, mr, J 12 Hz), 4.34 (m, 1H, m), 4.09 (br overlapping, 1H, MR), 4.08 (s, 1H, MR), 3.98 (br d, 1H, mr J 6 Hz), 3.88 (m, 1H, MR) and 3.12-2.86 (m, 2H, MR +mr) (FIGS. 6-8).

Example 6

Preparation of Epicatechin-4β→8-Epicatechin (Step 5, FIG. 2)

To a solution of the benzylated dimer (700 mg) in tetrahydrofuran (THF) (30 ml) ere added methanol (MeOH) (30 ml), water (1.5 ml) and palladium hydroxide on carbon Pd(OH)$_2$/C) (20%, containing up to 50% H$_2$O, 300 mg). The mixture was shaken under an atmosphere of hydrogen for 2 hours, filtered through ceelite, which was washed with methanol. HPLC analysis (FIG. 9) of the dried product, showed it to contain about 80% of the procyanidin dimer B2 at 10.3 minutes, together with small amounts of epicatechin at 12.4 minutes, and the procyanidin trimer C1 at 17.6 minutes, all identical with pure samples.

Final purification of the product was accomplished by column chromatography over Sephadex LH20 when 95% ethanol eluted the procyanidin dimer B2 in fractions 45 to 56 (140 mg, 50% yield). The purified procyanidin B2 is observed at 10.3 minutes in the HPLC tracing of FIG. 10.

Figure 11:
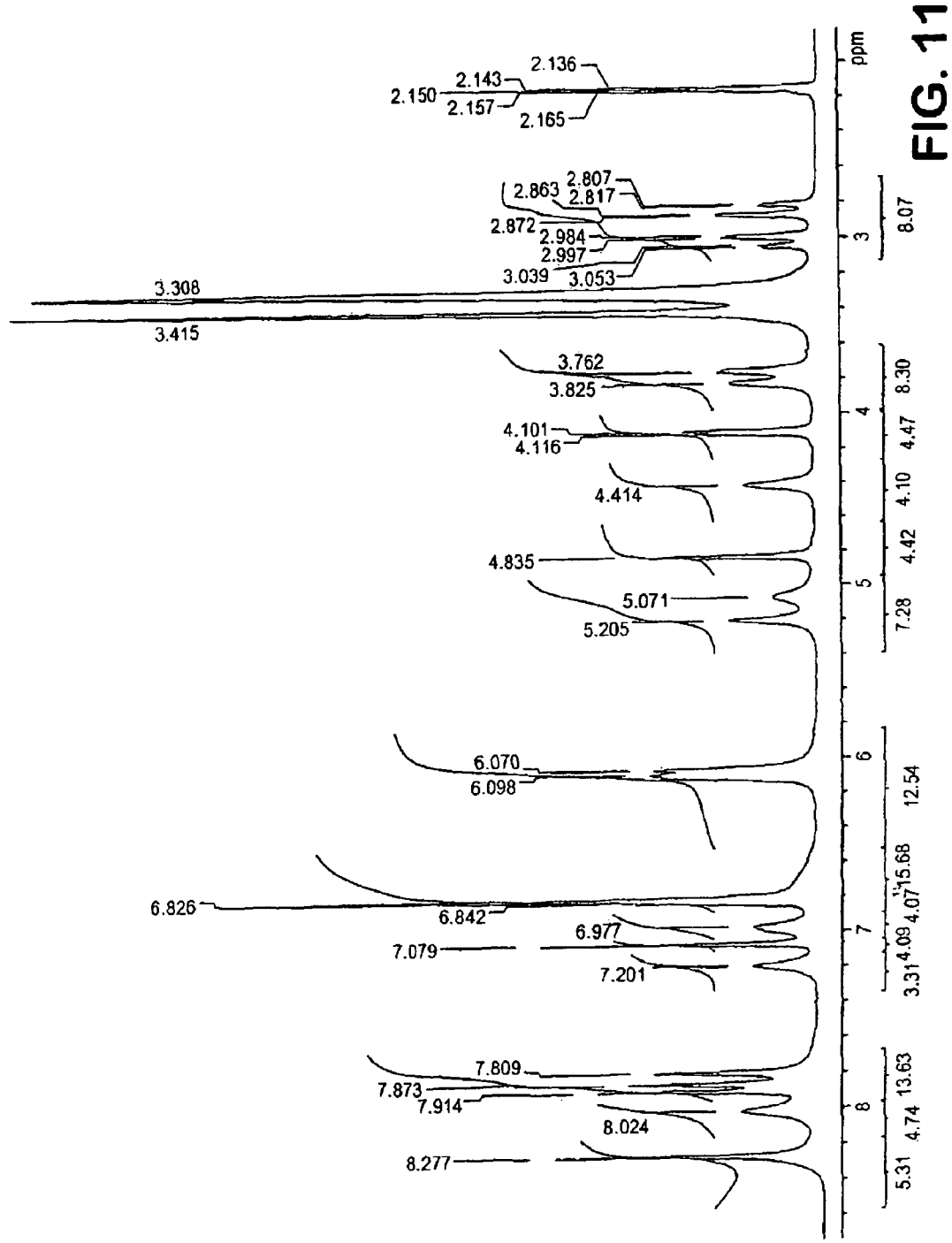
FIG. 11 is the $^1$H-NMR $(CDCl_3)_2CO$ of procyanidin B2 synthesized by the synthetic route of FIG. 2, followed by final purification using LH column chromatography.

$^1$H-NMR $(CD_3)_2CO$: 2.83 (1H, d, J17), 2.96 (1H, dd, J5, 17), 3.76 (1H, m, OH), 3.83 (1H, m, OH), 4.10 (1H, d, J5), 4.41 (1H, br s), 4.83 (1H, s), 5.07 (1H, br s), 5.20 (1H, br s), 6.07 (1H, s), 6.09 (1H, s), 6.11 (1H, s), 6.83 (3H, s), 7.00 (1H, br s), 7.08 (1H, s), 7.20 (1H, s), 7.81 (1H, s, OH), 7.87 (1H, s, OH), 7.91 (1h, s, OH), 8.02 (1H, br s, OH) and 8.28 (2H, s, OH) (FIG. 11).

Figure 12:
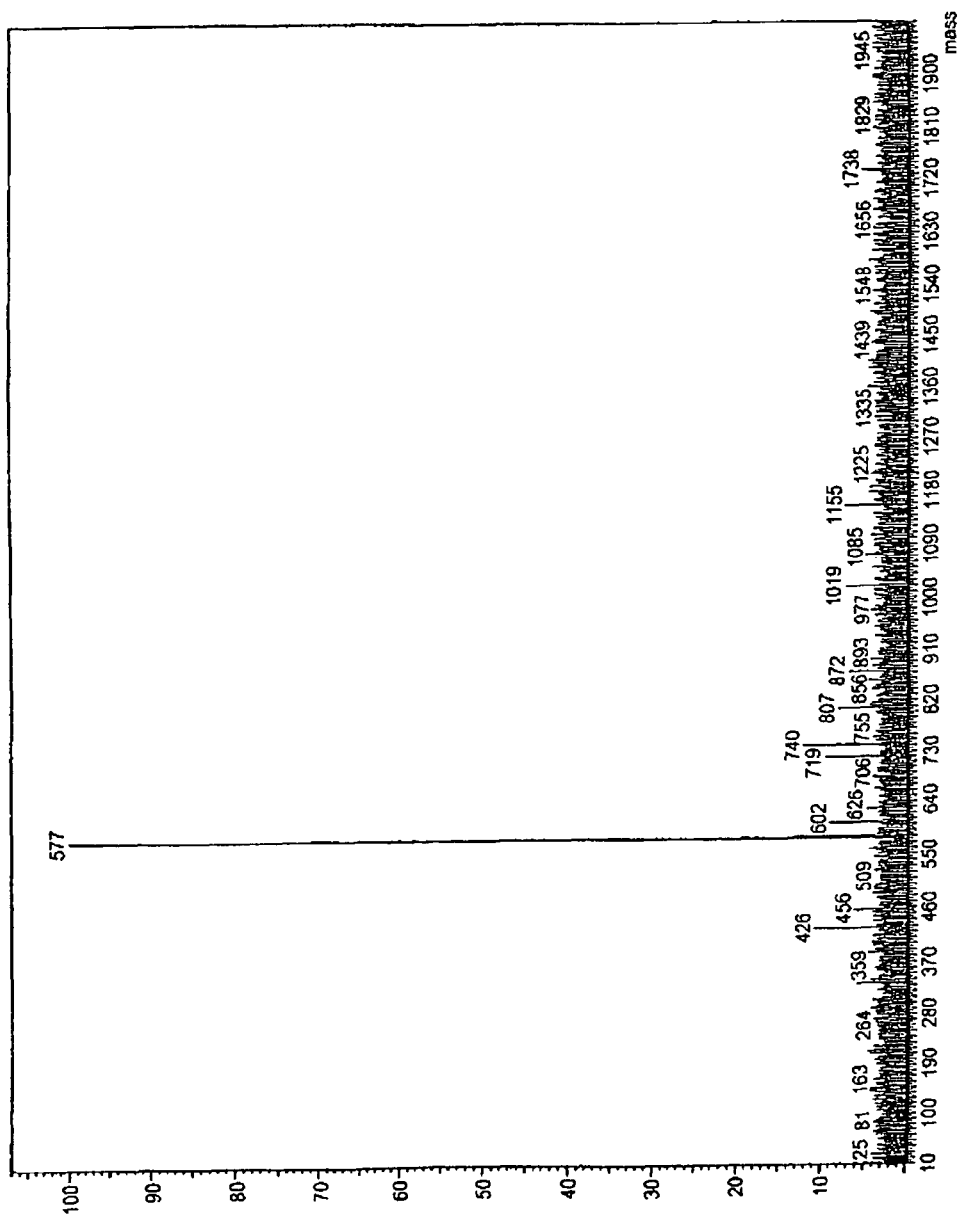
FIG. 12 is the −ve ion electrospray mass spectrum of procyanidin B2 of the synthetic route of FIG. 2.

−ve electrospray m.s. 577 ($M^+$-H, 100%) (FIG. 12)

$[\alpha]^{17}$ 589 nm+30.2°, $[\alpha]^{17}$ 577 nm+20.8°, $[\alpha]^{17}$ 546 nm+7.3°, $[\alpha]^{17}$ 435 nm−77.2°, $[\alpha]^{17}$ 404 nm −91.0°. The data correlates well with literature data identifying procyanidin B2 (Tuckmantel et al, J. Am. Chem. Soc. 121:12073-12081, 1999).

Example 7

Synthetic Procyanidin B2 is a Potent Inhibitor/Disrupter of Aβ Fibrils

Synthetic procyanidin B2 (i.e., epicatechin-4β→8-epicatechin), synthesized as described in accordance with the present disclosure, is a potent inhibitor/disrupter of Alzheimer's disease beta-amyloid protein (Aβ) fibrils. In a first set of studies, the efficacy of synthetic procyanidin B2 was directly compared to procyanidin B2 isolated from a specific Uncaria tomentosa (i.e., cat's claw) extract referred to as "PTI-777," and to procyanidin B2 isolated directly from the bark powder of Uncaria tomentosa, for their ability to cause a disassembly/disruption of pre-formed amyloid fibrils of Alzheimer's disease (i.e., consisting of Aβ 1-42 fibrils).

In one study, Thioflavin T fluorometry was used to determine the effects of procyanidin B2 isolated from PTI-777, procyanidin B2 isolated from cat's claw bark powder, procyanidin B2 synthesized as disclosed herein, and EDTA (as a negative control). In this assay, Thioflavin T binds specifically to fibrillar amyloid, and this binding produces a fluorescence enhancement at 485 nm that is directly proportional to the amount of amyloid fibrils formed. The higher the fluorescence, the greater the amount of amyloid fibrils formed (Naki et al, Lab. Invest. 65:104-110, 1991; Levine III, Protein Sc. 2:404-410, 1993; Amyloid Int. J. Exp. Clin. Invest. 2:1-6, 1995).

In this study, 25 μM of pre-fibrillized Aβ 1-42 (Bachem Inc) was incubated at 37° C. for 1 week either alone, or in the presence of a) procyanidin B2 isolated from PTI-777, b) procyanidin B2 isolated from cat's claw bark powder, c) synthetic procyanidin B2, or d) EDTA (at Aβ:test compound weight ratios of 1:1, 1:0.1, 1:0.01 or 1:0.001). Following 3-days of co-incubation, 50 μl of each incubation mixture was transferred into a 96-well microtiter plate containing 150 μl of distilled water and 50 μl of a Thioflavin T solution (i.e., 500 mM Thioflavin T in 250 mM phosphate buffer) (pH 6.8). The fluorescence was read at 485 nm (444 nm excitation wavelength) using an ELISA plate fluorometer after subtraction with buffer alone or compound alone, as blank.

Figure 13:
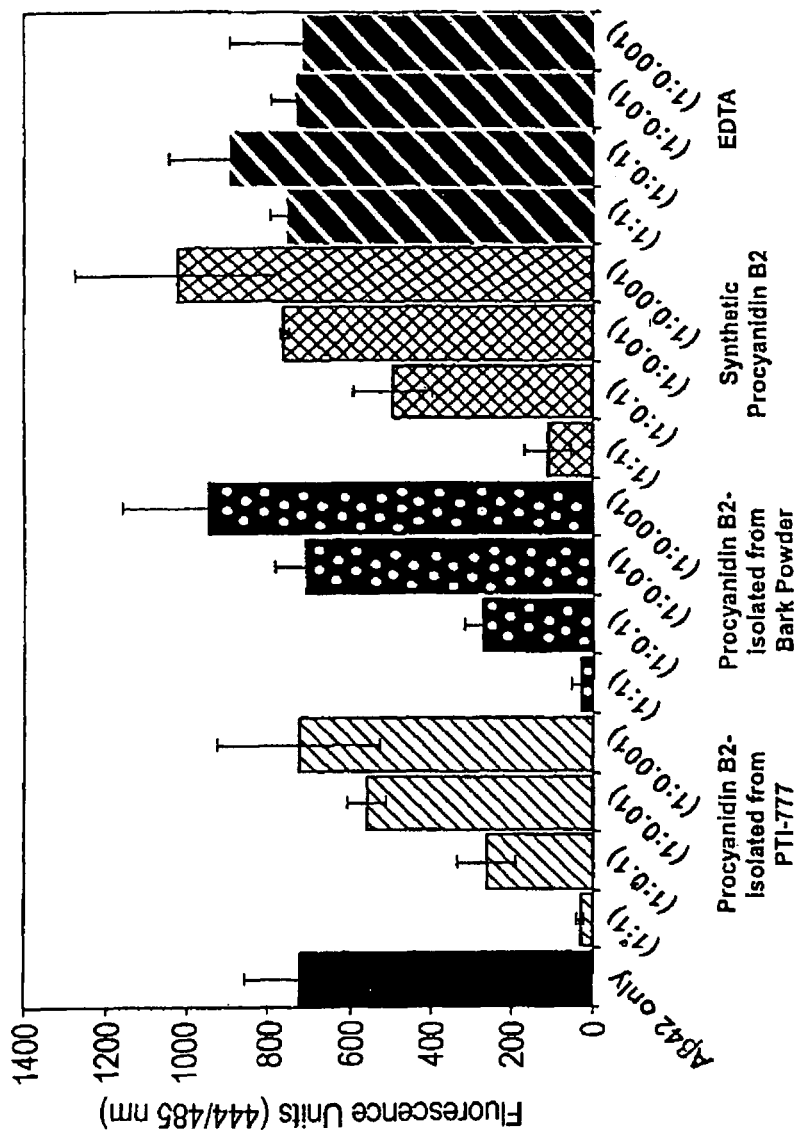
FIG. 13 is a Thioflavin T fluorometry assay demonstrating that synthetic procyanidin B2 is as effective as procyanidin B2 isolated from plant material for the disruption/disassembly of Aβ fibrils.

The results of day 3 incubations are presented (FIG. 13). Whereas EDTA caused no significant inhibition of Aβ 1-42 fibrils at all concentrations tested, synthetic procyanidin B2 caused a dose-dependent disruption/disassembly of pre-formed Aβ 1-42 fibrils, similar to procyanidin B2 isolated from cat's claw bark powder or from PTI-77 (FIG. 13). Synthetic procyanidin B2 caused a significant (p<0.01) 84.5+/−7.9% disruption when used at an Aβ:Procyanidin B2 wt/wt ratio of 1:1, and a significant (p<0.05) 31.5+/−13.5% disruption when used at an Aβ:Procyanidin B2 wt/wt ratio of 1:0.1. This study indicated that synthetic procyanidin B2 produced by the methods disclosed herein is a potent disruptor of Alzheimer's disease type Aβ fibrils, and exerts its effect in a dose-dependent manner.

The disruption of Aβ 1-42, even in its monomeric form, was confirmed by a study involving the use of SDS-PAGE and Western blotting methods (not shown). In this latter study, triplicate samples of pre-fibrillized Aβ 1-42 (25 μM) was incubated at 37° C. for 3 and 7 days either alone or in the presence of a) procyanidin B2 isolated from PTI-777, b) procyanidin B2 isolated from cat's claw bark powder, c) synthetic procyanidin B2, or EDTA. A 5 μg aliquot of each sample was then filtered through a 0.2 μm filter. Protein recovered from the filtrate was then loaded, and ran on a 10-20% Tris-Tricine SDS-PAGE, blotted to nitrocellulose and detected by ECL using an Aβ-antibody (clone 6E10; Senetek). In this study, Aβ 1-42 was detected as a ~4 kilodalton band (i.e., monomeric Aβ) following incubation alone, or in the presence of EDTA, at both 3 and 7 days. Aβ 1-42 monomers were not detected following incubation of Aβ 1-42 with either a) procyanidin B2 isolated from PTI-777, b) procyanidin B2 isolated from cat's claw bark powder, or c) synthetic procyanidin B2 by 7 days of co-incubation (not shown) suggesting that these compounds were capable of causing a disappearance of monomeric Aβ 1-42. This study confirmed that synthetic procyanidin B2 was also capable of causing a disruption/removal of monomeric Aβ 1-42.

Example 8

Synthetic Procyanidin B2 is a Potent Inhibitor of Fibrillar Aβ Binding to Congo Red In the Congo red binding assay (as described below) the ability of a given test compound to alter amyloid (in this case, Aβ) binding to Congo red is quantified. In this assay, Aβ 1-42+/−test compounds were incubated for 3 days and then vacuumed through a 0.2 μm filter. The amount of Aβ 1-42 retained in the filter (i.e., "retentate") was then quantitated following staining of the filter with Congo red. After appropriate washing of the filter, any lowering of the Congo red color on the filter in the presence of the test compound (compared to the Congo red staining of the amyloid protein in the absence of the test compound) was indicative of the test compound's ability to diminish/alter the amount of aggregated and congophilic Aβ.

Figure 14:
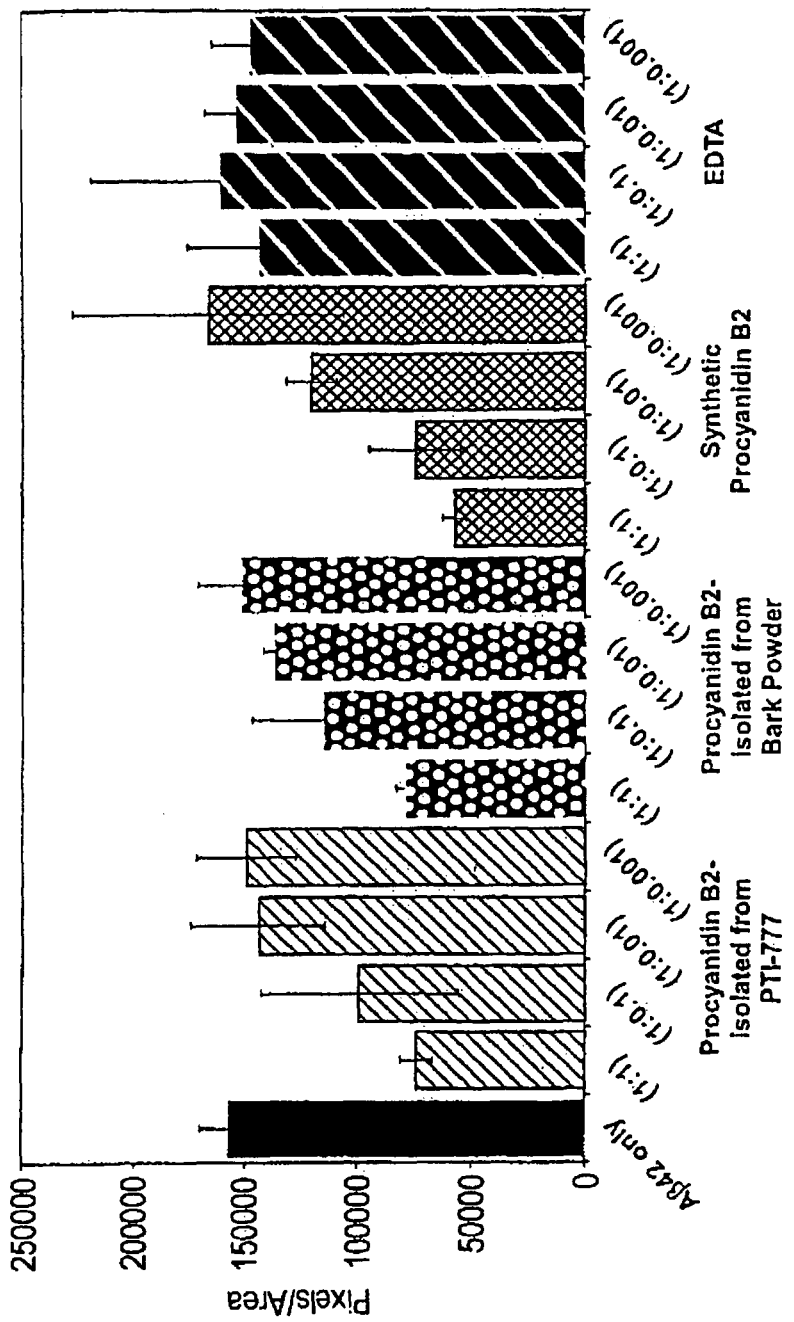
FIG. 14 is a Congo red binding assay demonstrating that synthetic procyanidin B2 is as effective as procyanidin B2 isolated from plant material for the disruption/disassembly of Aβ fibrils.

In one study (FIG. 14), the ability of Aβ fibrils to bind Congo red in the absence or presence of increasing amounts of a) procyanidin B2 isolated from PTI-777, b) procyanidin B2 isolated from cat's claw bark powder, c) synthetic procyanidin B2, or d) EDTA (at an Aβ:test compound weight ratios of 1:1, 1:0.1, 1:0.01 or 1:0.001) was determined. The results of day 3 incubations are presented (FIG. 14). Whereas EDTA caused no significant inhibition of Aβ 1-42 fibril binding to Congo red at all concentrations tested, synthetic procyanidin B2 caused a dose-dependent inhibition of fibrillar Aβ 1-42 binding to Congo red, even greater than that observed with either procyanidin B2 isolated from cat's claw bark powder or from PTI-77 (FIG. 14). Synthetic procyanidin B2 caused a significant (p<0.01) 46.3+/−4.3% inhibition of Congo red binding to Aβ 1-42 fibrils when used at an Aβ:Procyanidin B2 wt/wt ratio of 1:1, and a significant (p<0.01) 30.3+/−8.0% inhibition of Congo red binding when used at an Aβ:Procyanidin B2 wt/wt ratio of 1:0.1. In comparison, procyanidin B2 isolated from bark powder inhibited Aβ 1-42 fibril binding to Congo red by 36.3+/−4.3% at an Aβ:Procyanidin B2 wt/wt ratio of 1:1, and not significantly when used at an Aβ:Procyanidin B2 wt/wt ratio of 1:0.1 (FIG. 14). This study indicates that synthetic procyanidin B2 produced by the methods disclosed herein is a potent inhibitor of Alzheimer's disease type Aβ fibril binding to Congo red, and exerts its effect in a dose-dependent manner.

Example 9

Further In Vitro and In Vivo Testing of Synthetic Procyanidin B2

Further in vitro and in vivo assays can be used to test synthetic procyanidin B2 and related compounds for their effectiveness in the treatment of amyloid disease, including but not limited to Alzheimer's disease. For an example of further in vitro testing, stock solutions of peptides (1 mM) can be prepared in pyrogen-free sterile water and diluted to the indicated concentrations in defined culture media. Rat hippocampal cultures (10-14 days in vitro) can be treated with peptides or vehicle for 4 days. The viability of the rat cortical cultures could be visually assessed by phase contrast microscopy and quantified by measuring lactate dehydrogenase (LDH) released into the culture media.

Assay 1

Primary rat hippocampal neurons could be cultured in vitro with standard cell culture techniques. Beta-amyloid protein (Aβ) 1-42 or 1-40 could be added to culture cells at a normally toxic concentration of 25-50 μM. After 4 days of treatment, viability could be assessed by measurement of lactate dehydrogenase (LDH) released into culture medium. LDH could be measured in 20 μl aliquots of conditioned defined DMEM using a standard 340 nm kinetic LDH assay (Sigma Catalog #228-20) in a 96 well format. Assays could be performed at 37° C. in a PC-driven EL340 Microplate Biokinetics plate reader (Bio-Tek Instruments) using Delta Soft II software (v.3.30B, BioMetallics, Inc.) for data analysis. Quality control standards containing normal and elevated levels of serum LDH (for example, Sigma Enzyme controls 2N and 2E) could be run with every assay. Results could be expressed as units of LDH/L where 1 unit is defined as the amount of enzyme that would catalyze the formation of 1 micromole of nicotinamide adenine dinucleotide per minute under conditions of the assay. For protection studies, synthetic procyanidin B2 could be added to cultures prior to and/or concurrently with Aβ treatment. Activity of the test compound could be illustrated by a decrease in LDH released into the media (a neurotoxic indicator), as compared to control.

Assay 2

Five to fifty woman could be selected for a clinical study. The women should be post-menopausal, i.e., having ceased menstruating for between 6 and 12 months prior to the study's initiation, diagnosed with early stage Alzheimer's disease (AD), and expecting to have worsening symptoms of AD within the study period, but should be in good general health otherwise. The study could have a placebo control group, i.e., the women could be divided into two groups, one of which receives synthetic procyanidin B2 of this disclosure and the other receives a placebo. The patients could be benchmarked as to memory, cognition, reasoning, and other symptoms associated with AD. Women in the test group would receive a therapeutic dose of the compound per day by the oral or i.v. route. They should continue this therapy for 6-36 months. Accurate records should be kept as to the benchmarked symptoms in both groups and at the end of the study these results could be compared. The results could be compared between members of each group. In addition, the results for each patient could be compared to the symptoms reported by each patient before the study began. Activity of the procyanidin B2 test compound could be illustrated by the attenuation of the typical cognitive decline and/or behavioral disruptions associated with AD.

Example 10

General Methodology and Results Obtained Pertaining to a New Method of Rapid Isolation of Procyanidin B2 from the Bark Powder of *Uncaria tomentosa*

A three stage isolation procedure of the main procyanidin compound present in bark powder of *Uncaria tomentosa* (i.e., cat's claw), from a crude methanol extract is disclosed. Procyanidin B2 (i.e., epicatechin-4β→8-epicatechin) was isolated and purified from ground bark powder of *Uncaria tomentosa* using the methodology disclosed below. The yield of procyanidin B2 in *Uncaria tomentosa* bark powder was estimated to be 0.05% (by weight).

Figure 15:
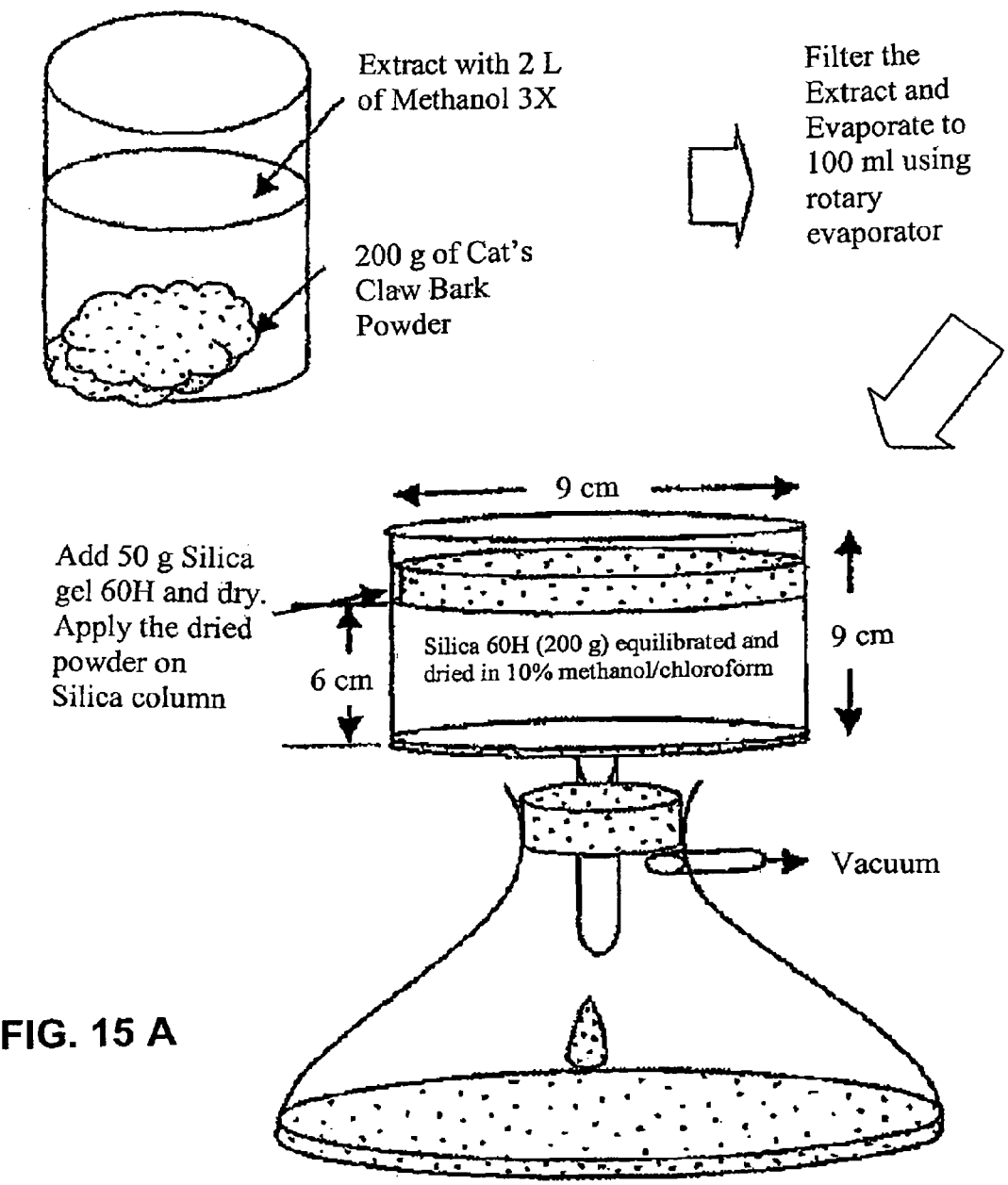
FIG. 15 is a schematic representation of steps for the isolation of procyanidin B2 from cat's claw (i.e., *Uncaria tomentosa*) bark powder in accordance with the present disclosure.
Figure 15:
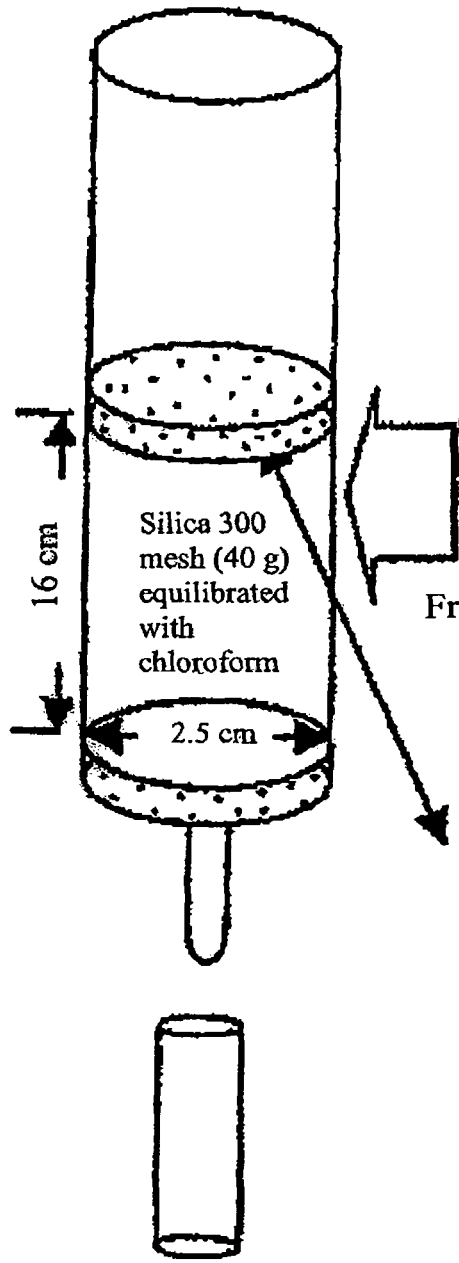
Figure 15:
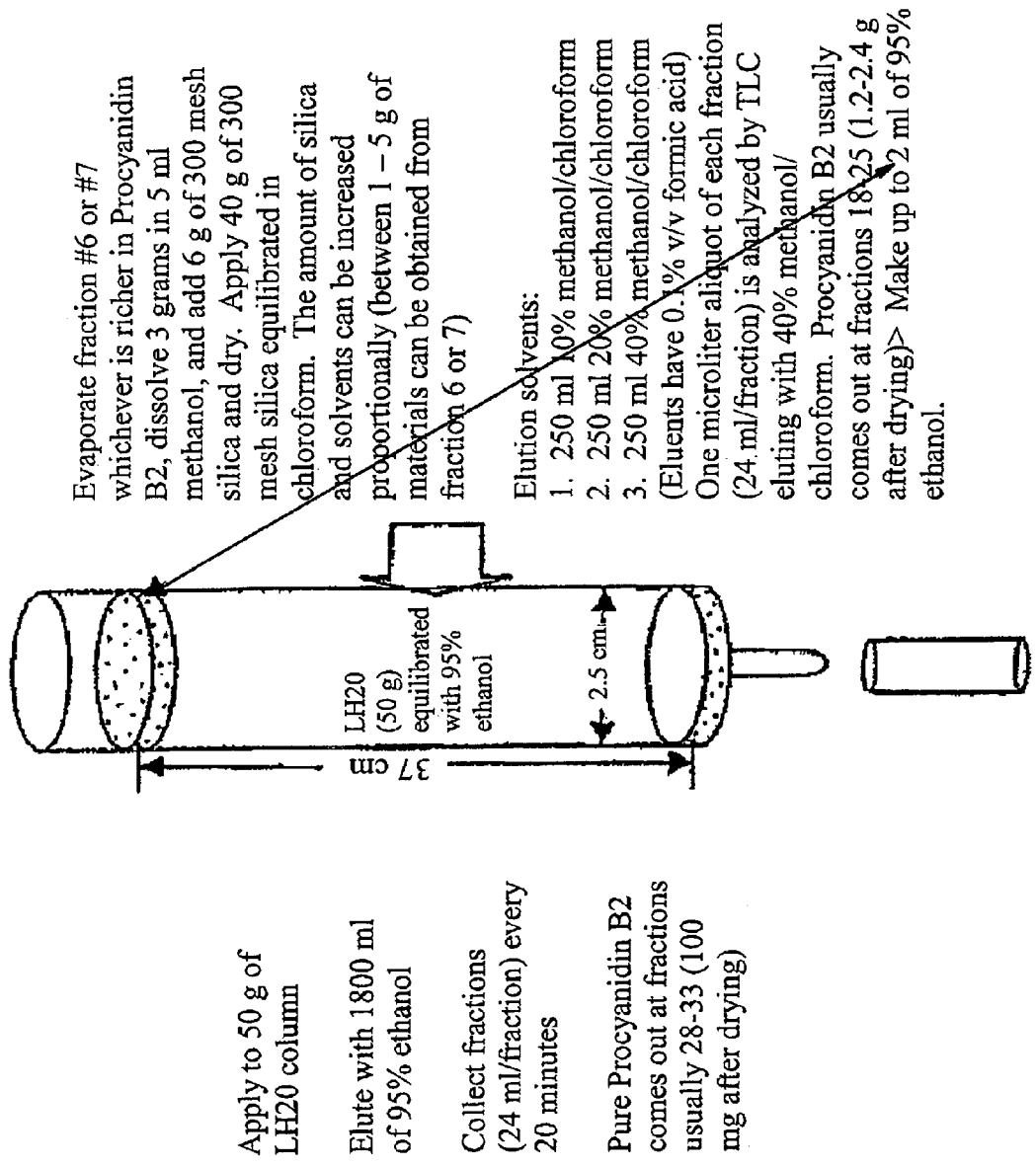
Figure 19:
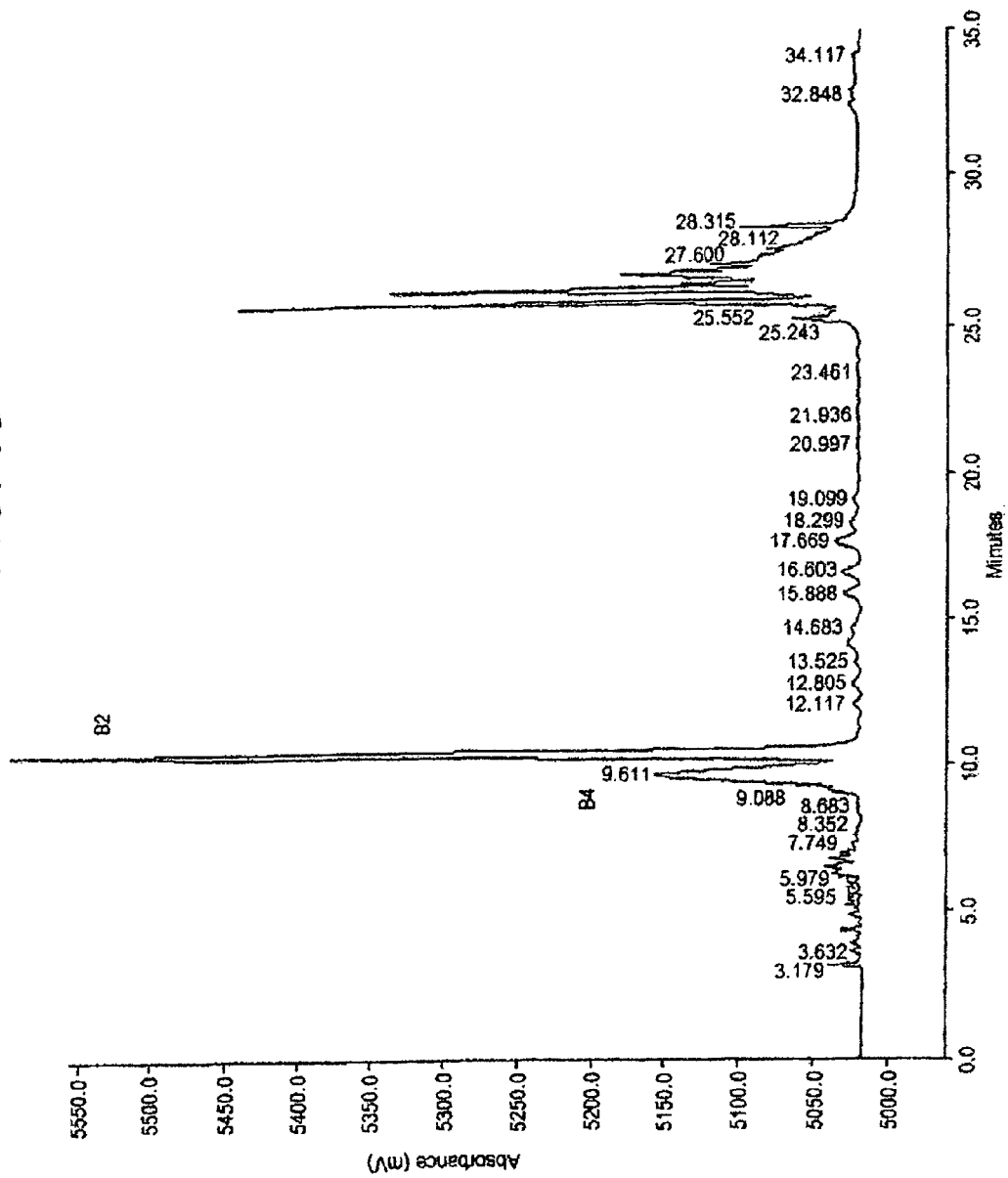
FIG. 19 is an HPLC analysis of combined fractions 18-25 of Example 12, eluted off the silica 300 mesh column with 20-40% methanol in chloroform. These fractions contain predominantly procyanidin B2, with some procyanidin B4.
Figure 20:
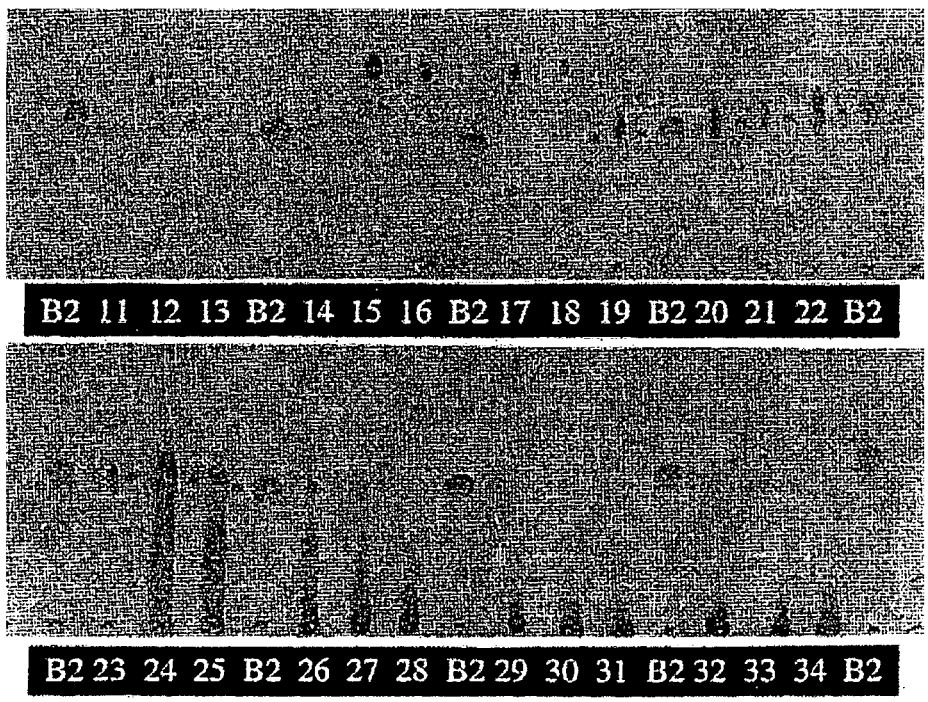
FIG. 20 is a TLC profile of fractions 11-34 of Example 12, eluted off the silica 300 mesh column with appropriate solvents. Pure procyanidin B2 is also run as a standard. TLC demonstrated that procyanidin B2 (*) is primarily observed in fractions 18-25.
Figure 21:
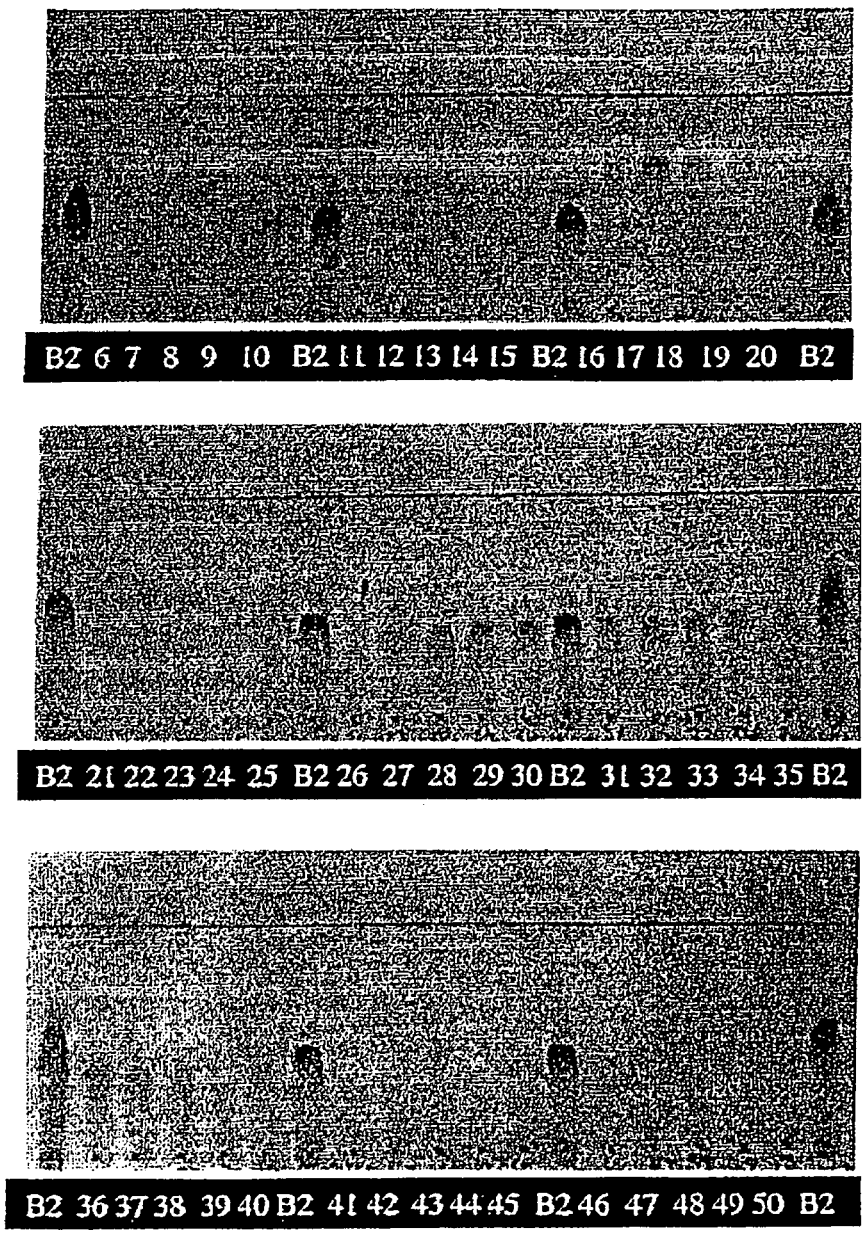
FIG. 21 is a TLC profile of fractions 6-50 of Example 12, eluted off the Sephadex LH20 column equilibrated and eluted with 95% ethanol. Pure procyanidin B2 is also run as a standard. TLC demonstrates that pure procyanidin B2 is observed in fractions 28-33.
Figure 22:
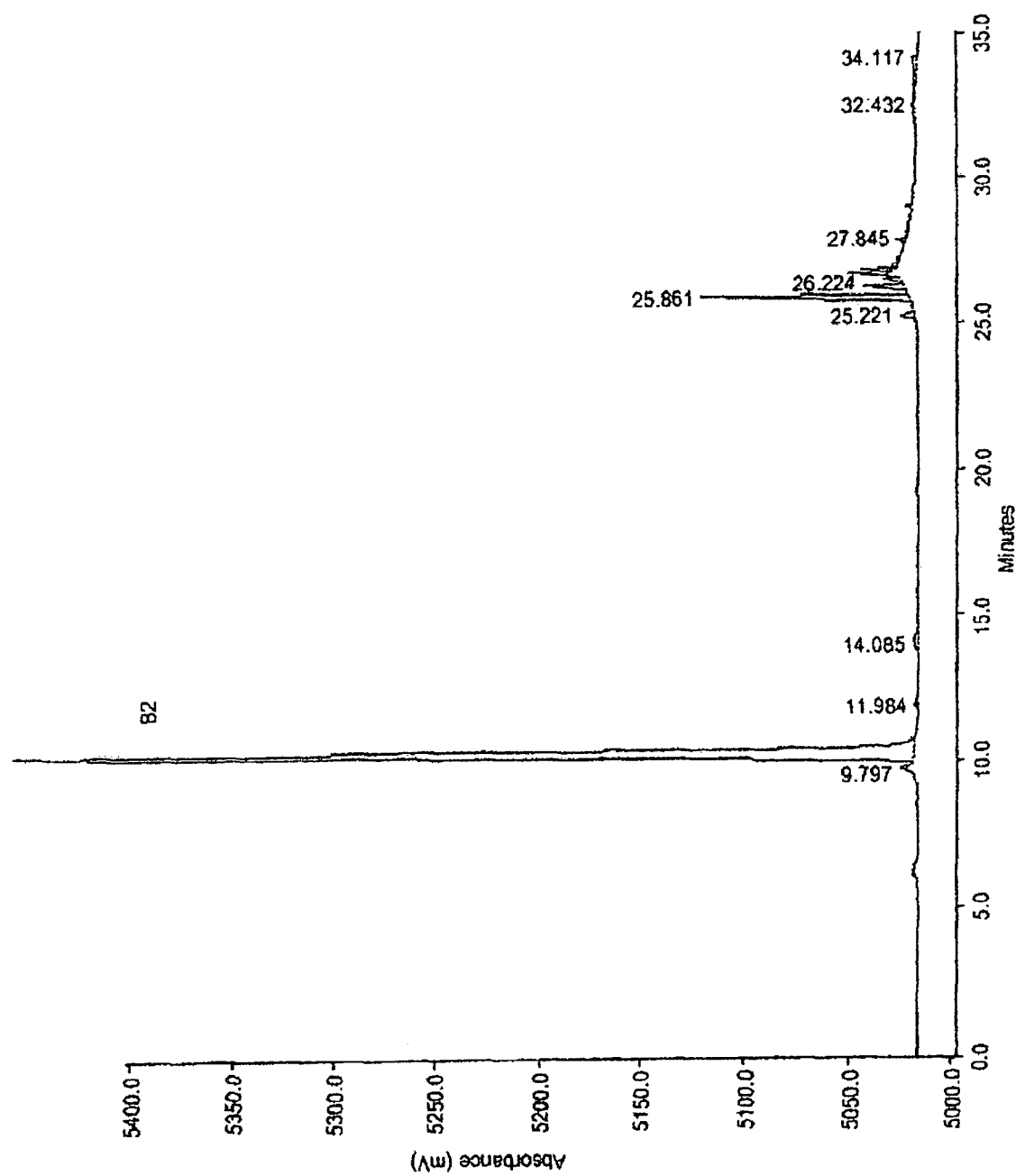
FIG. 22 is a HPLC profile of procyanidin B2 following purification by Sephadex LH20 column chromatography of Example 12. Procyanidin B2 is present in >95% yield.
Figure 23:
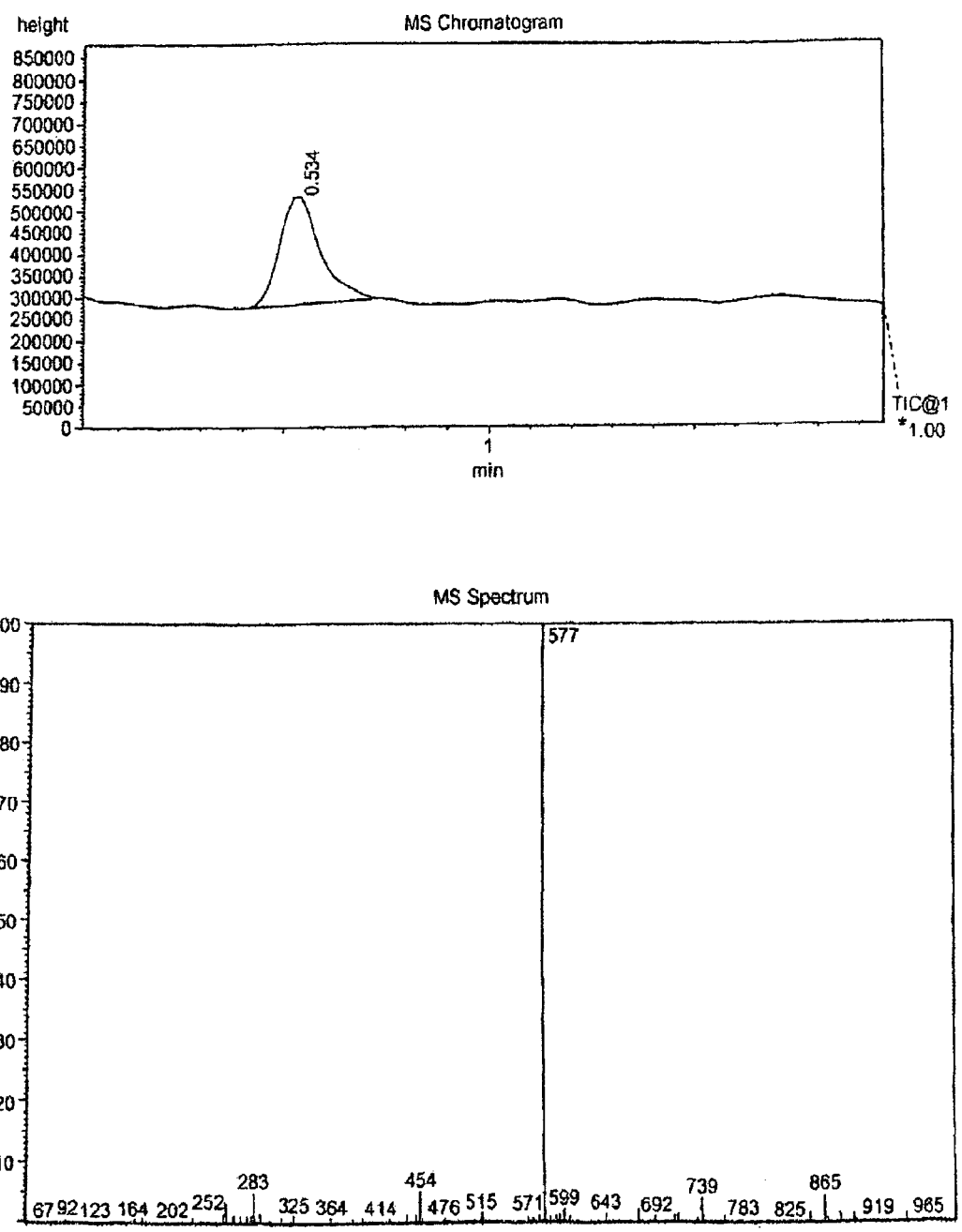
FIG. 23 is the −ve ion electrospray mass spectrum of procyanidin B2 isolated as described in of Example 12.

The main procyanidin component, procyanidin B2, of the *Uncaria tomentosa* bark extract was isolated by a series of chromatographic techniques, with monitoring by high pressure liquid chromatography (HPLC). Ground bark powder from *Uncaria tomentosa* (200 g) was extracted three times sequentially with (2 liters) of methanol to give a crude extract (FIG. 15). This extract was then separated by vacuum flash chromatography over silica gel 60H, to give a fraction in which the main procyanidins were concentrated (FIGS. 15-18). Further separation was achieved by gravity column chromatography over silica gel, when 20% to 40% methanol in chloroform gave a fraction rich in procyanidin B2 and procyanidin B4 (1.21 g) (FIGS. 19 and 20). Column chromatography over Sephadex LH20 eluting with 95% aqueous ethanol then gave a pure sample of the procyanidin B2 (89-150 mg) (FIGS. 21-23).

Example 11

General Experimental Procedures Used in the Isolation of Procyanidin B2 from the Bark Powder of *Uncaria tomentosa*

All solvents were distilled before use and were removed by rotary evaporation at temperatures up to 300. Merck silica gel 60, 200-400 mesh, 40-63 μm, (Sigma Chem. Co., St. Louis Mo., USA; catalog #S057, or Aldrich catalog #28.8594) was used for silica gel gravity column chromatography, and Merck silica gel TLC grade 60H, 5-40 μm, (Sigma Chem. Co. catalog #S6628 or Aldrich catalog #40,3709), was used for silica gel vacuum flash chromatography. TLC was carried out using Merck DC-plastikfolien Kieselgel 60 $F_{254}$, (Sigma Chem. Co., catalog #Z29,299-0), first visualised with an ultraviolet (UV) lamp in a viewing cabinet (Aldrich Cat #Z16, 943-9), and then sprayed with 1% vanillin in 80% sulfuric acid with 20% ethanol, and heated to 120° C. for 10-20 minutes or until sufficient color intensity was obtained. Alternatively, the spots in TLC plates could be visualized by dipping in 5% aqueous ferric chloride solution.

Optical rotations were measured on a Perkin-Elmer 241 polarimeter. Mass, UV, and infrared (IR) spectra were recorded on Kratos MS-80, Shimadzu UV 240, and Perkin-Elmer 1600 FTIR instruments, respectively. NMR spectra, at 25° C., were recorded at 500 or 300 MHz for $^1$H, and 125 or 75 MHz for $^{13}$C on Varian INOVA-500 or VXR-300 spectrometers. Chemical shifts are given in ppm on the δ scale referenced to the solvent peak $CH_3OH$ at 3.30, $CD_3OD$ at 49.3 ppm, $CHCl_3$ at 7.25, $CDCl_3$ at 77.0; $(CH_3)_2CO$ at 2.15 and $(CD_3)_2CO$ at 30.5.

HPLC Conditions

The analytical HPLC equipment consisted of a Waters 717 autosampler, 600 pump and controller, and a 2487 UV detector controlled by Omega software. Samples were analyzed by using an RP-18 semi-preparative column (Phenomenex Jupiter 5 μm C18 300A, 250×10 mm) with a guard column (Phenomenex SecurityGuard cartridge containing a C18 ODS 4×3 mm, 5 μm column) fitted at 30° C. Samples (5 μl) were analyzed using a mobile phase flow rate of 5.0 ml/min, with UV detection at 280 nm. Solvent A consisted of $CH_3CN$ containing 5% $H_2O$ and 0.1% trifluoroacetic acid (TFA). Solvent B consisted of $H_2O$ containing 0.1% TFA. The composition of the mobile phase as a function of time is given in Table 2.

TABLE 2

| Time (minutes) | % Solvent A | % Solvent B |
|---|---|---|
| 0 | 11 | 89 |
| 20 | 11 | 89 |
| 30 | 100 | 0 |
| 31 | 11 | 89 |

Alternatively, the analytical HPLC equipment consisted of a Hewlett Packard (HP) 1100 series HPLC with diode array detector. Samples were analyzed by using an RP-18 analytical column (Phenomenex LUNA 5 μm C18 100A, 250×4.6 mm) with a guard column (Phenomenex SecurityGuard cartridge containing a C18 ODS 4×3 mm, 5 μm column) fitted at 25° C. Samples (5 μl) were analyzed using a mobile phase flow rate of 1.0 ml/min, with UV detection at 280 nm and 210 nm. Solvent A consisted of $CH_3CN$ containing 0.1% TFA. Solvent B consisted of $H_2O$ containing 0.1% TFA. The composition of the mobile phase as a function of time is given in Table 3.

TABLE 3

| Time (minutes) | % Solvent A | % Solvent B |
|---|---|---|
| 0 | 14 | 86 |
| 15 | 14 | 86 |
| 21 | 95 | 5 |
| 11 | 14 | 86 |

Example 12

Methods for the Isolation of Procyanidin B2 from the Bark Powder of *Uncaria tomentosa* Extraction of Ground Bark Powder from *Uncaria tomentosa*

A sample of bark powder from 200 grams of *Uncaria tomentosa* (i.e., cat's claw) was extracted by stirring with 2 liters of methanol for 30 minutes, and then allowing the mixture to settle for 30 minutes (see FIG. 15). This was then followed by filtration using a Whatman Filter paper 41 (or VWR brand Grade #415 or 417 or 410 or 315 or 313 or 454 or 474, 494, or any other capable filter paper). The process was repeated on the residue two more times. The filtrates were then combined and evaporated in vacuo (i.e., using a rotary evaporator) at below 30° C. to a volume of approximately 100 ml.

Preparing a Flash Vacuum Silica Gel Column 200 grams of dry silica gel TLC grade 60H was placed into a large sinter glass Buchner funnel (9 cm×10.5 cm, or larger) with 6 μm frits, since the size of silica beads are 10 um. The silica gel was compacted down evenly using a #14 rubber stopper. The sintered glass funnel was connected to a 500 ml vacuum flask using a #6.5 rubber stopper with one hole. Vacuum (650 mm Hg) was then applied to the vacuum flask, and the solvent (350 ml) was added all at once. The solvent front was seen to move in a straight line down the column. The vacuum was applied until the column was dry again (if the solvent front was not even, the silica had to be recompacted). The 350 ml solvent used to test and condition the silica surface was discarded at this point.

Flash Vacuum Silica Gel Fractionation of the Methanol Extract

To the 100 ml of methanol extract (from extraction of 200 g of ground bark powder) was added 50 grams of TLC grade silica gel 60H, and the solvents removed in vacuo at 30 to 40° C. (FIG. 15). The residue was then crushed into powder and loaded dry onto a silica gel 60H flash vacuum column (200 g) prepared in 10% methanol in chloroform (350 ml) (described above). Elution of this column with 10% methanol in chloroform (2×250 ml) (i.e., fractions #1 and #2), 20% methanol in chloroform (2×250 ml) (i.e., fractions #3 and #4), 40% methanol in chloroform (2×250 ml) (i.e., fractions #5 and #6), then 60% methanol in chloroform (2×250 ml) (i.e., fractions #7 and #8) gave 8 fractions.

The first fraction was eluted with the first solvent mix (i.e., 250 ml of 10% methanol in chloroform, as described above), by adding it all at once, carefully (or with the help of an inverted funnel, with an 8-9 cm wide end, so as not to disturb the surface of the column), under vacuum, and the vacuum was continued until the column was dry again. The 500 ml vacuum flask containing the first eluted sample (i.e., fraction #1) was saved for analysis. The second solvent mix (i.e., 250 ml in 10% methanol in chloroform) was then used to elute the second fraction, and also saved for analysis. Likewise, the third through eight solvent mixes (as described above) were used to elute a total of 8 fractions.

Figure 16:
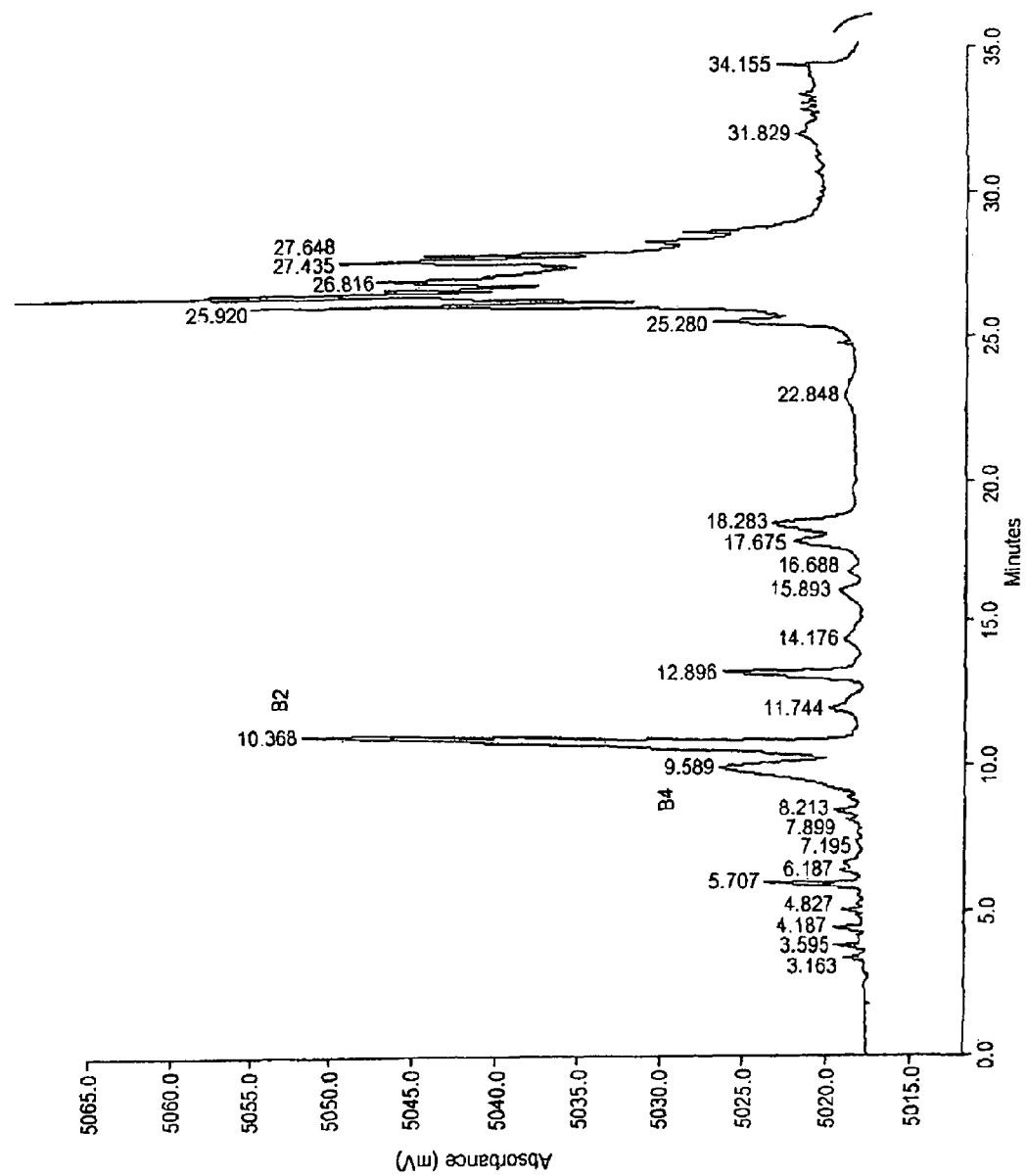
FIG. 16 is an HPLC analysis of fraction 7 of Example 12, eluted off the silica gel 60H with 60% methanol in chloroform. This fraction is shown to contain procyanidin B2 (10.368 minutes), with some procyanidin B4 (9.589 minutes).
Figure 17:
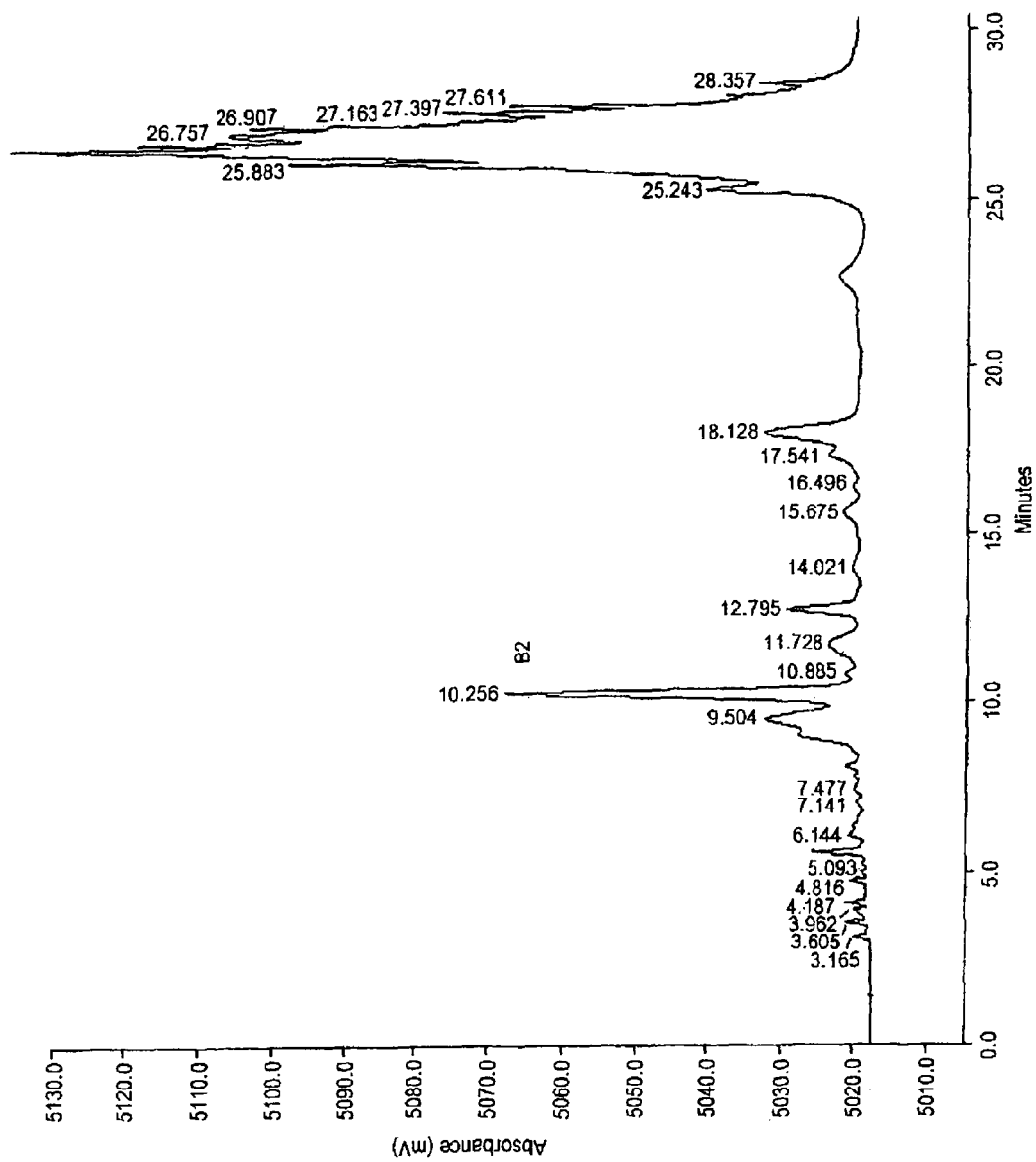
FIG. 17 is an HPLC analysis of fraction 8 of Example 12, eluted off the silica gel 60H with 60% methanol in chloroform. This fraction contains less procyanidin B2 (10.256 minutes), and even less procyanidin B4 (9.504 minutes), than fraction 7 of FIG. 16.
Figure 18:
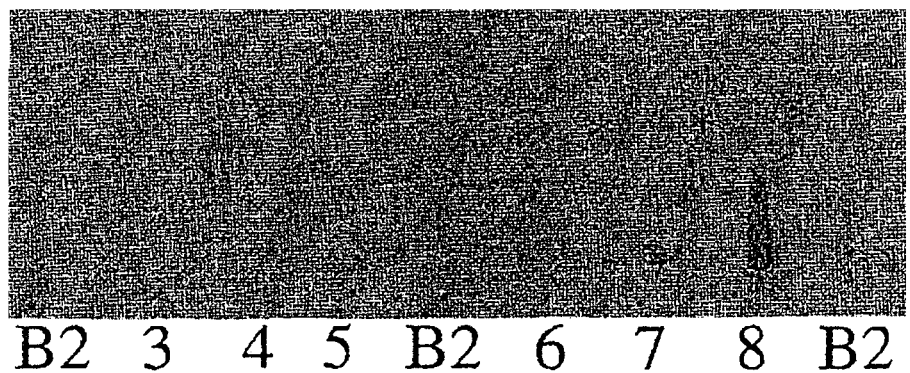
FIG. 18 is a TLC profile of fractions 3-8 of Example 12, eluted off the silica gel 60H with the appropriate solvents. Pure procyanidin B2 was also run as a standard. TLC demonstrates that procyanidin B2 (*) is primarily observed in fraction 7, with less in fractions 6 and 8.

Thin layer chromatography (TLC) analysis of the fractions eluting with 40% methanol in chloroform, comparing with a pure sample of procyanidin B2, showed procyanidin B2 to be mostly contained in fraction 7 (1.5-5.0 g), with lesser amounts in fractions 6 and 8 (FIG. 18). This was confirmed by HPLC analysis (FIGS. 16 and 17).

Important Features of this Column

Solvent fractions are advantageously added all at once, without allowing the column surface to dry out during addition of the solvent. The column is preferably taken back to dryness between fractions. It works best with a rapid change of polarity between fractions.

Silica Gel Column Chromatography Fractionation of Flash Vacuum Fraction 6 or 7

A solution of fraction 7 (~3 grams) in methanol (2 ml) was added to a silica gel (40 g) gravity column (3×30 cm or 4.8×30 cm or 2.5×30 cm), prepared in chloroform. Since the amount of materials in fraction 6 or 7 can vary from 1.5-5.0 grams, the amount of silica needs to account for the increase or decrease in the amount of sample coming out of fraction 6 or 7 above. For example, if the amount of material coming out of fraction 7 is 3 grams, then the amount of silica should be 40 grams. To facilitate sample application and fractionation using this column, the sample is dried in 2 weight equivalents of silica (200-400 mesh) as was implemented using flash chromatography as described above. The sample dried in silica was cleanly applied over the silica gel (200-400 mesh) column equilibrated in chloroform. After application, the sample was eluted with 10% methanol in chloroform (100 ml for 20 g silica column, 200 ml for 40 g silica column, 250 ml for 50 g silica column, and so on), followed by elution with 20% methanol in chloroform (100 ml for 20 g silica column, 200 ml for 40 g silica column, 250 ml for 50 g silica column, and so on), followed by elution with 40% methanol in chloroform (100 ml for 20 g silica column, 200 ml for 40 g silica column, 250 ml for 50 g silica column, and so on), all preferably containing formic acid (1 drop per 50 ml). Fractions (12 ml/fraction for 20 gram silica column, 24 ml/fraction for 40-50 g silica column, and so on) were collected, and 1 µl/fraction was analysed by TLC eluting with 40% methanol in chloroform to locate procyanidins B2 and B4. Procyanidins B2 and B4 were found to be contained in fractions 13 to 21 when using the 20 gram silica column, or in fractions 18-25, when using the 40-50 gram silica column (FIG. 20). The fractions containing predominantly procyanidin B2 were combined to give a brown gum (1.20-2.40 g), which was confirmed by HPLC analysis (FIG. 19).

Sephadex LH20 Column Fractionation of Silica Gel Fractions

Silica gel fractions 13 to 21 (1.20-2.4 g) (when using 20 gram silica column, or fractions 18-25 (when using the 40-50 gram silica column) were dissolved in 2 ml of 95% aqueous ethanol, and then loaded onto a 50 gram Sephadex LH20 column, prepared in 95% aqueous ethanol. The column was eluted with 1800 ml of 95% aqueous ethanol, and 24 ml fractions were collected every 20 minutes. HPLC analysis showed fractions 28 to 33 to contain pure procyanidin B2 (89 mg) (FIG. 21), which was confirmed by HPLC (FIG. 22) and mass spectroscopy (FIG. 23) analyses.

Example 13

Alternative Methods for the Isolation of Procyanidin B2 from the Bark Powder of *Uncaria tomentosa*

Extraction of Ground Bark Powder from *Uncaria tomentosa*

Alternative 1:

A sample of *Uncaria tomentosa* bark powder (200 g) was extracted by stirring in methanol (2000 ml) overnight followed by filtration using Whatman Filter paper 41 (or VWR brand Grade #415 or 417 or 410 or 315 or 313 or 454 or 474, 494, or the like capable filter paper). This process is preferably repeated on the residue a further two times. The filtrates were combined then evaporated in vacuo at below 30° C. to a volume of 100 ml.

Alternative 2:

A sample of *Uncaria tomentosa* bark powder (200 g) was extracted by stirring in 30 methanol (2000 ml) overnight followed by centrifuging at 3000×g for 20 min. and filtration using Whatman Filter paper 41 (or VWR brand Grade #415 or 417 or 410 or 315 or 313 or 454 or 474, 494, or the like filter paper). This process is preferably repeated on the residue a further two times. The filtrates were combined then evaporated in vacuo at below 30° C. to a volume of 100 ml.

Alternative 3:

A sample of *Uncaria tomentosa* bark powder (200 g) was extracted by stirring in methanol (2000 ml) for 0.5-1 hr followed by allowing the residue to settle for 0.5 hr. The upper portion cleared of residue was filtered using Whatman Filter paper 41 (or VWR brand Grade #415 or 417 or 410 or 315 or 313 or 454 or 474, 494, or the like filter paper). This process is preferably repeated on the residue a further three times. The filtrates were combined then evaporated in vacuo at below 30° C. to a volume of 100 ml.

Alternative 4:

A sample of *Uncaria tomentosa* bark powder (200 g) was extracted by stirring in methanol (4000 ml) for 0.5-1 hr followed by centrifuging at 3000×g for 20 min. The upper portion cleared of residue was filtered using Whatman Filter paper 41 (or VWR brand Grade #415 or 417 or 410 or 315 or 313 or 454 or 474, 494, or the like filter paper). This process is repeated on the residue a further three times. The filtrates were combined then evaporated in vacuo at below 30° C. to a volume of 100 ml.

Alternative 5:

A sample of *Uncaria tomentosa* bark powder (600 g) was extracted by stirring in methanol (6000 ml) for 0.5-1 hr followed by allowing the residue to settle for 0.5 hr. The upper portion cleared of residue was filtered using Whatman Filter paper 41 (or VWR brand Grade #415 or 417 or 410 or 315 or 313 or 454 or 474, 494, or the like filter paper). This process is repeated on the residue a further three times. The filtrates were combined then evaporated in vacuo at below 30° C. to a volume of 200 ml.

Flash Vacuum Silica Gel Fractionation of the Methanol Extract

Alternative 1:

TLC grade silica gel 10-40 µm Type H (50 g) (Sigma Chemical Co. St. Luis, Mo.) was added to the methanol extract (from extraction of 200 g of ground Cat's Claw bark) (100 ml) in a 250 ml vacuum flask. The mixture was mixed using a spatula, and dried in vacuo by attaching a vacuum tube to the flask, and covering the mouth of the flask with rubber stopper number 9. Heating the vacuum flask in a 50° C. water bath facilitated the drying.

To set up the vacuum flash silica gel column, a Buchner funnel (9×10.5 cm) with glass frit (6 µm cut off) (Thomas Scientific) was inserted into a one hole Kjeldahl rubber stopper. To avoid exposure to silica dust particles, the Buchner funnel was packed inside a transparent plastic bag with 200 g of TLC grade silica gel 10-40 µm Type H (50 g) (Sigma Chemical Co. St. Luis, Mo.). The top layer of silica was compacted evenly using a B14 rubber stopper or any similar flat surface object. The Buchner funnel with packed silica was then attached to a 500 ml vacuum flask. Under vacuum, 350 ml of 10% methanol in chloroform was added all at once. The solvent front was seen as a straight horizontal line going down the column. The vacuum was applied until the silica was dry again. If the solvent front was not even, the silica was recompacted and the column was made again.

The dried silica bound extract (sample) was applied on the Buchner funnel containing compacted silica, and the sample was compacted with B 14 Rubber stopper under vacuum. The fractions were then eluted with the following solvents:

1. 250 ml of 10% methanol in chloroform
2. 250 ml of 10% methanol in chloroform
3. 250 ml of 20% methanol in chloroform
4. 250 ml of 20% methanol in chloroform
5. 250 ml of 40% methanol in chloroform
6. 250 ml of 40% methanol in chloroform
7. 250 ml of 60% methanol in chloroform
8. 250 ml of 60% methanol in chloroform Each solvent (as described above) was added under vacuum carefully and at once, so as not to disturb the surface compacted silica, and the vacuum was continued until the silica was dry again. Before the next solvent the vacuum was turned off and the Buchner funnel containing silica was moved to a new vacuum flask for the next fraction. The vacuum flask containing the fraction was saved for analysis. The process was repeated until all 8 fractions were collected. The column or the silica in the Buchner funnel are preferably dried between fractions.

Alternative 2:

TLC grade silica gel 10-40 µm Type H (50 g) (Sigma Chemical Co. St. Luis, Mo.) 30 was added to the methanol extract (from extraction of 600 g of ground Cat's Claw bark) (200 ml) in a 500 ml vacuum flask. The mixture was mixed using a spatula and dried in vacuo by attaching a vacuum tube to the flask, and covering the mouth of the flask with rubber stopper number 9. Heating the vacuum flask in a 50° C. water bath facilitated the drying.

To set up the vacuum flash silica gel column, a Buchner funnel (12.5×14.7 cm) with glass frit (6 µm cut off) (Thomas Scientific) was inserted into a one hole number 9 rubber stopper. To avoid exposure to silica dust particles, the Buchner funnel was packed inside a transparent plastic bag with 600 g of TLC grade silica gel 10-40 µm Type H (Sigma Chemical Co. St. Luis, Mo.). The top layer of the silica was compacted evenly using a B 16 Rubber stopper or any similar flat surface object. The Buchner funnel with packed silica was then attached to a 2 l vacuum flask. Under vacuum, 1 liter of 10% methanol on chloroform was added all at once. The solvent front was seen as a straight horizontal line going down the column. The vacuum was applied until the silica was dry again. If the solvent front was not even, the silica was recompacted and the column was retested.

The dried silica bound extract (sample) was applied onto the Buchner funnel containing compacted silica, and the sample was compacted with a B16 Rubber stopper under vacuum. The fractions were then eluted with the following solvents:

1. 750 ml of 10% methanol in chloroform
2. 750 ml of 10% methanol in chloroform
3. 750 ml of 20% methanol in chloroform
4. 750 ml of 20% methanol in chloroform
5. 750 ml of 40% methanol in chloroform
6. 750 ml of 40% methanol in chloroform
7. 750 ml of 60% methanol in chloroform
8. 750 ml of 60% methanol in chloroform Each solvent described above was added under vacuum carefully and all at once, so as not to disturb the surface compacted silica, and the vacuum was continued until the silica was dry again. Before the next solvent elution, the vacuum was turned off and the Buchner funnel containing silica was moved to a new vacuum flask for the next fraction. The vacuum flask containing the fraction was saved for analysis. The process was repeated until all eight fractions were collected TLC Analysis of Each Fraction Each of the fractions above were analyzed by thin layer chromatography (TLC) using Silica TLC plates (5×10 cm) containing a 250 µm layer of silica gel 60 with fluorescent indicator (Aldrich). About 2 µl of each fraction was dotted onto the TLC plate, 1 µl at a time with drying in between using a hot air blow dryer, at a region of the plate 1 cm from the edge. Samples were applied such that they were 0.5 cm apart. A pure procyanidin B2 sample was also dotted in a similar way to serve as an internal standard. The plate was developed in a 12×11×8 cm closed TLC glass development chamber containing 50 ml of 40% methanol in chloroform. The development was stopped when the solvent front was 1 cm away from top edge of the plate. The compound was visualized under ultraviolet light (254 nm) where the silica fluoresces, while the spot with the compound was quenched resulting in a dark spot. The $R_f$ of pure procyanidin B2 under this condition was about 0.5. The plate can also be sprayed with 1% (w/v) vanillin in concentrated sulfuric acid with 20% ethanol followed by heating at 120° C. (800 watt oven) until the dark spots attain maximum color intensity (10-20 minutes). Alternatively $FeCl_3$ in water or alcohol between 0.1 to 5% by weight can be sprayed onto the plate to detect procyanidin B2 giving a dark spot. Alternatively, the plate can be dipped quickly in this solution and dried either using a hair dryer, or by just letting it stand at room temperature. The image can be photographed with either a scanner or a regular camera for data recording. Under these conditions, procyanidin B2 is normally found in fraction 6 or 7. This fraction was dried in vacuo, resulting in 1.5-5 grams of dried material, and made up to 2-6 ml in methanol.

Silica Gel Column Chromatography Fractionation of Flash Vacuum Fraction 6 or 7.

Alternative 1:

A 2 ml methanol solution of fraction 6 or 7 (containing 1.54 g) was applied to a silica gel gravity column (20 g, Silica gel 200-400 mesh, 60 A from Aldrich or Silica gel 230-400 mesh, 60 A pore with 38-63 µm bead size from Sigma) prepared in chloroform. Once this column was prepared, it was not allowed to dry during the chromatographic run. Fractions were eluted with solvents containing 1 drop of formic acid per 50 ml in the following order.

1. 100 ml of 10% methanol in chloroform
2. 100 ml of 20% methanol in chloroform
3. 100 ml of 40% methanol in chloroform Fractions (12 ml each) were collected and analyzed by TLC as above. Procyanidin B2 and B4 usually were observed in fractions 13-21.

Alternative 2:

A 2-ml methanol solution of fraction 6 or 7 (containing 1.5 g) was added to silica gel 3 g, Silica gel 200-400 mesh, 60 A from Aldrich or Silica gel 230-400 mesh, 60 A pore with 38-63 µm bead size from Sigma) in a 250 ml vacuum flask. The mixture was mixed using a spatula and dried in vacuo by attaching a vacuum tube to the flask and covering the mouth of the flask with rubber stopper number 9. The vacuum flask was heated in a 50° C. water bath to facilitate the drying.

A silica gel gravity column (20 grams, 200-400 mesh, 60 A from Aldrich or Silica gel 230-400 mesh, 60 A pore with 38-63 µm bead size from Sigma) (4.8×30 cm) was prepared in chloroform. The sample bound in silica above was applied to the column with 5 cm of chloroform above the bed. Once this column was prepared it was not allowed to dry during the chromatographic run. Fractions were eluted with solvents containing 1 drop of formic acid per 50 ml in the following order.

1. 100 ml of 10% methanol in chloroform
2. 100 ml of 20% methanol in chloroform
3. 100 ml of 40% methanol in chloroform Fractions (12 ml each) were collected and analyzed by TLC as above. Procyanidin B2 and procyanidin B4 usually were observed in fractions 13-21.

Alternative 3: Scale Up

A 6 ml methanol solution of fraction 6 or 7 (containing 5 g) was added to silica gel (10 g, Silica gel 200-400 mesh, 60 A from Aldrich or Silica gel 230-400 mesh, 60 A pore with 38-63 µm bead size from Sigma) in a 250 ml vacuum flask. The mixture was mixed using a spatula and dried in vacuo by attaching a vacuum tube to the flask and covering the mouth of the flask with rubber stopper number 9. The vacuum flask was heated in a 50° C. water bath to facilitate the drying.

A silica gel gravity column (60 grams, 200-400 mesh, 60 A from Aldrich or Silica gel 230-400 mesh, 60 A pore with 38-63 µm bead size from Sigma) (4.8×30 cm) was prepared in chloroform. The sample bound in silica above was applied to the column with 5 cm of chloroform above the bed. Once this column was prepared it was not allowed to dry during the chromatographic run. Fractions were eluted with solvents containing 1 drop of formic acid per 50 ml in the following order.

1. 300 ml of 10% methanol in chloroform
2. 300 ml of 20% methanol in chloroform
3. 300 ml of 40% methanol in chloroform Fractions (36 ml each) were collected and analyzed by TLC as above. Procyanidin B2 and B4 usually were observed in fractions 13-21.

Alternative 4: Scale Up

A 10 ml methanol solution of fraction 6 or 7 (containing 7.5 g) was loaded to a silica gel cartridge (100 g, Varian) mounted to a Chromazone Flash chromatography System (Varian) equilibrated in chloroform. Once this column was prepared it was not allowed to dry during the chromatographic run. Fractions were eluted at about 20 ml/minute with solvents containing 0.1% (v/v) formic acid in the following order.

1. 500 ml of 10% methanol in chloroform
2. 500 ml of 20% methanol in chloroform
3. 500 ml of 40% methanol in chloroform Fractions (60 ml each) were collected and analyzed by TLC as above. Procyanidin B2 and B4 usually were observed in fractions 13-21.

Sephadex LH20 column fractionation

Fraction 13-21 (1.2 g) were dissolved in 95% aqueous ethanol (2 ml) then loaded onto a Sephadex LH20 (40 g) column (2.5×37 cm), prepared in 95% aqueous ethanol. The column was eluted with 95% aqueous ethanol (1000 ml) by gravity, and fractions were collected every 10 minutes (12 ml). Under these conditions, fractions 44-49 contained pure procyanidin B2 as determined by TLC and confirmed by HPLC.

HPLC Analysis

The analytical HPLC equipment consisted of an HP 1100 series with diode array detector. Samples were analyzed by using an RP-18 analytical column (Phenomenex LUNA 5 µm C18 100A, 250×4.6 mm) with a guard column (Phenomenex SecurityGuard cartridge containing a C18 ODS 4×3 mm, 5 µm column) fitted at 25° C. Samples (5 µl) were analyzed using a mobile phase flow rate of 1.0 ml/min, with UV detection at 280 nm and 210 nm, as described above.

Example 14

Isolated and Purified Procyanidin B2 is a Potent Inhibitor/Disrupter of Aβ Fibrils Purified procyanidin B2 (i.e., epicatechin-4β→8-epicatechin), isolated as described herein, is a potent inhibitor/disrupter of Alzheimer's disease beta-amyloid protein (Aβ) fibrils. In a first set of studies, the efficacy of procyanidin B2 isolated directly from the bark powder of *Uncaria tomentosa*, was compared to EDTA, for its ability to cause a disassembly/disruption of pre-formed amyloid fibrils of Alzheimer's disease (i.e., consisting of Aβ 1-42 fibrils).

In one study, Thioflavin T fluorometry was used to determine the effects of procyanidin B2 isolated from *Uncaria tomentosa* bark powder (purified as disclosed herein) and EDTA (as a negative control). In this assay, Thioflavin T binds specifically to fibrillar amyloid, and this binding produces a fluorescence enhancement at 485 nm that is directly proportional to the amount of amyloid fibrils formed. The higher the fluorescence, the greater the amount of amyloid fibrils formed (Naki et al, Lab. Invest. 65:104-110, 1991; Levine III, Protein Sc. 2:404-410, 1993; Amyloid Int. J. Exp. Clin. Invest. 2:1-6, 1995).

In this study, 25 µM of pre-fibrillized Aβ 1-42 (Bachem Inc) was incubated at 37° C. for 1 week either alone, or in the presence of procyanidin B2 isolated from *Uncaria tomentosa* bark powder or EDTA (at an Aβ:test compound weight ratios of 1:1, 1:0.1, 1:0.01 or 1:0.001). Following 3-days of co-incubation, 50 µl of each incubation mixture was transferred into a 96-well microtiter plate containing 150 µl of distilled water and 50 µl of a Thioflavin T solution (i.e., 500 mM Thioflavin T in 250 mM phosphate buffer) (pH 6.8). The fluorescence was read at 485 nm (444 nm excitation wavelength) using an ELISA plate fluorometer after subtraction with buffer alone or compound alone, as blank.

Figure 24:
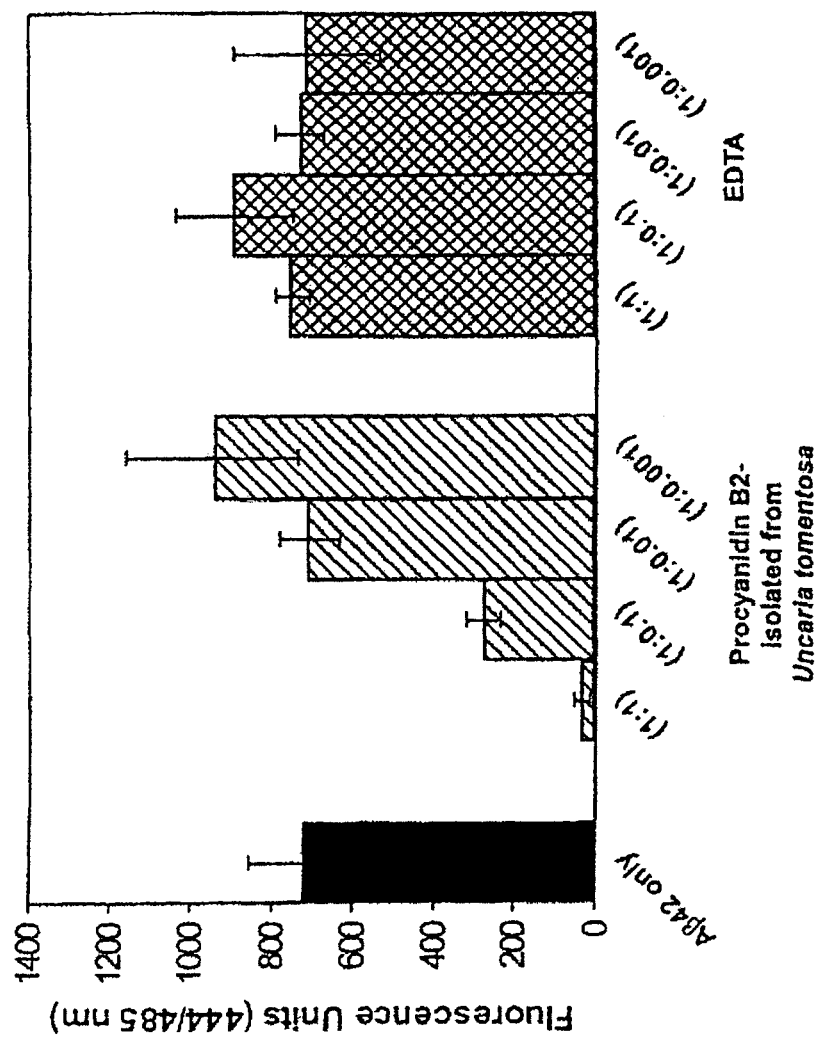
FIG. 24 is a Thioflavin T fluorometry assay demonstrating that procyanidin B2 isolated in accordance with the present disclosure is effective for the disruption/disassembly of Aβ fibrils.

The results of day 3 incubations are presented in FIG. 24. Whereas EDTA caused no significant inhibition of Aβ 1-42 fibrils at all concentrations tested, procyanidin B2 isolated from bark powder of *Uncaria tomentosa* caused a dose-dependent disruption/disassembly of preformed Aβ 1-42 fibrils. Isolated procyanidin B2 caused a significant (p<0.01) 95.5+/−2.7% disruption when used at an Aβ:Procyanidin B2 wt/wt ratio of 1:1, and a significant (p<0.05) 61.6+/−5.8% disruption when used at an Aβ:Procyanidin B2 wt/wt ratio of 1:0.1. This study indicated that isolated procyanidin B2 produced by the methods disclosed herein is a potent disruptor of Alzheimer's disease type Aβ fibrils, and exerts its effect in a dose-dependent manner.

The disruption of Aβ 1-42, even in its monomeric form, was confirmed by a study involving the use of SDS-PAGE and Western blotting methods (not shown). In this latter study, triplicate samples of pre-fibrillized Aβ 1-42 (25 µM) was incubated at 37° C. for 3 and 7 days either alone, or in the presence of procyanidin B2 isolated from *Uncaria tomentosa* bark powder or EDTA. A 5 µg aliquot of each sample was then filtered through a 0.2 µm filter. Protein recovered from the filtrate was then loaded, and run on a 10-20% Tris-Tricine SDS-PAGE, blotted to nitrocellulose and detected by ECL using an Aβ-antibody (clone 6E10; Senetek). In this study, Aβ 1-42 was detected as a 4 kilodalton band (i.e., monomeric Aβ) following incubation alone, or in the presence of EDTA, at both 3 and 7 days. Aβ 1-42 monomers were not detected following incubation of Aβ 1-42 with procyanidin B2 isolated from *Uncaria tomentosa* bark powder, by 7 days of co-incubation (not shown) suggesting that this compound is capable of causing a disappearance of monomeric Aβ 1-42. This study confirmed that purified procyanidin B2 was also capable of causing a disruption/removal of monomeric Aβ 1-42.

Example 15

Isolated Procyanidin B2 is a Potent Inhibitor of Fibrillar Aβ Binding to Congo Red In the Congo red binding assay (as described below) the ability of a given test compound to alter amyloid (in this case, Aβ) binding to Congo red is quantified. In this assay, Aβ 1-42+/−test compounds were incubated for 3 days and then vacuumed through a 0.2 µm filter. The amount of Aβ 1-42 retained in the filter (i.e., "retentate") was then quantitated following staining of the filter with Congo red. After appropriate washing of the filter, any lowering of the Congo red color on the filter in the presence of the test compound (compared to the Congo red staining of the amyloid protein in the absence of the test compound) was indicative of the test compound's ability to diminish/alter the amount of aggregated and congophilic Aβ.

Figure 25:
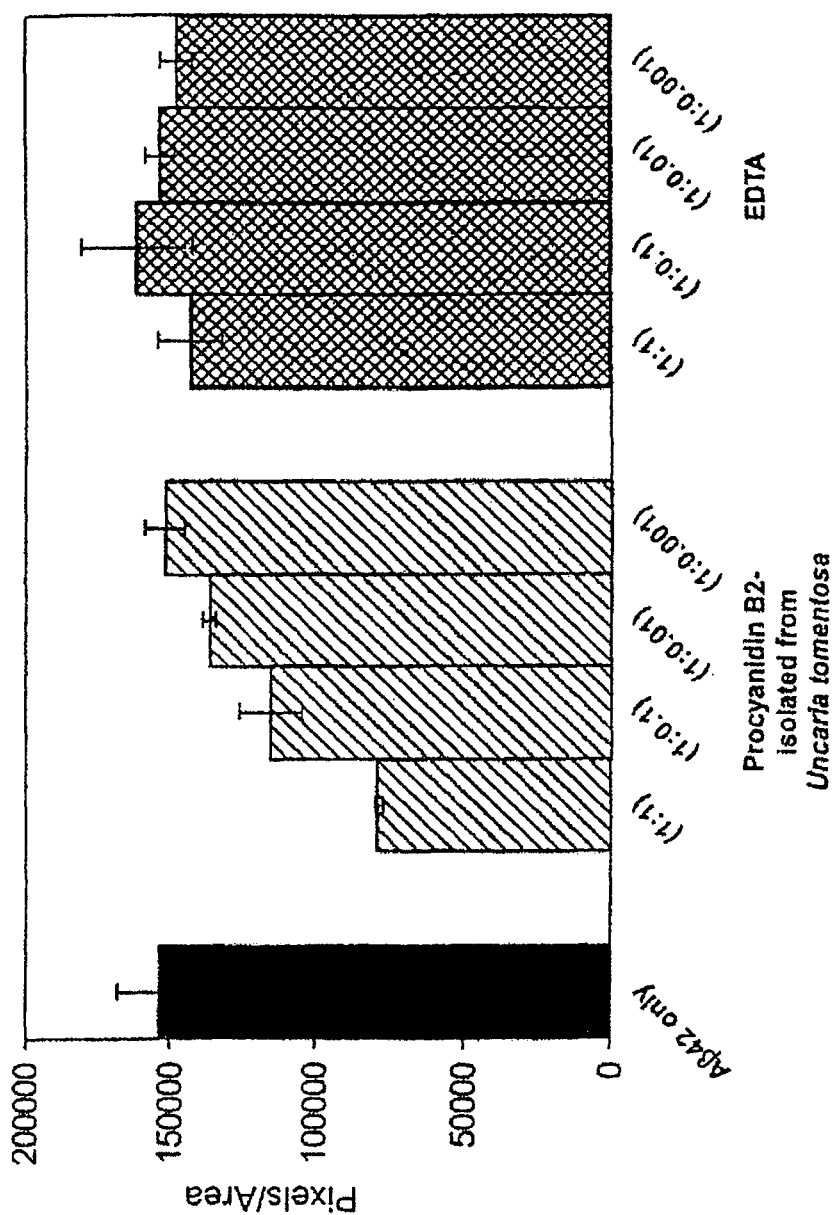
FIG. 25 is a Congo red binding assay demonstrating that procyanidin B2 isolated in accordance with the present disclosure is effective for the inhibition of Aβ fibrillogenesis.

In one study (FIG. 25), the ability of Aβ fibrils to bind Congo red in the absence or presence of increasing amounts of procyanidin B2 isolated from *Uncaria tomentosa* bark powder or EDTA (at an Aβ:test compound weight ratios of 1:1, 1:0.1, 1:0.01 or 1:0.001) was determined. The results of day 3 incubations are presented in FIG. 25. Whereas EDTA caused no significant inhibition of Aβ 1-42 fibril binding to Congo red at all concentrations tested, isolated procyanidin B2 caused a dose-dependent inhibition of fibrillar Aβ 1-42 binding to Congo red. Isolated procyanidin B2 caused a significant ($p<0.01$) 36.33+/−4.3% inhibition of Congo red binding to Aβ 1-42 fibrils when used at an Aβ:Procyanidin B2 wt/wt ratio of 1:1. This study indicated that isolated procyanidin B2 produced by the methods disclosed herein is a potent inhibitor of Alzheimer's disease type Aβ fibril binding to Congo red, and exerts its effect in a dose-dependent manner.

While this disclosure has been described in conjunction with specific embodiments and examples, it will be apparent to a person of ordinary skill in the art, having regard to this disclosure, that equivalents of the specifically disclosed materials and techniques will also be applicable to this disclosure; and such equivalents are intended to be included within the following claims.

What is claimed is:

1. A method for improving cognitive performance and/or slowing cognitive decline in a patient suffering from an amyloid disease comprising administering a therapeutically effective amount of a procyanidin B2 to reduce formation, deposition, accumulation, or persistence of beta-amyloid protein fibrils in the patient wherein the amount of the procyanidin B2 administered is between about 0.1 mg/kg of body weight and about 1000 mg/kg of body weight of the patient per day.

2. The method of claim 1, wherein the amount of the procyanidin B2 administered is between about 1 mg/kg of body weight per day and about 100 mg/kg of body weight per day.

3. The method of claim 1, wherein the amount of the procyanidin B2 administered is between about 10 mg/kg of body weight per day and about 100 mg/kg of body weight per day.

4. A method for improving learning and/or memory in an Alzheimer's patient comprising administering a therapeutically effective amount of a procyanidin B2 to reduce formation, deposition, accumulation, or persistence of beta-amyloid protein fibrils in the patient, wherein the amount of the procyanidin B2 administered is between about 0.1 mg/kg of body weight and about 1000 mg/kg of body weight of the patient per day.

5. The method of claim 4, wherein the amount of the procyanidin B2 administered is between about 1 mg/kg of body weight per day and about 100 mg/kg of body weight per day.

6. The method of claim 5, wherein the amount of the procyanidin B2 administered is between about 10 mg/kg of body weight per day and about 100 mg/kg of body weight per day.

7. A method for improving cognitive performance and/or slowing cognitive decline in a patient suffering from an amyloid disease comprising administering a therapeutically effective amount of a procyanidin B2 wherein the amount of the procyanidin B2 administered is between about 0.1 mg/kg of body weight and about 1000 mg/kg of body weight of the patient per day.

8. The method of claim 7, wherein the amount of the procyanidin B2 administered is between about 1 mg/kg of body weight per day and about 100 mg/kg of body weight per day.

9. The method of claim 7, wherein the amount of the procyanidin B2 administered is between about 10 mg/kg of body weight per day and about 100 mg/kg of body weight per day.

* * * * *